(12) United States Patent
Hamburger et al.

(10) Patent No.: US 11,780,914 B2
(45) Date of Patent: Oct. 10, 2023

(54) PACAP ANTIBODIES AND USES THEREOF

(71) Applicant: AMGEN INC., Thousand Oaks, CA (US)

(72) Inventors: Agnes E. Hamburger, Newbury Park, CA (US); Cen Xu, Newbury Park, CA (US); Hong Sun, Belmont, MA (US); Yuan D. Shih, Calabasas, CA (US); Dohan Weeraratne, Ventura, CA (US)

(73) Assignee: AMGEN INC.

( * ) Notice: Subject to any disclaimer, the term of this patent is extended or adjusted under 35 U.S.C. 154(b) by 293 days.

(21) Appl. No.: 17/031,674

(22) Filed: Sep. 24, 2020

(65) Prior Publication Data

US 2021/0095016 A1    Apr. 1, 2021

Related U.S. Application Data

(63) Continuation of application No. 16/063,152, filed as application No. PCT/US2016/067054 on Dec. 15, 2016, now Pat. No. 10,822,408.

(60) Provisional application No. 62/267,822, filed on Dec. 15, 2015.

(51) Int. Cl.
| | |
|---|---|
| A61K 39/395 | (2006.01) |
| C07K 16/26 | (2006.01) |
| C12N 15/13 | (2006.01) |
| A61P 25/06 | (2006.01) |
| C07K 16/42 | (2006.01) |
| A61K 39/00 | (2006.01) |
| A61K 9/00 | (2006.01) |

(52) U.S. Cl.
CPC ............. *C07K 16/26* (2013.01); *A61P 25/06* (2018.01); *C07K 16/4283* (2013.01); *A61K 9/0019* (2013.01); *A61K 2039/505* (2013.01); *C07K 2317/24* (2013.01); *C07K 2317/34* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,486,472 | A | 1/1996 | Suzuki et al. |
| 5,858,787 | A | 1/1999 | Onda et al. |
| 5,892,004 | A | 4/1999 | Ohtaki et al. |
| 5,973,117 | A | 10/1999 | Onda et al. |
| 6,017,533 | A | 1/2000 | Moro et al. |
| 6,242,563 | B1 | 6/2001 | Dong |
| 6,399,316 | B1 | 6/2002 | Onda et al. |
| 6,462,016 | B1 | 10/2002 | Wakita et al. |
| 9,546,203 | B2 | 1/2017 | Gavin et al. |
| 2002/0155533 | A1 | 10/2002 | Onda et al. |
| 2002/0182729 | A1 | 12/2002 | DiCicco-Bloom et al. |
| 2005/0129687 | A1 | 6/2005 | Vizzard et al. |
| 2005/0142133 | A1 | 6/2005 | Lazar et al. |
| 2006/0062785 | A1 | 3/2006 | Freson et al. |
| 2006/0160996 | A9 | 7/2006 | Lazar et al. |
| 2007/0054843 | A1 | 3/2007 | Yeomans et al. |
| 2009/0215895 | A1 | 8/2009 | Ferrante et al. |
| 2009/0291900 | A1 | 11/2009 | Yeomans et al. |
| 2010/0112601 | A1 | 5/2010 | Shirakawa et al. |
| 2011/0021426 | A1 | 1/2011 | Toll et al. |
| 2013/0196908 | A1 | 8/2013 | Toll et al. |
| 2018/0362643 | A1 | 12/2018 | Hamburger et al. |

FOREIGN PATENT DOCUMENTS

| | | |
|---|---|---|
| CN | 102939303 A | 2/2013 |
| EP | 0 522 159 B1 | 12/2001 |
| EP | 2 048 162 A1 | 4/2009 |
| EP | 1 098 906 B1 | 11/2009 |
| EP | 1 928 484 B1 | 2/2010 |
| EP | 2 161282 A1 | 3/2010 |
| WO | 00/05260 A1 | 2/2000 |
| WO | 2004/062684 A | 7/2004 |
| WO | 2004/099249 A2 | 11/2004 |
| WO | 2005/073164 A1 | 8/2005 |
| WO | 2007/022070 A2 | 2/2007 |
| WO | 2007/025249 A2 | 3/2007 |
| WO | 2009/033489 A2 | 3/2009 |
| WO | 2010/066125 A1 | 6/2010 |
| WO | 2011/017122 A1 | 2/2011 |
| WO | 2011/076781 A1 | 6/2011 |
| WO | 2012/125850 A1 | 9/2012 |
| WO | 2013/093809 A1 | 6/2013 |
| WO | 2013/177062 A2 | 11/2013 |
| WO | 2016/168757 A1 | 10/2016 |
| WO | 2016/168760 A1 | 10/2016 |

(Continued)

OTHER PUBLICATIONS

Bee et al. (2013), "Determining the binding affinity of therapeutic monoclonal antibodies towards their native unpurified antigens inhuman serum", PLOS One, 8(11)e80501:1-13.
Bendig, Mary M. (1995), "Humanization of rodent monoclonal antibodies by CDR grafting", Methods: A Companion to Methods in Enzymology, 9:83-93.
Bourgault et al.(2009), "Molecular and conformational determinants of pituitary adenylate cyclase-activating polypeptide (PACAP) for activation of the PAC1 receptor", J. Med. Chem., 52:3308-3316.
Casset et al. (2003), "A peptide mimetic of an anti-CD4 monoclonal antibody by rational design", Biochem. Biophys. Res. Comm., 307:198-205.

(Continued)

*Primary Examiner* — Christine J Saoud
*Assistant Examiner* — Jon M Lockard
(74) *Attorney, Agent, or Firm* — Angela L. Purcell

(57) ABSTRACT

The present invention relates to monoclonal antibodies that specifically bind to human pituitary adenylate cyclase activating polypeptide (PACAP) and pharmaceutical compositions comprising such antibodies. Methods of treating or preventing headache conditions, such as migraine and cluster headache, using the monoclonal antibodies are also described.

19 Claims, 5 Drawing Sheets

Specification includes a Sequence Listing.

(56) References Cited

FOREIGN PATENT DOCUMENTS

| WO | 2016/168762 A2 | 10/2016 |
| WO | 2016/168768 A2 | 10/2016 |

OTHER PUBLICATIONS

Chen et al. (1999), "Selection and analysis of an optimized anti-VEGF antibody: Crystal structure of an affinity-matured Fab in complex with antigen", J. Mol. Biol., 293:865-881.

Colman, P.M. (1994), "Effects of amino acid sequence changes on antibody-antigen interactions", Research in Immunology, 145:33-36.

De La Lastra et al. (1999), "Epitope mapping of 10 monoclonal antibodies against the pig analogue of human membrane cofactor protein (MCP)", Immunol., 96:663-670.

Drake et al. (2004), "Characterizing high-affinity antigen/antibody complexes by kinetic-and equilibrium-based methods", Anal. Biochem., 328(1):35-43.

Drake et al. (2012), "Biacore surface matrix effects on the binding kinetics and affinity of an antigen/antibody complex", Anal. Biochem., 429(1):58-69.

Goetzl et al., "PAC1 and VIP receptors", pp. 2249-2253, DOI:10.1006/rwcy.2000.23009.

Guirland et al. (2003), Direct cAMP signaling through g-protein-coupled receptors mediates growth cone attraction induced by pituitary adenylate cyclase-activating polypeptide, J. Neurosci., 23(6):2274-2283.

Heinrich et al. (2010), "Comparison of the results obtained by ELISA and surface plasmon resonance for the determination of antibody affinity", J. Immunol. Methods, 352(1-2):13-22.

Inooka et al. (2001), "Conformation of a peptide ligand bound to its G-protein coupled receptor", Nature Struct. Biol., 8(2):161-165.

ISR and Written Opinion for PCT/US2014/029128 dated Oct. 8, 2014.

ISR and Written Opinion for PCT/US2016/067054 dated May 17, 2017.

Laburthe et al. (2007), "Class II G protein-coupled receptors for VIP and PACAP: Structure, models of activation and pharmacology", Peptides, 28:1631-1639.

Lerner et al. (Sep. 2007), "Maxadilan, a PAC1 receptor agonist from sand flies", Peptides; 28(9):1651-1654. NIH-Public Access.

MacCallum et al. (1996), "Antibody-antigen interactions: Contact analysis and binding site topography", J. Mol. Biol., 262:732-745.

Moretti et al. (2006), "PACAP and Type I PACAP receptors in human prostate cancer tissue", Annals N.Y. Acad. Sci., 1070(1):440-449.

Moro, et al. (1999), "Functional characterization of structural alterations in the sequence of the vasodilatory peptide maxadilan yields a pituitary adenylate cyclase-activating peptide type 1 receptor-specific antagonist", J. Biol. Chem., 274(33):23103-23110.

Pascalis et al. (2002), "Grafting of 'abbreviated' complementarity-determining regions containing specificity-determining residues essential for ligand contact to engineer a less immunogenic humanized monoclonal antibody", J. Immunol., 169:3076-3084.

Paul, "Fv structure and diversity in three dimensions", Fundamental Immunology, 3$^{rd}$ ed., pp. 292-295, 1993.

Rudikoff et al. (1982), "Single amino acid substitution altering antigen-binding specificity", PNAS, 79:1979-1983.

Saldanha, Jose W. (2007), "Molecular Engineering I: Humanization", Chapter 6, Handbook of Therapeutic Antibodies, Stefan Dubel ed., pp. 119-144.

Sazinsky, S.L. (2008), "Aglycosylated immunoglobulin G1 variants productively engage activating Fc receptors", PNAS, 105(51):20167-20172.

Schulz, et al. (2004), "Immunocytochemical identification of VPAC1, VPAC2, and PAC1 receptors in normal and neoplastic human tissues with subtype-specific antibodies", Clin. Cancer Res., 10:8235-8242.

Schwarzhoff et al. (1995), "Specific monoclonal antibodies neutralize the action of PACAP 1-27 or PACAP 1-38 on intestinal muscle strips in vitro", Regulatory Peptides, 55(1): 57-66.

Schytz et al. (2008), "PACAP38 induces migraine-like attacks in patients with migraine without aura", Brain, 132:16-25.

Schytz et al. (2010), "The PACAP receptor: A novel target for migraine treatment", Neurotherap.: J. Am. Soc. Experiment. NeuroTherap., 7(2):191-196.

Suzuki et al. (1993), "Production of immunoreactive pituitary adenylate cyclase activating polypeptide (PACAP) by human neuroblastoma cells, IMR-32: Detection and characterization with monoclonal and polyconal antibodies against different epitopes of PACAP", J. Biochem., 113(5):549-556.

Syed et al. (2012), "Pituitary adenylate cyclase-activating polypeptide (PACAP) potently dilates middle meningeal arteries: Implications for migraine", J. Molec. Neurosci., 48(3):574-583.

Tuka et al. (2012), "Peripheral and central alterations of pituitary adenylate cyclase activating polypeptide-like immunoreactivity in the rat in response to activation of the trigeminovascular system", Peptides, 33(2):307-316.

Vaudry et al. (2000), "Pituitary adenylate cyclase-activating polypeptide and its receptors: from structure to functions", Pharmacol. Rev., 52:269-324.

Vaudry et al. (2009), "Pituitary adenylate cyclase-activating polypeptide and its receptors: 20 years after the discovery", Pharmacol. Rev., 61(3):283-357.

Wu et al. (1999), "Humanization of a murine monoclonal antibody by simultaneous optimization of framework and CDR residues", J. Mol. Biol, 294:151-162.

Zagami et al. (2014), "Pituitary adenylate cyclase activating polypeptide and migraine", Annals Clin. Trans. Neurol., 1(12):1036-1040.

Zvirbliene et al. (1999), "Production and characterization of monoclonal antibodies to pituitary adenylate cyclase activating polypeptide type I receptor", Hybridoma, Liebert, New York, NY, US, 18(4):335-342.

Freson et al., "PACAP and its receptor VPAC1 regulate megakaryocyte maturation: therapeutic implications," Blood, vol. 111, pp. 1885-1893 (2008).

PACAP ANTIBODIES AND USES THEREOF

CROSS-REFERENCE TO RELATED APPLICATIONS

This application is a continuation of U.S. application Ser. No. 16/063,152, filed Jun. 15, 2018, which is the national stage entry of PCT Application No. PCT/US2016/067054, filed Dec. 15, 2016, which claims the benefit of U.S. Provisional Application No. 62/267,822, filed Dec. 15, 2015, all of which are hereby incorporated by reference in their entireties.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Sep. 24, 2020, is named A-2013-US-CNT_ST25.txt and is 108,304 bytes in size.

FIELD OF THE INVENTION

The present invention relates to the field of biopharmaceuticals. In particular, the invention relates to monoclonal antibodies that specifically bind to human pituitary adenylate cyclase-activating polypeptide (PACAP), pharmaceutical compositions comprising the monoclonal antibodies, and methods of producing and using such monoclonal antibodies.

BACKGROUND OF THE INVENTION

Migraines are episodic headaches that can involve significant pain, are often accompanied by nausea, vomiting, and extreme sensitivity to light (photophobia) and sound (phonophobia), and are sometimes preceded by sensory warning symptoms or signs (auras). Migraine is a highly prevalent disease worldwide with approximately 12% of the European population, and 18% of women, 6% of men in the United States suffering from migraine attacks (Lipton el al, Neurology, Vol. 68:343-349, 2007; Lipton et al., Headache, Vol. 41:646-657, 2001). A study to assess the prevalence of migraine in the United States reported that nearly half the migraine patient population had three or more migraines per month (Lipton et al, Neurology, Vol. 68:343-349, 2007). Additionally, migraines are associated with a number of psychiatric and medical comorbidities such as depression and vascular disorders (Buse et al., J. Neurol. Neurosurg. Psychiatry, Vol. 81:428-432, 2010; Bigal et al., Neurology, Vol. 72:1864-1871, 2009). Most of the current migraine therapies are either not well tolerated or ineffective (Loder et al., Headache, Vol. 52:930-945, 2012; Lipton et al, 2001); thus, migraine remains an unmet medical need.

A major component of migraine pathogenesis involves the activation of the trigeminovascular system. The release of trigeminal and parasympathetic neurotransmitters from perivascular nerve fibers (Sanchez-del-Rio and Reuter, Curr. Opin. Neurol., Vol. 17(3):289-93, 2004) result in vasodilation of the cranial blood vessels and has been suggested to be associated with the onset of migraine headaches (Edvinsson, Cephalagia, Vol. 33(13): 1070-1072, 2013; Goadsby et al., New Engl J Med., Vol. 364(4):257-270, 2002).

Pituitary adenylate cyclase-activating polypeptides (PACAP) are 38-amino acid (PACAP38), or 27-amino acid (PACAP27) peptides that were first isolated from an ovine hypothalamic extract on the basis of their ability to stimulate cAMP formation in anterior pituitary cells (Miyata et al., Biochem Biophys Res Commun., Vol. 164:567-574, 1989; Miyata et al., Biochem Biophys Res Commun., Vol. 170: 643-648, 1990). PACAP belongs to the VIP/secretin/glucagon superfamily. The sequence of PACAP 27 corresponds to the 27 N-terminal amino acids of PACAP 38 and shares 68% identity with vasoactive intestinal polypeptide (VIP) (Pantaloni el al., J. Biol. Chem., Vol. 271: 22146-22151, 1996; Pisegna and Wank, Proc. Natl. Acad. Sci. USA, Vol. 90: 6345-49, 1993; Campbell and Scanes, Growth Regul., Vol. 2:175-191, 1992). The major form of PACAP peptide in the human body is PACAP38, and the pharmacology of PACAP 38 has not been shown to be different from the pharmacology of PACAP27. Three PACAP receptors have been reported: one receptor that binds PACAP with high affinity and has a much lower affinity for VIP (PAC1 receptor), and two receptors that recognize PACAP and VIP equally well (VPAC1 and VPAC2 receptors) (Vaudry et al., Pharmacol Rev., Vol. 61:283-357, 2009).

Human experimental migraine models using PACAP as a challenge agent to induce migraine-like headaches support the approach for antagonism of the PACAP/PAC1 signaling pathway as a treatment for migraine prophylaxis. Infusion of PACAP38 caused headaches in healthy subjects and migraine-like headaches in migraine patients (Schytz et al., Brain, Vol. 132:16-25, 2009). In addition, in the same model, VIP did not cause migraine-like headaches in migraine patients (Rahmann et al., Cephalalgia, Vol. 28:226-236, 2008). The lack of migraine-like headache induction from VIP infusion suggests that PACAP38 peptide's effects are mediated through the PAC1 receptor, rather than VPAC1 or VPAC2 receptors, because VIP has a much higher affinity at the latter two receptors. These data suggest that pharmacological agents that inhibit PACAP-activation of the PAC1 receptor have the potential to treat migraine.

SUMMARY OF THE INVENTION

The present invention provides isolated antigen binding proteins that specifically bind to human PACAP. In certain embodiments, the isolated antigen binding proteins specifically bind to both human PACAP38 and human PACAP27. In other embodiments, the isolated antigen binding proteins specifically bind to human PACAP38, but not human PACAP27. The isolated antigen binding proteins can be used to inhibit, interfere with, or modulate the biological activity of PACAP, including inhibiting or reducing PACAP-induced activation of PAC1, VPAC1, and/or VPAC2 receptors, inhibiting or reducing vasodilation, and ameliorating or treating symptoms of migraine and other vascular headaches.

In one embodiment of the invention, the isolated antigen binding protein is an isolated monoclonal antibody or binding fragment thereof. The monoclonal antibody can be a chimeric antibody, humanized antibody, or fully human antibody. In some embodiments, the monoclonal antibody or binding fragment thereof specifically binds to a C-terminal domain of PACAP38, for example, at an epitope within amino acids 28 to 38 of SEQ ID NO: 1, at an epitope within amino acids 28 to 37 of SEQ ID NO: 1, or at an epitope within amino acids 34 to 38 of SEQ ID NO: 1. Such C-terminal binding monoclonal antibodies or binding fragments thereof may bind to a polypeptide consisting of the sequence of SEQ ID NO: 4 and/or a polypeptide consisting of the sequence of SEQ ID NO: 126. In certain embodiments, a C-terminal binding monoclonal antibody or binding fragment thereof may bind to a polypeptide consisting of the sequence of SEQ ID NO: 4 with a binding affinity at least 2-fold greater than that for a polypeptide consisting of the sequence of SEQ ID NO: 115. In other embodiments, the monoclonal antibody or binding fragment thereof specifically binds to an N-terminal domain of PACAP38, for example at an epitope within amino acids 1 to 13 of SEQ ID NO: 1. These N-terminal binding monoclonal antibodies or binding fragments thereof may bind a polypeptide consisting of the sequence of SEQ ID NO: 5. In certain embodiments, the monoclonal antibody or binding fragment thereof does not significantly bind to human VIP.

In certain embodiments, the antigen binding proteins of the invention (e.g. monoclonal antibodies and binding fragments thereof) are neutralizing antigen binding proteins. For instance, the antigen binding proteins inhibit the binding of PACAP38 and/or PACAP27 to the human VPAC1, VPAC2, or PAC1 receptor and prevent or reduce receptor activation. In one embodiment, the antigen binding proteins inhibit PACAP38 binding to the PAC1 receptor and inhibit PACAP38-induced activation of the receptor. For instance, in some embodiments, the antigen binding proteins inhibit PACAP38-induced activation of human PAC1 receptor with an IC50 less than 5 nM as measured by a cell-based cAMP assay. In other embodiments, the antigen binding proteins inhibit PACAP38-induced activation of human PAC1 receptor with an IC50 less than 1 nM as measured by a cell-based cAMP assay. In certain embodiments, the antigen binding proteins of the invention inhibit PACAP38-induced activation of the human PAC1 receptor with an IC50 between about 100 pM and about 500 pM as measured by a cell-based cAMP assay. In some embodiments, the antigen binding proteins do not significantly inhibit the binding of PACAP27 to the PAC1 receptor or PACAP27-induced activation of the receptor.

The present invention also includes isolated polynucleotides and expression vectors encoding the anti-PACAP antigen binding proteins described herein as well as host cells, such as CHO cells, comprising the encoding polynucleotides and expression vectors.

In another embodiment, the present invention provides a method for producing the antigen binding proteins, including monoclonal antibodies and binding fragments thereof, described herein. In one embodiment, the method comprises culturing a host cell comprising an expression vector encoding the antigen binding protein under conditions that allow expression of the antigen binding protein, and recovering the antigen binding protein from the culture medium or host cell.

The antigen binding proteins described herein can be used in the manufacture of a pharmaceutical composition or medicament for the treatment or prevention of conditions associated with PACAP biological activity, such as headache, migraine, and chronic pain. Thus, the present invention also provides a pharmaceutical composition comprising an antigen binding protein and a pharmaceutically acceptable diluent, excipient or carrier. In some embodiments, the antigen binding protein specifically binds to a C-terminal domain of PACAP38, e.g. at an epitope within amino acids 28 to 38 of SEQ ID NO: 1, at an epitope within amino acids 28 to 37 of SEQ ID NO: 1, or at an epitope within amino acids 34 to 38 of SEQ ID NO: 1. In other embodiments, the antigen binding protein specifically binds to an N-terminal domain of PACAP38, e.g., at an epitope within amino acids 1 to 13 of SEQ ID NO: 1. In still other embodiments, the antigen binding protein specifically binds to human PACAP38 at an epitope within amino acids 6 to 20 of SEQ ID NO: 1 or at an epitope within amino acids 14 to 27 of SEQ ID NO: 1.

In some embodiments, the present invention provides a method for treating or preventing a headache condition in a patient in need thereof comprising administering to the patient an effective amount of an antigen binding protein described herein. In certain embodiments, the antigen binding protein specifically binds to a C-terminal domain of PACAP38, e.g. at an epitope within amino acids 28 to 38 of SEQ ID NO: 1, at an epitope within amino acids 28 to 37 of SEQ ID NO: 1, or at an epitope within amino acids 34 to 38 of SEQ ID NO: 1. In other embodiments, the antigen binding protein specifically binds to an N-terminal domain of PACAP38, e.g., at an epitope within amino acids 1 to 13 of SEQ ID NO: 1. In still other embodiments, the antigen binding protein specifically binds to human PACAP38 at an epitope within amino acids 6 to 20 of SEQ ID NO: 1 or at an epitope within amino acids 14 to 27 of SEQ ID NO: 1. In some embodiments, the headache condition to be treated or prevented with the methods of the invention is migraine. The migraine can be episodic migraine or chronic migraine. In other embodiments, the headache condition to be treated or prevented with the methods of the invention is cluster headache. In particular embodiments, the methods provide prophylactic treatment for these conditions. The antigen binding protein may be administered to the patient by a parenteral route of administration, such as subcutaneous or intravenous administration.

The use of the anti-PACAP antigen binding proteins in any of the methods disclosed herein or for preparation of medicaments for administration according to any of the methods disclosed herein is specifically contemplated. For instance, the present invention includes an anti-PACAP antigen binding protein, such as anti-PACAP monoclonal antibody or binding fragment thereof, for use in a method for treating or preventing a headache condition in a patient in need thereof. The headache condition includes migraine (episodic and chronic migraine) and cluster headache.

The present invention also includes the use of an anti-PACAP antigen binding protein, such as anti-PACAP monoclonal antibody or binding fragment thereof, in the preparation of a medicament for treating or preventing a headache condition in a patient in need thereof. The headache condition includes migraine (episodic and chronic migraine) and cluster headache.

DETAILED DESCRIPTION

Figure 1:
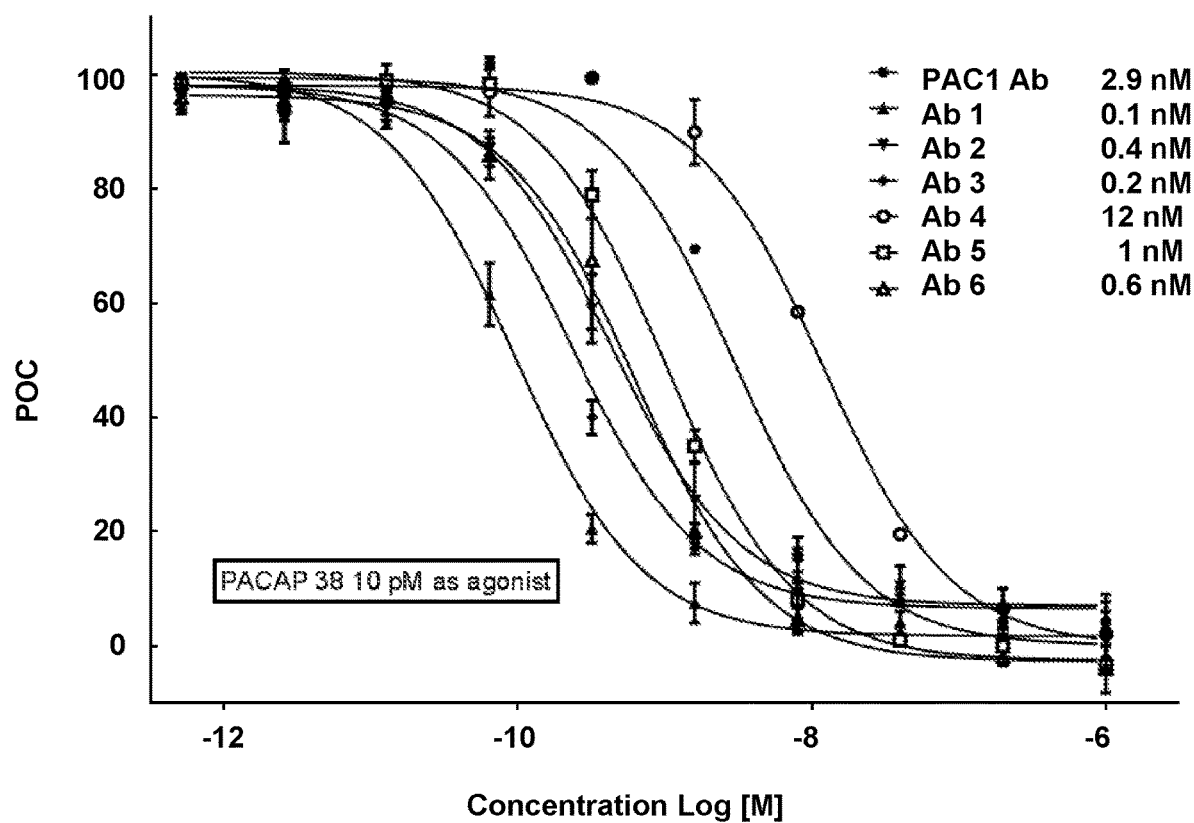
FIG. 1 depicts dose-response curves for monoclonal anti-PACAP antibodies (Ab1, Ab2, Ab3, Ab4, Ab5, and Ab6) and a monoclonal anti-PAC1 receptor antibody (PAC1 Ab) for inhibition of PACAP38-induced activation of the human PAC1 receptor. The IC50 values for each of the antibodies are listed to the right of the antibody designation in the legend.

The present invention relates to isolated antigen binding proteins that specifically bind to human pituitary adenylate cyclase-activating polypeptide (PACAP). In humans, PACAP is produced from a 176 amino acid precursor protein (Genbank accession no. NP_001108.2) encoded by the ADCYAP1 gene. There are two naturally-occurring isoforms of PACAP: a 38-amino acid peptide (PACAP38) and a 27-amino acid peptide (PACAP27), both of which are amidated at their carboxy termini (Vaudry et al., Pharmacol. Rev., Vol. 52: 269-324, 2000). PACAP38 corresponds to amino acids 132-169 of the precursor protein and its sequence is HSDGIFTDSYSRYRKQMAVKKYLAAVLGKRYKQRVKNK (SEQ ID NO: 1). PACAP27 is an amino-terminal fragment of PACAP38 and corresponds to amino acids 132-158 of the precursor protein. The sequence of PACAP27 is HSDGIFTDSYSRYRKQMAVKKYLAAVL (SEQ ID NO: 2). Unless indicated otherwise by the context, the term "PACAP," as used herein, refers to both PACAP38 and PACAP27.

As used herein, the term "antigen binding protein" refers to a protein that specifically binds to one or more target antigens. An antigen binding protein can include an antibody and binding fragments thereof. An "antigen binding fragment," used interchangeably herein with "binding fragment" or "fragment," is a portion of an antibody that lacks at least some of the amino acids present in a full-length heavy chain and/or light chain, but which is still capable of specifically binding to an antigen. An antigen binding fragment includes, but is not limited to, a single-chain variable fragment (scFv), a nanobody (e.g. VH domain of camelid heavy chain antibodies; VHH fragment, see Cortez-Retamozo et al., Cancer Research, Vol. 64:2853-57, 2004), a Fab fragment, a Fab' fragment, a F(ab')$_2$ fragment, a Fv fragment, a Fd fragment, and a complementarity determining region (CDR) fragment, and can be derived from any mammalian source, such as human, mouse, rat, rabbit, or camelid. Antigen binding fragments may compete for binding of a target antigen with an intact antibody and the fragments may be produced by the modification of intact antibodies (e.g. enzymatic or chemical cleavage) or synthesized de novo using recombinant DNA technologies or peptide synthesis.

An antigen binding protein can also include a protein comprising one or more antigen binding fragments incorporated into a single polypeptide chain or into multiple polypeptide chains. For instance, antigen binding proteins can include, but are not limited to, a diabody (see, e.g., EP 404,097; WO 93/11161; and Hollinger et al., Proc. Natl. Acad. Sci. USA, Vol. 90:6444-6448, 1993); an intrabody; a domain antibody (single VL or VH domain or two or more VH domains joined by a peptide linker; see Ward et al., Nature, Vol. 341:544-546, 1989); a maxibody (2 scFvs fused to Fc region, see Fredericks et al., Protein Engineering, Design & Selection, Vol. 17:95-106, 2004 and Powers et al., Journal of Immunological Methods, Vol. 251:123-135, 2001); a triabody; a tetrabody; a minibody (scFv fused to CH3 domain; see Olafsen et al., Protein Eng Des Sel., Vol. 17:315-23, 2004); a peptibody (one or more peptides attached to an Fc region, see WO 00/24782); a linear antibody (a pair of tandem Fd segments (VH-CH1-VH-CH1) which, together with complementary light chain polypeptides, form a pair of antigen binding regions, see Zapata et al., Protein Eng., Vol. 8:1057-1062, 1995); a small modular immunopharmaceutical (see U.S. Patent Publication No. 20030133939); and immunoglobulin fusion proteins (e.g. IgG-scFv, IgG-Fab, 2scFv-IgG, 4scFv-IgG, VH-IgG, IgG-VH, and Fab-scFv-Fc; see, e.g., Spiess el al., Mol. Immunol., Vol. 67(2 Pt A):95-106, 2015).

In certain embodiments of the invention, the antigen binding proteins specifically bind to both PACAP38 (SEQ ID NO: 1) and PACAP27 (SEQ ID NO: 2). An antigen binding protein "specifically binds" to a target antigen when it has a significantly higher binding affinity for, and consequently is capable of distinguishing, that antigen compared to its affinity for other unrelated proteins, under similar binding assay conditions. Antigen binding proteins that specifically bind an antigen may have an equilibrium dissociation constant ($K_D$)≤$1 \times 10^{-6}$ M. The antigen binding protein specifically binds antigen with "high affinity" when the $K_D$ is ≤$1 \times 10^{-8}$ M. In one embodiment, the antigen binding proteins of the invention bind to human PACAP with a $K_D$ of ≤$5 \times 10^{-7}$ M. In another embodiment, the antigen binding proteins of the invention bind to human PACAP with a $K_D$ of ≤$1 \times 10^{-7}$ M. In yet another embodiment, the antigen binding proteins of the invention bind to human PACAP with a $K_D$ of ≤$5 \times 10^{-8}$ M. In another embodiment, the antigen binding proteins of the invention bind to human PACAP with a $K_D$ of ≤$1 \times 10^{-8}$ M. In certain embodiments, the antigen binding proteins of the invention bind to human PACAP with a $K_D$ of ≤$5 \times 10^{-9}$ M. In other embodiments, the antigen binding proteins of the invention bind to human PACAP with a $K_D$ of ≤$1 \times 10^{-9}$ M. In one particular embodiment, the antigen binding proteins of the invention bind to human PACAP with a $K_D$ of ≤$5 \times 10^{-10}$ M. In another particular embodiment, the antigen binding proteins of the invention bind to PACAP with a $K_D$ of ≤$1 \times 10^{-10}$ M.

Affinity is determined using a variety of techniques, an example of which is an affinity ELISA assay. In various embodiments, affinity is determined by a surface plasmon resonance assay (e.g., BIAcore®-based assay). Using this methodology, the association rate constant ($k_a$ in $M^{-1}s^{-1}$) and the dissociation rate constant ($k_d$ in $s^{-1}$) can be measured. The equilibrium dissociation constant ($K_D$ in M) can then be calculated from the ratio of the kinetic rate constants ($k_d/k_a$). In some embodiments, affinity is determined by a kinetic method, such as a Kinetic Exclusion Assay (KinExA) as described in Rathanaswami et al. Analytical Biochemistry, Vol. 373:52-60, 2008. Using a KinExA assay, the equilibrium dissociation constant ($K_D$ in M) and the association rate constant ($k_a$ in $M^{-1}s^{-1}$) can be measured. The dissociation rate constant ($k_d$ in $s^{-1}$) can be calculated from these values ($K_D \times k_a$). In other embodiments, affinity is determined by an equilibrium/solution method. In some embodiments, the antigen binding proteins described herein exhibit desirable characteristics such as binding avidity as measured by $k_d$ (dissociation rate constant) for human PACAP of about $10^{-2}$, $10^{-3}$, $10^{-4}$, $10^{-5}$, $10^{-6}$, $10^{-7}$, $10^{-8}$, $10^{-9}$, $10^{-10}$ $s^{-1}$ or lower (lower values indicating higher binding avidity), and/or binding affinity as measured by $K_D$ (equilibrium dissociation constant) for human PACAP of about $10^{-9}$, $10^{-10}$, $10^{-11}$, $10^{-12}$, $10^{-13}$, $10^{-14}$, $10^{-15}$, $10^{-16}$ M or lower (lower values indicating higher binding affinity).

Preferably, the antigen binding proteins do not significantly bind or cross react with other members of the VIP/secretin/glucagon superfamily, such as human VIP or human secretin. As used herein, an antigen binding protein does "not significantly bind" to a target antigen when it has a binding affinity for that antigen that is comparable to its affinity for other unrelated proteins, under similar binding assay conditions. Antigen binding proteins that do not significantly bind to a target antigen may also include those proteins that do not generate a statistically different signal than a negative control in an affinity assay, such as those described herein, for the target antigen. By way of example, an antigen binding protein, which produces a signal value in an ELISA- or a BIAcore®-based assay for determining binding to human PACAP that is not statistically different from the signal value produced with a negative control (e.g. buffer solution without antigen binding protein), would be considered to not significantly bind to human PACAP. Antigen binding proteins that do not significantly bind an antigen may have an equilibrium dissociation constant ($K_D$) for that antigen greater than $1 \times 10^{-6}$ M, greater than $1 \times 10^{-5}$ M, greater than $1 \times 10^{-4}$ M, or greater than $1 \times 10^{-3}$ M.

In some embodiments, the antigen binding proteins of the invention do not significantly bind to human VIP (HSDAVFTDNYTRLRKQMAVKKYLNSILN; SEQ ID NO: 3). Thus, in one embodiment, the antigen binding proteins do not significantly bind to a polypeptide consisting of the sequence of SEQ ID NO: 3. In related embodiments, the antigen binding proteins of the invention do not significantly bind to human secretin (HSDGTFTSELSRLREGARLQRLLQGLV; SEQ ID NO: 62). Accordingly, in another embodiment, the antigen binding proteins do not significantly bind to a polypeptide consisting of the sequence of SEQ ID NO: 62.

The antigen binding proteins may, in some embodiments, bind to a particular region or epitope of PACAP. As used herein, an "epitope" refers to any determinant capable of being specifically bound by an antibody or fragment thereof. An epitope can be contiguous or non-contiguous (e.g., (i) in a single-chain polypeptide, amino acid residues that are not contiguous to one another in the polypeptide sequence but that within in context of the molecule are bound by the antibody or functional fragment, or (ii) in a multimeric protein, e.g., comprising two or more individual components, amino acid residues present on two or more of the individual components, but that within the context of the multimeric protein are bound by the antibody or functional fragment). In some embodiments, the antigen binding proteins bind to PACAP at an epitope within an N-terminal domain (e.g. amino acids 1-13 of SEQ ID NO: 1). In related embodiments, the antigen binding proteins specifically bind to a polypeptide consisting of the sequence of SEQ ID NO: 5. As shown in the Examples herein, these N-terminal PACAP binding proteins specifically bind to both PACAP38 and PACAP27 and inhibit activation of the PAC1 receptor by both ligands.

In certain embodiments, the antigen binding proteins bind to PACAP at an epitope within a central region of the PACAP27 and PACAP38 proteins. For instance, in one embodiment, the antigen binding protein binds to PACAP at an epitope within amino acids 6 to 20 of SEQ ID NO: 1. In such an embodiment, the antigen binding protein specifically binds to a polypeptide consisting of the sequence of SEQ ID NO: 122. In another embodiment, the antigen binding protein binds to PACAP at an epitope within amino acids 14 to 27 of SEQ ID NO: 1. In these and other embodiments, the antigen binding protein specifically binds to a polypeptide consisting of the sequence of SEQ ID NO: 117 and a polypeptide consisting of the sequence of SEQ ID NO: 118, but does not significantly bind to a polypeptide consisting of the sequence of SEQ ID NO: 116. In still another embodiment, the antigen binding protein specifically binds to a polypeptide consisting of the sequence of SEQ ID NO: 117 and a polypeptide consisting of the sequence of SEQ ID NO: 118, but does not significantly bind to a polypeptide consisting of the sequence of SEQ ID NO: 116 and a polypeptide consisting of the sequence of SEQ ID NO: 124.

In other embodiments, the antigen binding proteins bind to a particular region or epitope of PACAP such that PACAP38 is preferentially bound from PACAP27. For instance, in some embodiments, the antigen binding proteins bind to PACAP38 at an epitope within a C-terminal domain (e.g. amino acids 28-38 of SEQ ID NO: 1). In such embodiments, the antigen binding proteins may specifically bind to a polypeptide consisting of the sequence of SEQ ID NO: 4. In one embodiment, the antigen binding proteins bind to an epitope within residues 28 to 37 of PACAP38 (SEQ ID NO: 1). In another embodiment, the antigen binding proteins bind to an epitope within residues 34 to 38 of PACAP38 (SEQ ID NO: 1). In these and other embodiments, the antigen binding proteins specifically bind to PACAP38, but do not significantly bind to PACAP27. Thus, in certain embodiments, these antigen binding proteins do not significantly bind to a polypeptide consisting of the sequence of SEQ ID NO: 2. In related embodiments, the antigen binding proteins specifically bind to a polypeptide consisting of the sequence of SEQ ID NO: 4, but do not significantly bind to a polypeptide consisting of the sequence of SEQ ID NO: 5. In other embodiments, the antigen binding proteins specifically bind to a polypeptide consisting of the sequence of SEQ ID NO: 4 and/or a polypeptide consisting of the sequence of SEQ ID NO: 126. In certain embodiments, the antigen binding proteins bind to a polypeptide consisting of the sequence of SEQ ID NO: 4 with a binding affinity at least 2-fold greater than that for a polypeptide consisting of the sequence of SEQ ID NO: 115 as measured by a surface plasmon resonance assay (e.g., BIAcore®-based assay) as described herein. In other embodiments, the antigen binding proteins bind to a polypeptide consisting of the sequence of SEQ ID NO: 4 with a binding affinity at least 5-fold greater than that for a polypeptide consisting of the sequence of SEQ ID NO: 115 as measured by a surface plasmon resonance assay. In still other embodiments, the antigen binding proteins bind to a polypeptide consisting of the sequence of SEQ ID NO: 4 with a binding affinity at least 10-fold greater than that for a polypeptide consisting of the sequence of SEQ ID NO: 115 as measured by a surface plasmon resonance assay.

As further described in the Examples, these C-terminal PACAP binding proteins specifically bind to PACAP38 and potently inhibit its activation of the PAC1 receptor, but do not significantly bind PACAP27 or inhibit PACAP27's ability to activate the PAC1 receptor. The C-terminal PACAP binding proteins are more potent inhibitors of PACAP38-activation of the PAC1 receptor than the PACAP binding proteins binding to the N-terminus or central region of PACAP. See Example 2. This result is unexpected in view of the reports in the literature that the N-terminal domain of PACAP38 is essential for PAC1 receptor activation, whereas the C-terminal domain has no significant impact on the ability of PACAP38 to activate the PAC1 receptor. See, e.g., Bourgault et al., J. Med. Chem., Vol. 52: 3308-3316, 2009.

The antigen binding proteins of the invention may inhibit, interfere with, or modulate one or more biological activities of the human PAC1, VPAC1, and/or VPAC2 receptors. Biological activities of these receptors include, but are not limited to, induction of PACAP-mediated receptor signal transduction pathways, induction of vasodilation, and inhibition of vasoconstriction. In some embodiments, the antigen binding proteins of the invention inhibit binding of PACAP to the human PAC1, VPAC1, and/or VPAC2 receptors. "Inhibition of binding" occurs when an excess of antigen binding proteins reduces the quantity of human PAC1, VPAC1, and/or VPAC2 receptors bound to PACAP, or vice versa, for example, by at least about 40%, about 50%, about 60%, about 70%, about 80%, about 85%, about 90%, about 95%, about 97%, about 99% or more, for example by measuring binding in an in vitro competitive binding assay. In one embodiment, the antigen binding proteins inhibit the binding of PACAP38 and/or PACAP27 to the human PAC1 receptor. In another embodiment, the antigen binding proteins inhibit the binding of PACAP38 to the human PAC1 receptor, but do not significantly inhibit the binding of PACAP27 to the human PAC1 receptor.

In other embodiments, the antigen binding proteins of the invention inhibit PACAP-induced activation of the human PAC1, VPAC1, and/or VPAC2 receptors. Various assays for assessing activation of PAC1, VPAC1, and/or VPAC2 receptors are known in the art and include cell-based assays measuring ligand-induced calcium mobilization and cAMP production. An exemplary cell-based cAMP assay is described in Example 2. Other suitable PAC1, VPAC1, and VPAC2 receptor activation assays are described in Dickson et al., Ann. N. Y. Acad. Sci., Vol. 1070:239-42, 2006; Bourgault et al., J. Med. Chem., Vol. 52: 3308-3316, 2009; and U.S. Patent Publication No. 2011/0229423, all of which are hereby incorporated by reference in their entireties.

The inhibitory activity of the antigen binding proteins on PAC1, VPAC1, and VPAC2 receptor activation can be quantitated by calculating an IC50 in any functional assay for these receptors, such as those described above. An "IC50" is the dose/concentration required to achieve 50% inhibition of a biological or biochemical function. With radioactive ligands, IC50 is the concentration of a competing ligand that displaces 50% of the specific binding of the radioligand. The IC50 of any particular substance or antagonist can be determined by constructing a dose-response curve and examining the effect of different concentrations of the drug or antagonist on reversing agonist activity in a particular functional assay. IC50 values can be calculated for a given antagonist or drug by determining the concentration needed to inhibit half of the maximum biological response of the agonist. Thus, the IC50 value for any PACAP antigen binding protein of the invention can be calculated by determining the concentration of the antigen binding protein needed to inhibit half of the maximum biological response of the PACAP ligand (PACAP-27 or PACAP-38) in activating the human PAC1, VPAC1, or VPAC2 receptor in any functional assay, such as the cAMP assay described in the Examples. A PACAP antigen binding protein that inhibits PACAP-induced activation of a receptor is understood to be a neutralizing antigen binding protein.

In certain embodiments, the antigen binding proteins of the invention inhibit PACAP38- or PACAP27-induced activation of the human PAC1 receptor. For instance, the antigen binding proteins may inhibit PACAP-induced activation of the human PAC1 receptor with an IC50 less than about 50 nM, less than about 40 nM, less than about 30 nM, less than about 25 nM, less than about 20 nM, less than about 15 nM, less than about 10 nM, less than about 5 nM, less than about 3 nM, or less than about 1 nM as measured by a cell-based calcium mobilization assay or cAMP assay. In one particular embodiment, the antigen binding proteins of the invention inhibit PACAP38-induced activation of the human PAC1 receptor with an IC50 less than about 5 nM as measured by a cell-based cAMP assay. In another particular embodiment, the antigen binding proteins of the invention inhibit PACAP38-induced activation of the human PAC1 receptor with an IC50 less than about 1 nM as measured by a cell-based cAMP assay. In still another particular embodiment, the antigen binding proteins of the invention inhibit PACAP38-induced activation of the human PAC1 receptor with an IC50 less than about 500 pM (e.g., less than about 400 pM, less than about 300 pM, less than about 200 pM, or less than about 100 pM), as measured by a cell-based cAMP assay. In some embodiments, the antigen binding proteins of the invention inhibit PACAP38-induced activation of the human PAC1 receptor with an IC50 between about 0.1 nM and about 1 nM as measured by a cell-based cAMP assay. In other embodiments, the antigen binding proteins of the invention inhibit PACAP38-induced activation of the human PAC1 receptor with an IC50 between about 100 pM and about 500 pM as measured by a cell-based cAMP assay. Thus, in certain embodiments, the PACAP antigen binding proteins of the invention are neutralizing antigen binding proteins of PACAP38.

In some embodiments, the antigen binding proteins inhibit PACAP38-induced activation of the human PAC1, VPAC1, or VPAC2 receptor, but do not significantly inhibit PACAP27-induced activation of these receptors. As used herein, an antigen binding protein would "not significantly inhibit" the activation of a receptor or binding of a ligand to its receptor if there is no statistical difference between ligand-induced receptor activation or ligand binding to the receptor in the presence or absence of the antigen binding protein. For example, if the amount of cAMP production induced by PACAP in cells expressing human PAC1 receptor in the presence of an antigen binding protein is not statistically different than the amount produced in the absence of the antigen binding protein, then the antigen binding protein would be considered to not significantly inhibit PACAP-induced activation of the human PAC1 receptor. Similarly, if the amount of PACAP bound to the human PAC1 receptor in the presence of excess antigen binding protein is not statistically different than the amount of PACAP bound to the receptor in the absence of the antigen binding protein, then the antigen binding protein would be considered to not significantly inhibit the binding of PACAP to the human PAC1 receptor. In certain embodiments, the antigen binding proteins of the invention inhibit PACAP38-induced activation of the human PAC1 receptor, but do not significantly inhibit PACAP27-induced activation of the human PAC1 receptor. Thus, in these embodiments, the antigen binding proteins are neutralizing binding proteins of PACAP38, but not PACAP27. In such embodiments, the antigen binding proteins may bind to PACAP38 at an epitope within the C-terminal domain (e.g., within amino acids 28-38 of SEQ ID NO: 1).

The antigen binding proteins of the invention may comprise one or more complementarity determining regions (CDR) from the light and heavy chain variable regions of antibodies that specifically bind to human PACAP as described herein. The term "CDR" refers to the complementarity determining region (also termed "minimal recognition units" or "hypervariable region") within antibody variable sequences. There are three heavy chain variable region CDRs (CDRH1, CDRH2 and CDRH3) and three light chain variable region CDRs (CDRL1, CDRL2 and CDRL3). The term "CDR region" as used herein refers to a group of three CDRs that occur in a single variable region (i.e. the three light chain CDRs or the three heavy chain CDRs). The CDRs in each of the two chains typically are aligned by the framework regions (FRs) to form a structure that binds specifically with a specific epitope or domain on the target protein (e.g., human PACAP). From N-terminus to C-terminus, naturally-occurring light and heavy chain variable regions both typically conform with the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, Md.), or Chothia & Lesk, 1987, *J. Mol. Biol.* 196:901-917; Chothia et al., 1989, Nature 342: 878-883. Complementarity determining regions (CDRs) and framework regions (FR) of a given antibody may be identified using this system. In some embodiments, the anti-PACAP antibody or binding fragment thereof comprises at least one heavy chain variable region comprising a CDRH1, CDRH2, and CDRH3 and at least one light chain variable region comprising a CDRL1, CDRL2, and CDRL3. Specific light and heavy chain CDRs are listed in Table 1.

TABLE 1

Exemplary Light and Heavy Chain CDR Amino Acid Sequences

| Antibody No. | | Designation | Amino Acid Sequence | SEQ ID NO: |
|---|---|---|---|---|
| Light Chain CDRs | | | | |
| mAb1; | mAb3 | CDRL1-1 | RASEDIESFLA | 30 |
| mAb2 | | CDRL1-2 | QASESIDSDLS | 31 |
| mAb4 | | CDRL1-3 | QASQSIRNELS | 32 |
| mAb5 | | CDRL1-4 | QSSESVYNNNYLS | 33 |
| mAb6 | | CDRL1-5 | QASQSVYNNKNLA | 34 |
| mAb1; | mAb3 | CDRL2-1 | RTSTLES | 35 |
| mAb2 | | CDRL2-2 | RTFTLES | 36 |
| mAb4 | | CDRL2-3 | KASTLAS | 37 |
| mAb5 | | CDRL2-4 | GASTLAS | 38 |
| mAb6 | | CDRL2-5 | FSSTLAS | 39 |
| mAb1; | mAb3 | CDRL3-1 | QCTDGSSSSSSYGWDA | 40 |
| mAb2 | | CDRL3-2 | QCTDGSSISGSYGWDA | 41 |
| mAb4 | | CDRL3-3 | QNNYGTRRNNYVFP | 42 |
| mAb5 | | CDRL3-4 | LGDYIIIENI | 43 |
| mAb6 | | CDRL3-5 | LGEFGSIWA | 44 |

TABLE 1-continued

Exemplary Light and Heavy Chain CDR Amino Acid Sequences

| Antibody No. | | Designation | Amino Acid Sequence | SEQ ID NO: |
|---|---|---|---|---|
| Heavy Chain CDRs | | | | |
| mAb 1 | | CDRH1-1 | NDYMC | 45 |
| mAb2 | | CDRH1-2 | SSSYMC | 46 |
| mAb3 | | CDRH1-3 | SNYYMC | 47 |
| mAb4 | | CDRH1-4 | SYAMI | 48 |
| mAb5 | | CDRH1-5 | TYNMC | 49 |
| mAb6 | | CDRH1-6 | DNYLC | 50 |
| mAb1; | mAb3 | CDRH2-1 | CIFTGSSGSTYYASWAKG | 51 |
| mAb2 | | CDRH2-2 | CIFTGSSGNTYYATWAQG | 52 |
| mAb4 | | CDRH2-3 | FIDAGDGNTYYASWAKG | 53 |
| mAb5 | | CDRH2-4 | FINSDDSAYYASWAKG | 54 |
| mAb6 | | CDRH2-5 | CIGIVLRSTGATYYASWAEG | 55 |
| mAb1 | | CDRH3-1 | DRAISVLGYFYAAYFFDF | 56 |
| mAb2 | | CDRH3-2 | DRAYFLVGYFYATYYFDL | 57 |
| mAb3 | | CDRH3-3 | DRALSVVGYFYAAYYFDF | 58 |
| mAb4 | | CDRH3-4 | GDPGWSNGFAL | 59 |
| mAb5 | | CDRH3-5 | YDWDYYYSRLDL | 60 |
| mAb6 | | CDRH3-6 | DLGYGGPL | 61 |

The anti-PACAP antigen binding proteins of the invention may comprise one or more of the light chain CDRs (i.e. CDRLs) and/or heavy chain CDRs (i.e. CDRHs) presented in Table 1. For instance, in certain embodiments, the anti-PACAP antigen binding proteins comprise one or more light chain CDRs selected from (i) a CDRL1 selected from SEQ ID NOs: 30 to 34, (ii) a CDRL2 selected from SEQ ID NOs: 35 to 39, and (iii) a CDRL3 selected from SEQ ID NOs: 40 to 44, and (iv) a CDRL of (i), (ii) and (iii) that contains one or more, e.g., one, two, three, four or more amino acid substitutions (e.g., conservative amino acid substitutions), deletions or insertions of no more than five, four, three, two, or one amino acids. In these and other embodiments, the anti-PACAP antigen binding proteins comprise one or more heavy chain CDRs selected from (i) a CDRH1 selected from SEQ ID NOs: 45 to 50, (ii) a CDRH2 selected from SEQ ID NOs: 51 to 55, and (iii) a CDRH3 selected from SEQ ID NOs: 56 to 61, and (iv) a CDRH of (i), (ii) and (iii) that contains one or more, e.g., one, two, three, four or more amino acid substitutions (e.g., conservative amino acid substitutions), deletions or insertions of no more than five, four, three, two, or one amino acids amino acids.

In certain embodiments, the anti-PACAP antigen binding proteins may comprise 1, 2, 3, 4, 5, or 6 variant forms of the CDRs listed in Table 1, each having at least 80%, 85%, 90% or 95% sequence identity to a CDR sequence listed in Table 1. In some embodiments, the anti-PACAP antigen binding proteins include 1, 2, 3, 4, 5, or 6 of the CDRs listed in Table 1, each differing by no more than 1, 2, 3, 4 or 5 amino acids from the CDRs listed in this table.

In particular embodiments, the anti-PACAP antigen binding proteins of the invention comprise a light chain variable region comprising a CDRL1, a CDRL2, and a CDRL3, wherein: (a) CDRL1, CDRL2, and CDRL3 have the sequence of SEQ ID NOs: 30, 35, and 40, respectively; (b) CDRL1, CDRL2, and CDRL3 have the sequence of SEQ ID NOs: 31, 36, and 41, respectively; (c) CDRL1, CDRL2, and CDRL3 have the sequence of SEQ ID NOs: 30, 35, and 40, respectively; (d) CDRL1, CDRL2, and CDRL3 have the sequence of SEQ ID NOs: 32, 37, and 42, respectively; (e) CDRL1, CDRL2, and CDRL3 have the sequence of SEQ ID NOs: 33, 38, and 43, respectively; or (f) CDRL1, CDRL2, and CDRL3 have the sequence of SEQ ID NOs: 34, 39, and 44, respectively.

In other particular embodiments, the anti-PACAP antigen binding proteins of the invention comprise a heavy chain variable region comprising a CDRH1, a CDRH2, and a CDRH3, wherein: (a) CDRH1, CDRH2, and CDRH3 have the sequence of SEQ ID NOs: 45, 51, and 56, respectively; (b) CDRH1, CDRH2, and CDRH3 have the sequence of SEQ ID NOs: 46, 52, and 57, respectively; (c) CDRH1, CDRH2, and CDRH3 have the sequence of SEQ ID NOs: 47, 51, and 58, respectively; (d) CDRH1, CDRH2, and CDRH3 have the sequence of SEQ ID NOs: 48, 53, and 59, respectively; (e) CDRH1, CDRH2, and CDRH3 have the sequence of SEQ ID NOs: 49, 54, and 60, respectively; or (f) CDRH1, CDRH2, and CDRH3 have the sequence of SEQ ID NOs: 50, 55, and 61, respectively.

In certain embodiments, the anti-PACAP antigen binding proteins of the invention comprise a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 30, 35, and 40, respectively, and CDRH1, CDRH2, and CDRH3 have the sequence of SEQ ID NOs: 45, 51, and 56, respectively;

(b) CDRL1, CDRL2, and CDRL3 have the sequence of SEQ ID NOs: 31, 36, and 41, respectively, and CDRH1, CDRH2, and CDRH3 have the sequence of SEQ ID NOs: 46, 52, and 57, respectively;

(c) CDRL1, CDRL2, and CDRL3 have the sequence of SEQ ID NOs: 30, 35, and 40, respectively, and CDRH1, CDRH2, and CDRH3 have the sequence of SEQ ID NOs: 47, 51, and 58, respectively;

(d) CDRL1, CDRL2, and CDRL3 have the sequence of SEQ ID NOs: 32, 37, and 42, respectively, and CDRH1, CDRH2, and CDRH3 have the sequence of SEQ ID NOs: 48, 53, and 59, respectively;

(e) CDRL1, CDRL2, and CDRL3 have the sequence of SEQ ID NOs: 33, 38, and 43, respectively, and CDRH1, CDRH2, and CDRH3 have the sequence of SEQ ID NOs: 49, 54, and 60, respectively; or (f) CDRL1, CDRL2, and CDRL3 have the sequence of SEQ ID NOs: 34, 39, and 44, respectively, and CDRH1, CDRH2, and CDRH3 have the sequence of SEQ ID NOs: 50, 55, and 61, respectively.

In some embodiments, the anti-PACAP antigen binding proteins specifically bind to PACAP38 at an epitope in the C-terminal domain (e.g., within amino acids 28-38 of SEQ ID NO: 1). Such C-terminal anti-PACAP antigen binding proteins of the invention may comprise a light chain variable region comprising a CDRL1, a CDRL2, and a CDRL3, wherein CDRL1 has the sequence of SEQ ID NO: 30 or 31, CDRL2 has the sequence of SEQ ID NO: 35 or 36, and CDRL3 has the sequence of SEQ ID NO: 40 or 41. In related embodiments, the C-terminal anti-PACAP antigen binding proteins may comprise a heavy chain variable region comprising a CDRH1, a CDRH2, and a CDRH3, wherein CDRH1 has a sequence selected from SEQ ID NOs: 45 to 47, CDRH2 has the sequence of SEQ ID NO: 51 or 52, and CDRH3 has a sequence selected from SEQ ID NOs: 56 to 58. In one embodiment, a C-terminal anti-PACAP antigen binding protein comprises a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 30, 35, and 40, respectively, and CDRH1, CDRH2, and CDRH3 have the sequence of SEQ ID NOs: 45, 51, and 56, respectively;

(b) CDRL1, CDRL2, and CDRL3 have the sequence of SEQ ID NOs: 31, 36, and 41, respectively, and CDRH1, CDRH2, and CDRH3 have the sequence of SEQ ID NOs: 46, 52, and 57, respectively; or (c) CDRL1, CDRL2, and CDRL3 have the sequence of SEQ ID NOs: 30, 35, and 40, respectively, and CDRH1, CDRH2, and CDRH3 have the sequence of SEQ ID NOs: 47, 51, and 58, respectively.

In some embodiments, the anti-PACAP antigen binding proteins specifically bind to PACAP38 at an epitope in the N-terminal domain (e.g., within amino acids 1-13 of SEQ ID NO: 1). Such N-terminal anti-PACAP antigen binding proteins of the invention may comprise a light chain variable region comprising a CDRL1, a CDRL2, and a CDRL3, wherein CDRL1 has the sequence of SEQ ID NOs: 32 to 34, CDRL2 has the sequence of SEQ ID NOs: 37 to 39, and CDRL3 has the sequence of SEQ ID NOs: 42 to 44. In related embodiments, the N-terminal anti-PACAP antigen binding proteins may comprise a heavy chain variable region comprising a CDRH1, a CDRH2, and a CDRH3, wherein CDRH1 has a sequence selected from SEQ ID NOs: 48 to 50, CDRH2 has the sequence of SEQ ID NOs: 53 to 55, and CDRH3 has a sequence selected from SEQ ID NOs: 59 to 61. In one embodiment, an N-terminal anti-PACAP antigen binding protein comprises a light chain variable region comprising a CDRL1, a CDRL2, and a CDRL3 and a heavy chain variable region comprising a CDRH1, a CDRH2, and a CDRH3, wherein:

(a) CDRL1, CDRL2, and CDRL3 have the sequence of SEQ ID NOs: 32, 37, and 42, respectively, and CDRH1, CDRH2, and CDRH3 have the sequence of SEQ ID NOs: 48, 53, and 59, respectively;

(b) CDRL1, CDRL2, and CDRL3 have the sequence of SEQ ID NOs: 33, 38, and 43, respectively, and CDRH1, CDRH2, and CDRH3 have the sequence of SEQ ID NOs: 49, 54, and 60, respectively, or (c) CDRL1, CDRL2, and CDRL3 have the sequence of SEQ ID NOs: 34, 39, and 44, respectively, and CDRH1, CDRH2, and CDRH3 have the sequence of SEQ ID NOs: 50, 55, and 61, respectively.

In particular embodiments, the antigen binding proteins of the invention comprise an immunoglobulin heavy chain variable region (VH) and an immunoglobulin light chain variable region (VL) from an antibody that specifically binds to human PACAP, such as the antibodies described herein. The "variable region," used interchangeably herein with "variable domain" (variable region of a light chain (VL), variable region of a heavy chain (VH)), refers to the region in each of the light and heavy immunoglobulin chains which is involved directly in binding the antibody to the antigen. As discussed above, the regions of variable light and heavy chains have the same general structure and each region comprises four framework (FR) regions, the sequences of which are widely conserved, connected by three CDRs. The framework regions adopt a beta-sheet conformation and the CDRs may form loops connecting the beta-sheet structure. The CDRs in each chain are held in their three-dimensional structure by the framework regions and form, together with the CDRs from the other chain, the antigen binding site.

Thus, in some embodiments, the anti-PACAP antigen binding proteins of the invention may comprise a light chain variable region selected from LV-01, LV-02, LV-03, LV-04, LV-05, or LV-06, and/or a heavy chain variable region selected from HV-01, HV-02, HV-03, HV-04, HV-05, or HV-06, as shown in Table 2 below, and binding fragments, derivatives, muteins and variants of these light chain and heavy chain variable regions.

TABLE 2

Exemplary Light and Heavy Chain Variable Region Amino Acid Sequences

| Antibody No. | Designation | Amino Acid Sequence | SEQ ID NO: |
|---|---|---|---|
| Light Chain Variable Regions | | | |
| mAb1 | LV-01 | ADVVMTQTPSPVSAAVGGTVTINCRASEDIESFLAWYQQKPGQPPKLLISRTSTLESGVSSRFKGSGSGTEFILTISDLECADAATYYCQCTDGSSSSSSYGWDAFGGGTEVVVKG | 18 |
| mAb2 | LV-02 | ADVVMTQTPSPVSAQVGGTVTINCQASESIDSDLSWYQQKPGQPPKLLIYRTFTLESGVPSRFKGSGSGTDYTLTISDLECADAAIYYCQCTDGSSISGSYGWDAFGGGTEVVVKG | 20 |
| mAb3 | LV-03 | ADVVMTQTPSPVSAAVGGTVTINCRASEDIESFLAWYQQKPGQPPKLLMSRTSTLESGVPSRFKGSGSGTEFTLTISDLECADAATYYCQCTDGSSSSSSYGWDAFGGGTEVVVKG | 22 |
| mAb4 | LV-04 | ADIVMTQTPASVSGAVGGTVTIKCQASQSIRNELSWYQQKPGQPPKLLIYKASTLASGVPSRFSGSGFGTEFTLTISGVQCDDAATYYCQNNYGTRRNNYVFPFGGGTEVVVKG | 24 |
| mAb5 | LV-05 | ADIVLTQTPASVSAAVGGTVSISCQSSESVYNNNYLSWFQQKPGQPPKLLIYGASTLASGVPSRFEGSGSGTQFTLTISDVQCDDAATYYCLGDYIIIENIFGGGTEVVVKG | 26 |
| mAb6 | LV-06 | AQVLTQTPASVSAAVGGTVTINCQASQSVYNNKNLAWYQQKPGQPPKLLIYFSSTLASGVPSRFRGSGSGTQFTLTISGVQCGDAATYYCLGEFGSIWAFGGGTEVVVKG | 28 |
| Heavy Chain Variable Regions | | | |
| mAb1 | HV-01 | QSLEESGGDLVKPGASLTLTCKASGIAFSNDYMCWVRQAPGKGLEWIACIFTGSSGSTYYASWAKGRFTISKTSSTTVTLQMTSLTAADTATYFCARDRAISVLGYFYAAYFFDFWGPGTLVTVSS | 19 |
| mAb2 | HV-02 | QSLEESGGGLVQPEGSLTLTCTASGFSFNSSSYMCWVRQAPGKGLEWIGCIFTGSSGNTYYATWAQGRFTISKTSTTVTLEMTSLTAADTATYFCARDRAYFLVGYFYATYYFDLWGPGTLVTVSS | 21 |
| mAb3 | HV-03 | QSLEESGGGLVQPGASLTLTCTASGFSFSSNYYMCWVRQAPGKGLEWIACIFTGSSGSTYYASWAKGRFTISKTSSTTVTLHVTSLTAADTATYFCARDRALSVVGYFYAAYYFDFWGPGTLVTVSS | 23 |
| mAb4 | HV-04 | QSVEESGGRLVTPGTPLTLTCTASGIDLSSYAMIWVRQAPGEGLEYIGFIDAGDGNTYYASWAKGRFTISKTSTTVDLKITSPTTEDTATYFCARGDPGWSNGFALWGQGTLVTVSS | 25 |
| mAb5 | HV-05 | QSVEESGGRLVTPGTPLTLTCTVSGFSLSTYNMCWVRQAPGKGLEWVGFINSDDSAYYASWAKGRFTFSKTSTTVDLKIASPTTEDTATYFCARYDWDYYYSRLDLWGPGTLVTVSS | 27 |
| mAb6 | HV-06 | QLEESGGGLVQPGASLTLTCTTSGFSLSDNYLCWVRQAPGRGLEWVACIGIVLRSTGATYYASWAEGRFTISKTSPTTVTLEMTSLTAADTATYFCALDLGYGGPLWGPGTLVTVSS | 29 |

Each of the light chain variable regions listed in Table 2 may be combined with any of the heavy chain variable regions shown in Table 2 to form an anti-PACAP binding domain of the antigen binding proteins of the invention. Examples of such combinations include, but are not limited to: LV-01 and HV-01; LV-02 and HV-02; LV-03 and HV-03; LV-04 and HV-04; LV-05 and HV-05; LV-06 and HV-06; LV-01 and HV-02; and LV-02 and HV-01. In certain embodiments, the anti-PACAP antigen binding proteins of the invention comprise: (a) LV-01 (SEQ ID NO: 18) and HV-01 (SEQ ID NO: 19); (b) LV-02 (SEQ ID NO: 20) and HV-02 (SEQ ID NO: 21); (c) LV-03 (SEQ ID NO: 22) and HV-03 (SEQ ID NO: 23); (d) LV-04 (SEQ ID NO: 24) and HV-04 (SEQ ID NO: 25); (e) LV-05 (SEQ ID NO: 26) and HV-05

(SEQ ID NO: 27); or (f) LV-06 (SEQ ID NO: 28) and HV-06 (SEQ ID NO: 29). In some embodiments, the anti-PACAP antigen binding proteins of the invention comprise: (a) LV-01 (SEQ ID NO: 18) and HV-01 (SEQ ID NO: 19); (b) LV-02 (SEQ ID NO: 20) and HV-02 (SEQ ID NO: 21), or (c) LV-03 (SEQ ID NO: 22) and HV-03 (SEQ ID NO: 23). In such embodiments, the anti-PACAP antigen binding proteins bind to an epitope within a C-terminal domain of PACAP38, such as an epitope within amino acids 28 to 38 of SEQ ID NO: 1.

In some embodiments, the anti-PACAP antigen binding proteins comprise a light chain variable region comprising a sequence of contiguous amino acids that differs from the sequence of a light chain variable region in Table 2, i.e. a VL selected from LV-01, LV-02, LV-03, LV-04, LV-05, or LV-06, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The light chain variable region in some anti-PACAP antigen binding proteins comprises a sequence of amino acids that has at least 70%, at least 75%, at least 80%, at least 85%, at least 90%, at least 95%, at least 97% or at least 99% sequence identity to the amino acid sequences of SEQ ID NOs: 18, 20, 22, 24, 26, or 28 (i.e. the light chain variable regions in Table 2).

In these and other embodiments, the anti-PACAP antigen binding proteins comprise a heavy chain variable region comprising a sequence of contiguous amino acids that differs from the sequence of a heavy chain variable region in Table 2, i.e., a VH selected from HV-01, HV-02, HV-03, HV-04, HV-05, or HV-06, at only 1, 2, 3, 4, 5, 6, 7, 8, 9, 10, 11, 12, 13, 14 or 15 amino acid residues, wherein each such sequence difference is independently either a deletion, insertion or substitution of one amino acid, with the deletions, insertions and/or substitutions resulting in no more than 15 amino acid changes relative to the foregoing variable domain sequences. The heavy chain variable region in some anti-PACAP antigen binding proteins comprises a sequence of amino acids that has at least 70%, at least 75%, at least 80%, at least 85%, at least 90%, at least 95%, at least 97% or at least 99% sequence identity to the amino acid sequences of SEQ ID NOs: 19, 21, 23, 25, 27, or 29 (i.e. the heavy chain variable regions in Table 2).

The term "identity," as used herein, refers to a relationship between the sequences of two or more polypeptide molecules or two or more nucleic acid molecules, as determined by aligning and comparing the sequences. "Percent identity," as used herein, means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a predetermined portion of one or both sequences). The programs provide a default opening penalty and a default gap penalty, and a scoring matrix such as PAM 250 (a standard scoring matrix; see Dayhoff et al., in Atlas of Protein Sequence and Structure, vol. 5, supp. 3 (1978)) can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

In certain embodiments, the antigen binding proteins of the invention are antibodies or binding fragments thereof. As used herein, the term "antibody" refers to a tetrameric immunoglobulin protein comprising two light chain polypeptides (about 25 kDa each) and two heavy chain polypeptides (about 50-70 kDa each). The term "light chain" or "immunoglobulin light chain" refers to a polypeptide comprising, from amino terminus to carboxyl terminus, a single immunoglobulin light chain variable region (VL) and a single immunoglobulin light chain constant domain (CL). The immunoglobulin light chain constant domain (CL) can be a human kappa (κ) or human lambda (λ) constant domain. The term "heavy chain" or "immunoglobulin heavy chain" refers to a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4). Heavy chains are classified as mu (μ), delta (Δ), gamma (γ), alpha (a), and epsilon (e), and define the antibody's isotype as IgM, IgD, IgG, IgA, and IgE, respectively. The IgG-class and IgA-class antibodies are further divided into subclasses, namely, IgG1, IgG2, IgG3, and IgG4, and IgA1 and IgA2, respectively. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (i.e. between the light and heavy chain) and between the hinge regions of the antibody heavy chains.

The anti-PACAP antibodies of the invention can comprise any immunoglobulin constant region. The term "constant region" as used herein refers to all domains of an antibody other than the variable region. The constant region is not involved directly in binding of an antigen, but exhibits various effector functions. As described above, antibodies are divided into particular isotypes (IgA, IgD, IgE, IgG, and IgM) and subtypes (IgG1, IgG2, IgG3, IgG4, IgA1 IgA2) depending on the amino acid sequence of the constant region of their heavy chains. The light chain constant region can be, for example, a kappa- or lambda-type light chain constant region, e.g., a human kappa- or lambda-type light chain constant region, which are found in all five antibody isotypes. Examples of human immunoglobulin light chain constant region sequences are shown in the following table.

TABLE 3

Exemplary Human Immunoglobulin Light Chain Constant Regions

| Designation | SEQ ID NO: | CLDomain Amino Acid Sequence |
|---|---|---|
| CL-1 | 63 | GQPKANPTVTLFPPSSEELQANKATLVCLISDFYPG AVTVAWKADGSPVKAGVETTKPSKQSNNKYAASSYL SLTPEQWKSHRSYSCQVTHEGSTVEKTVAPTECS |
| CL-2 | 64 | GQPKAAPSVTLFPPSSEELQANKATLVCLISDFYPG AVTVAWKADSSPVKAGVETTTPSKQSNNKYAASSYL SLTPEQWKSHRSYSCQVTHEGSTVEKTVAPTECS |
| CL-3 | 65 | GQPKAAPSVTLFPPSSEELQANKATLVCLISDFYPG AVTVAWKADSSPVKAGVETTTPSKQSNNKYAASSYL SLTPEQWKSHKSYSCQVTHEGSTVEKTVAPTECS |
| CL-7 | 66 | GQPKAAPSVTLFPPSSEELQANKATLVCLVSDFYPG AVTVAWKADGSPVKVGVETTKPSKQSNNKYAASSYL SLTPEQWKSHRSYSCRVTHEGSTVEKTVAPAECS |

The heavy chain constant region of the anti-PACAP antibodies of the invention can be, for example, an alpha-, delta-, epsilon-, gamma-, or mu-type heavy chain constant region, e.g., a human alpha-, delta-, epsilon-, gamma-, or mu-type heavy chain constant region. In some embodiments, the anti-PACAP antibodies comprise a heavy chain constant region from an IgG1, IgG2, IgG3, or IgG4 immunoglobulin. In one embodiment, the anti-PACAP antibody comprises a heavy chain constant region from a human IgG1 immunoglobulin. In another embodiment, the anti-PACAP antibody comprises a heavy chain constant region from a human IgG2 immunoglobulin. Examples of human IgG1 and IgG2 heavy chain constant region sequences are shown below in Table 4.

TABLE 4

Exemplary Human Immunoglobulin Heavy Chain Constant Regions

| Ig isotype | SEQ ID NO: | Heavy Chain Constant Region Amino Acid Sequence |
|---|---|---|
| Human IgG1z | 67 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQVY TLPPSREEMTKNQVSLTCLVKGFYPSDIAVEWESNGQPENNYKTTPP VLDSDGSFFLYSKLTVDKSRWQQGNVFSCSVMHEALHNHYTQKSL SLSPGK |
| Human IgG1za | 68 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQVY TLPPSRDELTKNQVSLTCLVKGFYPSDIAVEWESNGQPENNYKTTPP VLDSDGSFFLYSKLTVDKSRWQQGNVFSCSVMHEALHNHYTQKSL SLSPGK |

TABLE 4-continued

Exemplary Human Immunoglobulin Heavy Chain Constant Regions

| Ig isotype | SEQ ID NO: | Heavy Chain Constant Region Amino Acid Sequence |
|---|---|---|
| Human IgG1f | 69 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQVY TLPPSREEMTKNQVSLTCLVKGFYPSDIAVEWESNGQPENNYKTTPP VLDSDGSFFLYSKLTVDKSRWQQGNVFSCSVMHEALHNHYTQKSL SLSPGK |
| Human IgG1fa | 70 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQVY TLPPSRDELTKNQVSLTCLVKGFYPSDIAVEWESNGQPENNYKTTPP VLDSDGSFFLYSKLTVDKSRWQQGNVFSCSVMHEALHNHYTQKSL SLSPGK |
| Human IgG2 | 71 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKCCVECPPCPAPPVAGPSVFLFPPKPKDTLMISRTPEVTCV VVDVSHEDPEVQFNWYVDGVEVHNAKTKPREEQFNSTFRVVSVLT VVHQDWLNGKEYKCKVSNKGLPAPIEKTISKTKGQPREPQVYTLPP SREEMTKNQVSLTCLVKGFYPSDIAVEWESNGQPENNYKTTPPMLD SDGSFFLYSKLTVDKSRWQQGNVFSCSVMHEALHNHYTQKSLSLSP GK |

Each of the variable regions disclosed in Table 2 may be attached to the above light and heavy chain constant regions to form complete antibody light and heavy chains, respectively. Further, each of the so generated heavy and light chain sequences may be combined to form a complete antibody structure. It should be understood that the heavy chain and light chain variable regions provided herein can also be attached to other constant domains having different sequences than the exemplary sequences listed above.

Specific examples of full-length light and heavy chains of exemplary anti-PACAP antibodies of the invention and their corresponding amino acid sequences are summarized in Table 5.

TABLE 5

Exemplary Antibody Light and Heavy Chain Amino Acid Sequences

| Antibody No. | Designation | Amino Acid Sequence | SEQ ID NO: |
|---|---|---|---|
| Light Chains | | | |
| mAb1 | LC-01 | ADVVMTQTPSPVSAAVGGTVTINCRASEDIESFLA WYQQKPGQPPKLLISRTSTLESGVSSRFKGSGSGTE FILTISDLECADAATYYCQCTDGSSSSSSYGWDAF GGGTEVVVKGDPVAPTVLLFPPSSDEVATGTVTIV CVANKYFPDVTVTWEVDGTTQTTGIENSKTPQNS ADCTYNLSSTLTLTSTQYNSHKEYTCKVTQGTTSV VQSFSRKNC | 6 |
| mAb2 | LC-02 | ADVVMTQTPSPVSAQVGGTVTINCQASESIDSDLS WYQQKPGQPPKLLIYRTFTLESGVPSRFKGSGSGT DYTLTISDLECADAAIYYCQCTDGSSISGSYGWDA FGGGTEVVVKGDPVAPTVLLFPPSSDEVATGTVTI VCVANKYFPDVTVTWEVDGTTQTTGIENSKTPQN SADCTYNLSSTLTLTSTQYNSHKEYTCKVTQGTTS VVQSFSRKNC | 8 |
| mAb3 | LC-03 | ADVVMTQTPSPVSAAVGGTVTINCRASEDIESFLA WYQQKPGQPPKLLMSRTSTLESGVPSRFKGSGSGT EFTLTISDLECADAATYYCQCTDGSSSSSSYGWDA FGGGTEVVVKGDPVAPTVLLFPPSSDEVATGTVTI VCVANKYFPDVTVTWEVDGTTQTTGIENSKTPQN SADCTYNLSSTLTLTSTQYNSHKEYTCKVTQGTTS VVQSFSRKNC | 10 |

TABLE 5-continued

Exemplary Antibody Light and Heavy Chain Amino Acid Sequences

| Antibody No. | Designation | Amino Acid Sequence | SEQ ID NO: |
|---|---|---|---|
| mAb4 | LC-04 | ADIVMTQTPASVSGAVGGTVTIKCQASQSIRNELS WYQQKPGQPPKLLIYKASTLASGVPSRFSGSGFGT EFTLTISGVQCDDAATYYCQNNYGTRRNNYVFPF GGGTEVVVKGDPVAPTVLLFPPSSDEVATGTVTIV CVANKYFPDVTVTWEVDGTTQTTGIENSKTPQNS ADCTYNLSSTLTLTSTQYNSHKEYTCKVTQGTTSV VQSFSRKNC | 12 |
| mAb5 | LC-05 | ADIVLTQTPASVSAAVGGTVSISCQSSESVYNNNY LSWFQQKPGQPPKLLIYGASTLASGVPSRFEGSGS GTQFTLTISDVQCDDAATYYCLGDYIIIENIFGGGT EVVVKGDPVAPTVLLFPPSSDEVATGTVTIVCVAN KYFPDVTVTWEVDGTTQTTGIENSKTPQNSADCT YNLSSTLTLTSTQYNSHKEYTCKVTQGTTSVVQSF SRKNC | 14 |
| mAb6 | LC-06 | AQVLTQTPASVSAAVGGTVTINCQASQSVYNNKN LAWYQQKPGQPPKLLIYFSSTLASGVPSRFRGSGS GTQFTLTISGVQCGDAATYYCLGEFGSIWAFGGGT EVVVKGDPVAPTVLLFPPSSDEVATGTVTIVCVAN KYFPDVTVTWEVDGTTQTTGIENSKTPQNSADCT YNLSSTLTLTSTQYNSHKEYTCKVTQGTTSVVQSF SRKNC | 16 |
| Heavy Chains | | | |
| mAb1 | HC-01 | QSLEESGGDLVKPGASLTLTCKASGIAFSNDYMC WVRQAPGKGLEWIACIFTGSSGSTYYASWAKGRF TISKTSSTTVTLQMTSLTAADTATYFCARDRAISVL GYFYAAYFFDFWGPGTLVTVSSGQPKAPSVFPLAP CCGDTPSSTVTLGCLVKGYLPEPVTVTWNSGTLTN GVRTFPSVRQSSGLYSLSSVVSVTSSSQPVTCNVA HPATNTKVDKTVAPSTCSKPTCPPPELLGGP SVFIFPPKPKDTLMISRTPEVTCVVVDVSQDDPEVQ FTWYINNEQVRTARPPLREQQFNSTIRVVSTLPIAH QDWLRGKEFKCKVHNKALPAPIEKTISKARGQPLE PKVYTMGPPREELSSRSVSLTCMINGFYPSDISVEW EKNGKAEDNYKTTPAVLDSDGSYFLYSKLSVPTSE WQRGDVFTCSVMHEALHNHYTQKSISRSPGK | 7 |
| mAb2 | HC-02 | QSLEESGGGLVQPEGSLTLTCTASGFSFNSSSYMC WVRQAPGKGLEWIGCIFTGSSGNTYYATWAQGRF TISKTSTTVTLEMTSLTAADTATYFCARDRAYFLV GYFYATYYFDLWGPGTLVTVSSGQPKAPSVFPLAP CCGDTPSSTVTLGCLVKGYLPEPVTVTWNSGTLTN GVRTFPSVRQSSGLYSLSSVVSVTSSSQPVTCNVA HPATNTKVDKTVAPSTCSKPTCPPPELLGGPSVFIF PPKPKDTLMISRTPEVTCVVVDVSQDDPEVQFTW YINNEQVRTARPPLREQQFNSTIRVVSTLPIAHQD WLRGKEFKCKVHNKALPAPIEKTISKARGQPLEPK VYTMGPPREELSSRSVSLTCMINGFYPSDISVEWE KNGKAEDNYKTTPAVLDSDGSYFLYSKLSVPTSE WQRGDVFTCSVMHEALHNHYTQKSISRSPGK | 9 |
| mAb3 | HC-03 | QSLEESGGGLVQPGASLTLTCTASGFSFSSNYYMC WVRQAPGKGLEWIACIFTGSSGSTYYASWAKGRF TISKTSSTTVTLHVTSLTAADTATYFCARDRALSV VGYFYAAYYFDWGPGTLVTVSSGQPKAPSVFPL APCCGDTPSSTVTLGCLVKGYLPEPVTVTWNSGTL TNGVRTFPSVRQSSGLYSLSSVVSVTSSSQPVTCNV AHPATNTKVDKTVAPSTCSKPTCPPPELLGG PSVFIFPPKPKDTLMISRTPEVTCVVVDVSQDDPEV QFTWYINNEQVRTARPPLREQQFNSTIRVVSTLPIA HQDWLRGKEFKCKVHNKALPAPIEKTISKARGQP LEPKVYTMGPPREELSSRSVSLTCMINGFYPSDISV EWEKNGKAEDNYKTTPAVLDSDGSYFLYSKLSVP TSEWQRGDVFTCSVMHEALHNHYTQKSISRSPGK | 11 |

TABLE 5-continued

Exemplary Antibody Light and Heavy Chain Amino Acid Sequences

| Antibody No. | Designation | Amino Acid Sequence | SEQ ID NO: |
|---|---|---|---|
| mAb4 | HC-04 | QSVEESGGRLVTPGTPLTLTCTASGIDLSSYAMIW VRQAPGEGLEYIGFIDAGDGNTYYASWAKGRFTIS KTSTTVDLKITSPTTEDTATYFCARGDPGWSNGFA LWGQGTLVTVSSGQPKAPSVFPLAPCCGDTPSSTV TLGCLVKGYLPEPVTVTWNSGTLTNGVRTFPSVR QSSGLYSLSSVVSVTSSSQPVTCNVAHPATNTKVD KTVAPSTCSKPTCPPPELLGGPSVFIFPPKPKDTLMI SRTPEVTCVVVDVSQDDPEVQFTWYINNEQVRTA RPPLREQQFNSTIRVVSTLPIAHQDWLRGKEFKCK VHNKALPAPIEKTISKARGQPLEPKVYTMGPPREE LSSRSVSLTCMINGFYPSDISVEWEKNGKAEDNYK TTPAVLDSDGSYFLYSKLSVPTSEWQRGDVFTCSV MHEALHNHYTQKSISRSPGK | 13 |
| mAb5 | HC-05 | QSVEESGGRLVTPGTPLTLTCTVSGFSLSTYNMCW VRQAPGKGLEWVGFINSDDSAYYASWAKGRFTFS KTSTTVDLKIASPTTEDTATYFCARYDWDYYYSRL DLWGPGTLVTVSSGQPKAPSVFPLAPCCGDTPSST VTLGCLVKGYLPEPVTVTWNSGTLTNGVRTFPSV RQSSGLYSLSSVVSVTSSSQPVTCNVAHPATNTKV DKTVAPSTCSKPTCPPPELLGGPSVFIFPPKPKDTL MISRTPEVTCVVVDVSQDDPEVQFTWYINNEQVR TARPPLREQQFNSTIRVVSTLPIAHQDWLRGKEFK CKVHNKALPAPIEKTISKARGQPLEPKVYTMGPPR EELSSRSVSLTCMINGFYPSDISVEWEKNGKAEDN YKTTPAVLDSDGSYFLYSKLSVPTSEWQRGDVFTC SVMHEALHNHYTQKSISRSPGK | 15 |
| mAb6 | HC-06 | QLEESGGGLVQPGASLTLTCTTSGFSLSDNYLCWV RQAPGRGLEWVACIGIVLRSTGATYYASWAEGRF TISKTSPTTVTLEMTSLTAADTATYFCALDLGYGG PLWGPGTLVTVSSGQPKAPSVFPLAPCCGDTPSST VTLGCLVKGYLPEPVTVTWNSGTLTNGVRTFPSV RQSSGLYSLSSVVSVTSSSQPVTCNVAHPATNTKV DKTVAPSTCSKPTCPPPELLGGPSVFIFPPKPKDTL MISRTPEVTCVVVDVSQDDPEVQFTWYINNEQVR TARPPLREQQFNSTIRVVSTLPIAHQDWLRGKEFK CKVHNKALPAPIEKTISKARGQPLEPKVYTMGPPR EELSSRSVSLTCMINGFYPSDISVEWEKNGKAEDN YKTTPAVLDSDGSYFLYSKLSVPTSEWQRGDVFTC SVMHEALHNHYTQKSISRSPGK | 17 |

Each of the exemplary light chains (LC-01, LC-02, LC-03 etc.) listed in Table 5 can be combined with any of the exemplary heavy chains in Table 5 to form an anti-PACAP antibody. Examples of such combinations include LC-01 combined with any of HC-01 through HC-06; LC-02 combined with any HC-01 through HC-06; LC-03 combined with any of HC-01 through HC-06, and so on. In some embodiments, the anti-PACAP antibodies include at least one heavy chain and one light chain from those listed in Table 5. In some embodiments, the anti-PACAP antibodies comprise two different heavy chains and two different light chains listed in Table 5. In other embodiments, the anti-PACAP antibodies contain two identical light chains and two identical heavy chains. As an example, an anti-PACAP antibody may include two HC-01 heavy chains and two LC-01 light chains, or two HC-02 heavy chains and two LC-02 light chains, or two HC-03 heavy chains and two LC-03 light chains and other similar combinations of pairs of light chains and pairs of heavy chains as listed in Table 5. In one embodiment, an anti-PACAP antibody of the invention comprises a light chain comprising a sequence selected from SEQ ID NOs: 6, 8, 10, 12, 14, or 16, and a heavy chain comprising a sequence selected from SEQ ID NOs: 7, 9, 11, 13, 15, or 17.

Variants of the anti-PACAP antibodies disclosed herein are also contemplated. For instance, variants of the antibodies can be formed by combination of heavy and light chains that each have at least 70%, 75%, 80%, 85%, 90%, 95%, 97% or 99% sequence identity to the amino acid sequences of the heavy and light chains listed in Table 5. In some instances, such antibodies include at least one heavy chain and one light chain, whereas in other instances the variant forms contain two identical light chains and two identical heavy chains.

In some embodiments, the anti-PACAP antibody comprises:

(a) a light chain comprising the sequence of SEQ ID NO: 6 and a heavy chain comprising the sequence of SEQ ID NO: 7;

(b) a light chain comprising the sequence of SEQ ID NO: 8 and a heavy chain comprising the sequence of SEQ ID NO: 9;

(c) a light chain comprising the sequence of SEQ ID NO: 10 and a heavy chain comprising the sequence of SEQ ID NO: 11;

(d) a light chain comprising the sequence of SEQ ID NO: 12 and a heavy chain comprising the sequence of SEQ ID NO: 13;

(e) a light chain comprising the sequence of SEQ ID NO: 14 and a heavy chain comprising the sequence of SEQ ID NO: 15; or (f) a light chain comprising the sequence of SEQ ID NO: 16 and a heavy chain comprising the sequence of SEQ ID NO: 17.

The anti-PACAP antibodies of the invention can be monoclonal antibodies, polyclonal antibodies, recombinant antibodies, human antibodies, humanized antibodies, chimeric antibodies, or multispecific antibodies. In certain embodiments, the anti-PACAP antibody is a monoclonal antibody. In such embodiments, the anti-PACAP antibody may be a humanized antibody or a chimeric antibody having a human immunoglobulin constant domain. In these and other embodiments, the anti-PACAP antibody is an IgG1, IgG2, IgG3, or IgG4 antibody. Thus, the anti-PACAP antibody may, in some embodiments, have a human IgG1, IgG2, IgG3, or IgG4 constant domain. In one embodiment, the anti-PACAP antibody is a monoclonal IgG1 antibody. In another embodiment, the anti-PACAP antibody is a monoclonal IgG2 antibody.

The term "monoclonal antibody" (or "mAb") as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some instances, a hybridoma cell line is produced by immunizing an animal (e.g., a rabbit, rat, mouse, or a transgenic animal having human immunoglobulin sequences) with a PACAP immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds to PACAP. Another useful method for producing monoclonal antibodies is the SLAM method described in Example 1 herein and in Babcook et al., Proc. Natl. Acad. Sci. USA, Vol. 93: 7843-7848, 1996, which is hereby incorporated by reference in its entirety.

Monoclonal antibodies secreted by a hybridoma cell line can be purified using any technique known in the art, such as protein A-Sepharose, hydroxylapatite chromatography, gel electrophoresis, dialysis, or affinity chromatography. Hybridoma supernatants or mAbs may be further screened to identify mAbs with particular properties, such as the ability to bind PACAP38, PACAP27, or regions thereof (e.g. C- or N-terminal domains); ability to block or interfere with the binding of the PACAP ligand to its receptors, or the ability to functionally block PACAP-induced activation of the VPAC1, VPAC2, or PAC1 receptors, e.g., using a cAMP assay as described herein.

In some embodiments, the anti-PACAP antibodies of the invention are chimeric or humanized antibodies based upon the CDR and variable region sequences of the antibodies described herein. A chimeric antibody is an antibody composed of protein segments from different antibodies that are covalently joined to produce functional immunoglobulin light or heavy chains or binding fragments thereof. Generally, a portion of the heavy chain and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. For methods relating to chimeric antibodies, see, for example, U.S. Pat. No. 4,816,567 and Morrison el al., 1985, Proc. Natl. Acad. Sci. USA 81:6851-6855, both of which are hereby incorporated by reference in their entireties.

Generally, the goal of making a chimeric antibody is to create a chimera in which the number of amino acids from the intended species is maximized. One example is the "CDR-grafted" antibody, in which the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. CDR grafting is described, for example, in U.S. Pat. Nos. 6,180,370, 5,693,762, 5,693,761, 5,585,089, and 5,530,101. For use in humans, the variable region or selected CDRs from a rodent or rabbit antibody often are grafted into a human antibody, replacing the naturally-occurring variable regions or CDRs of the human antibody.

For instance, in some embodiments, a chimeric antibody of the invention comprises a light chain variable region and a heavy chain variable region selected from those listed in Table 2 fused to a human light chain constant region, such as those listed in Table 3, and/or a human heavy chain constant region, such as those listed in Table 4. In one embodiment, the chimeric antibody specifically binds to a C-terminal domain of PACAP38 (e.g. within amino acids 28-38 of SEQ ID NO: 1; within amino acids 28-37 of SEQ ID NO: 1; or within amino acids 34-38 of SEQ ID NO. 1) and comprises a light chain variable region comprising a sequence selected from SEQ ID NOs: 18, 20, and 22; a heavy chain variable region comprising a sequence selected from SEQ ID NOs: 19, 21, and 23; and a human constant region. In another embodiment, the chimeric antibody specifically binds to an N-terminal domain or central domain of PACAP38 (e.g. within amino acids 1-13 of SEQ ID NO: 1; within amino acids 6-20 of SEQ ID NO: 1; or within amino acids 14-27 of SEQ ID NO: 1) and comprises a light chain variable region comprising a sequence selected from SEQ ID NOs: 24, 26, and 28; a heavy chain variable region comprising a sequence selected from SEQ ID NOs: 25, 27, and 29; and a human constant region. The human light chain constant region can be from a human lambda or kappa light chain, and the human heavy chain constant region can be from an IgG (e.g. IgG1, IgG2, IgG3, or IgG4) constant region. In certain embodiments, the chimeric antibodies comprise a human IgG1, IgG2, IgG3, or IgG4 Fc region. As used herein, the term "Fc region" refers to the C-terminal region of an immunoglobulin heavy chain which may be generated by papain digestion of an intact antibody. The Fc region of an immunoglobulin generally comprises two constant domains, a CH2 domain and a CH3 domain, and optionally comprises a CH4 domain. In certain embodiments, the Fc region is an Fc region from an IgG1, IgG2, IgG3, or IgG4 immunoglobulin. In some embodiments, the Fc region comprises CH2 and CH3 domains from a human IgG1 or human IgG2 immunoglobulin. The Fc region may retain effector function, such as C1q binding, complement dependent cytotoxicity (CDC), Fc receptor binding, antibody-dependent cell-mediated cytotoxicity (ADCC), and phagocytosis. In other embodiments, the Fc region may be modified to reduce or eliminate effector function as described in further detail herein.

One useful type of chimeric antibody is a "humanized" antibody. Generally, a humanized antibody is produced from a monoclonal antibody raised initially in a non-human animal, such as a rodent or rabbit. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent or rabbit variable region for the corresponding regions of a human antibody (see, e.g., U.S. Pat. Nos. 5,585,089, and 5,693,762; Jones el al., 1986, Nature 321:522-525; Riechmann et al., 1988, Nature 332: 323-27; and Verhoeyen et al., 1988, Science 239:1534-1536).

In one aspect, the CDRs of the light and heavy chain variable regions of the antibodies provided herein (see, Table 1) are grafted to framework regions (FRs) from antibodies from the same, or a different, phylogenetic species. For example, the CDRs of the heavy and light chain variable regions listed in Table 1 can be grafted to consensus human FRs. To create consensus human FRs, FRs from several human heavy chain or light chain amino acid sequences may be aligned to identify a consensus amino acid sequence. Alternatively, the grafted variable regions from the one heavy or light chain may be used with a constant region that is different from the constant region of that particular heavy or light chain as disclosed herein. In other embodiments, the grafted variable regions are part of a single chain Fv antibody.

In some embodiments, a humanized antibody of the invention specifically binds to a C-terminal domain of PACAP38 (e.g. within amino acids 28-38 of SEQ ID NO: 1; within amino acids 28-37 of SEQ ID NO: 1; or within amino acids 34-38 of SEQ ID NO: 1). Such C-terminal-binding humanized antibodies may comprise a CDRL1 of SEQ ID NO: 30 or 31, a CDRL2 of SEQ ID NO: 35 or 36, a CDRL3 of SEQ ID NO: 40 or 41, a CDRH1 selected from SEQ ID NOs: 45-47, a CDRH2 of SEQ ID NO: 51 or 52, a CDRH3 selected from SEQ ID NOs: 56-58, human framework regions, and a human constant region. In another embodiment, the humanized antibody specifically binds to an N-terminal domain or central domain of PACAP38 (e.g. within amino acids 1-13 of SEQ ID NO: 1, within amino acids 6-20 of SEQ ID NO: 1; or within amino acids 14-27 of SEQ ID NO: 1). Such N-terminal- or central domain-binding humanized antibodies may comprise a CDRL1 selected from SEQ ID NOs: 32-34, a CDRL2 selected from SEQ ID NOs: 37-39, a CDRL3 selected from SEQ ID NOs: 42-44, a CDRH1 selected from SEQ ID NOs: 48-50, a CDRH2 selected from SEQ ID NO: 53-55, a CDRH3 selected from SEQ ID NOs: 59-61, human framework regions, and a human constant region. In certain embodiments, the humanized antibodies comprise a human IgG1, IgG2, IgG3, or IgG4 Fc region.

Fully human antibodies that specifically bind to human PACAP can be generated using the immunogens or fragments thereof described herein, such as polypeptides consisting of the sequences of SEQ ID NOs: 1, 2, 4, and 5. A "fully human antibody" is an antibody that comprises variable and constant regions derived from or indicative of human germ line immunoglobulin sequences. One specific means provided for implementing the production of fully human antibodies is the "humanization" of the mouse humoral immune system. Introduction of human immunoglobulin (Ig) loci into mice in which the endogenous Ig genes have been inactivated is one means of producing fully human monoclonal antibodies (mAbs) in mouse, an animal that can be immunized with any desirable antigen. Using fully human antibodies can minimize the immunogenic and allergic responses that can sometimes be caused by administering mouse or mouse-derived mAbs to humans as therapeutic agents.

Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits el al., 1993, Proc. Natl. Acad. Sci. USA 90:2551-2555; Jakobovits et al., 1993, Nature 362:255-258; and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,939,598; 5,545,807; 6,300,129; 6,255,458; 5,877,397; 5,874,299 and 5,545,806; in PCT publications WO91/10741, WO90/04036, WO 94/02602, WO 96/30498, WO 98/24893 and in EP 546073B1 and EP 546073A1.

The transgenic mice described above, referred to herein as "HuMab" mice, contain a human immunoglobulin gene minilocus that encodes unrearranged human heavy (mu and gamma) and kappa light chain immunoglobulin sequences, together with targeted mutations that inactivate the endogenous mu and kappa chain loci (Lonberg et al., 1994, Nature 368:856-859). Accordingly, the mice exhibit reduced expression of mouse IgM and kappa proteins and in response to immunization, the introduced human heavy and light chain transgenes undergo class switching and somatic mutation to generate high affinity human IgG kappa monoclonal antibodies (Lonberg et al., supra.; Lonberg and Huszar, 1995, Intern. Rev. Immunol. 13: 65-93; Harding and Lonberg, 1995, Ann. N.Y Acad. Sci. 764:536-546). The preparation of HuMab mice is described in detail in Taylor et al., 1992, Nucleic Acids Research 20:6287-6295; Chen et al., 1993, International Immunology 5:647-656; Tuaillon et al., 1994, J. Immunol. 152:2912-2920; Lonberg et al., 1994, Nature 368:856-859; Lonberg, 1994, Handbook of Exp. Pharmacology 113:49-101; Taylor et al., 1994, International Immunology 6:579-591; Lonberg and Huszar, 1995, Intern. Rev. Immunol. 13:65-93; Harding and Lonberg, 1995, Ann. N.Y Acad. Sci. 764:536-546; Fishwild et al., 1996, Nature Biotechnology 14:845-851; the foregoing references are hereby incorporated by reference in their entireties for all purposes. See, further U.S. Pat. Nos. 5,545,806; 5,569,825; 5,625,126; 5,633,425; 5,789,650; 5,877,397; 5,661,016; 5,814,318; 5,874,299; and 5,770,429, as well as U.S. Pat. No. 5,545,807; International Publication Nos. WO 93/1227; WO 92/22646; and WO 92/03918, the disclosures of all of which are hereby incorporated by reference in their entireties for all purposes. Technologies utilized for producing human antibodies in these transgenic mice are disclosed also in WO 98/24893, and Mendez et al., 1997, Nature Genetics 15:146-156, which are hereby incorporated by reference. For example, the HCo7 and HCo12 transgenic mice strains can be used to generate fully human anti-PACAP antibodies.

Human-derived antibodies can also be generated using phage display techniques. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function, if desired. Typically, the Fd fragment (VH-CH1) and light chain (VL-CL) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated. Phage display techniques can also be used in an approach for the humanization of rodent monoclonal antibodies, called "guided selection" (see Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

In certain embodiments, the anti-PACAP antigen binding proteins of the invention (e.g. monoclonal antibodies or binding fragments thereof) compete for binding to human PACAP38 (SEQ ID NO: 1) with a reference antibody, such as one or more of the anti-PACAP antibodies described herein. The term "compete" refers to the ability of an antibody or other antigen binding protein to interfere with the binding of other antibodies or binding fragments to a target (e.g. human PACAP38). The extent to which an antibody or binding fragment is able to interfere with the binding of another antibody or binding fragment to a target (e.g. human PACAP38), and therefore whether it can be said to compete, can be determined using competition binding assays. Numerous types of competitive binding assays can be used, including for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619); solid phase direct-labeled assay, solid phase direct-labeled sandwich assay (see, e.g., Harlow and Lane, 1988, Antibodies, A Laboratory Manual, Cold Spring Harbor Press); solid phase direct label RIA using I-125 label (see, e.g., Morel et al., 1988, Molec. Immunol. 25:7-15); solid phase direct biotin-avidin EIA (see, e.g., Cheung, et al., 1990, Virology 176: 546-552); and direct labeled RIA (Moldenhauer et al., 1990, Scand. J. Immunol. 32:77-82). Typically, a competitive binding assay involves the use of purified antigen bound to a solid surface or cells bearing the antigen, an unlabeled test antibody or other antigen binding protein, and a labeled reference antibody or other antigen binding protein. Competitive inhibition is measured by determining the amount of label bound to the solid surface or cells in the presence of the test antibody or other antigen binding protein. Usually the test antibody or other antigen binding protein is present in excess. Antibodies or other antigen binding proteins identified by competition assay (i.e. competing antibodies and antigen binding proteins) include antibodies and antigen binding proteins binding to the same epitope as the reference antibody or antigen binding protein. Usually, when a competing antibody or other antigen binding protein is present in excess, it will inhibit specific binding of a reference antibody or other antigen binding protein to a target antigen by at least 40%, 45%, 50%, 55%, 60%, 65%, 70% or 75%. In some instances, binding of the reference antibody or other antigen binding protein is inhibited by at least 80%, 85%, 90%, 95%, or 97% or more. In some embodiments, a competing antigen binding protein (e.g. antibody or binding fragment thereof) reduces human PACAP38 binding of a reference antibody between about 40% and about 100%, such as about 60% and about 100%, specifically between about 70% and about 100%, and more specifically between about 80% and about 100%.

A particularly suitable quantitative assay for detecting competitive binding uses a Biacore machine which measures the extent of interactions using surface plasmon resonance technology. An exemplary Biacore-based competitive binding assay involves the immobilization of a reference antibody to a sensor chip. The target antigen is then contacted with the sensor chip where the target antigen is captured by the immobilized reference antibody. Test antibodies are then injected over the captured target antigen. If the injected test antibody recognizes a distinct epitope from that recognized by the immobilized antibody, then a second binding event is observed and the test antibody would be considered not to compete for binding to the target antigen with the reference antibody.

In one embodiment, an antigen binding protein of the invention competes with a reference antibody for binding to human PACAP38, wherein the reference antibody comprises: (a) a light chain variable region comprising the sequence of SEQ ID NO: 18 and a heavy chain variable region comprising the sequence of SEQ ID NO: 19; (b) a light chain variable region comprising the sequence of SEQ ID NO: 20 and a heavy chain variable region comprising the sequence of SEQ ID NO: 21; or (c) a light chain variable region comprising the sequence of SEQ ID NO: 22 and a heavy chain variable region comprising the sequence of SEQ ID NO: 23. In some embodiments, the reference antibody comprises: (a) a light chain comprising the sequence of SEQ ID NO: 6 and a heavy chain comprising the sequence of SEQ ID NO: 7; (b) a light chain comprising the sequence of SEQ ID NO: 8 and a heavy chain comprising the sequence of SEQ ID NO: 9; or (c) a light chain comprising the sequence of SEQ ID NO: 10 and a heavy chain comprising the sequence of SEQ ID NO: 11. As shown by the Examples herein, reference antibodies defined by these sequences (e.g. mAb1, mAb2, and mAb3) have been found to bind to an epitope within the C-terminal domain of PACAP38, e.g. within amino acids 28-38 of SEQ ID NO: 1. Thus, antigen binding proteins that compete with these reference antibodies would also bind to a similar epitope within the C-terminal domain of PACAP38.

In another embodiment, an antigen binding protein of the invention competes with a reference antibody for binding to human PACAP38, wherein the reference antibody comprises: (a) a light chain variable region comprising the sequence of SEQ ID NO: 24 and a heavy chain variable region comprising the sequence of SEQ ID NO: 25; (b) a light chain variable region comprising the sequence of SEQ ID NO: 26 and a heavy chain variable region comprising the sequence of SEQ ID NO: 27; or (c) a light chain variable region comprising the sequence of SEQ ID NO: 28 and a heavy chain variable region comprising the sequence of SEQ ID NO: 29. In some embodiments, the reference antibody comprises: (a) a light chain comprising the sequence of SEQ ID NO: 12 and a heavy chain comprising the sequence of SEQ ID NO: 13; (b) a light chain comprising the sequence of SEQ ID NO: 14 and a heavy chain comprising the sequence of SEQ ID NO: 15; or (c) a light chain comprising the sequence of SEQ ID NO: 16 and a heavy chain comprising the sequence of SEQ ID NO: 17. As shown by the Examples herein, reference antibodies defined by these sequences (e.g. mAb4, mAb5, and mAb6) have been found to bind to an epitope within the N-terminal domain or central domain of PACAP38, e.g. within amino acids 1-13 of SEQ ID NO: 1; within amino acids 6-20 of SEQ ID NO: 1; or within amino acids 14-27 of SEQ ID NO: 1. Accordingly, antigen binding proteins that compete with these reference antibodies would also bind to a similar epitope within the N-terminal or central domain of PACAP38.

The heavy chain constant regions or the Fc regions of the antigen binding proteins (e.g. monoclonal antibodies) described herein may comprise one or more amino acid substitutions that affect the glycosylation and/or effector function of the antigen binding protein. One of the functions of the Fc region of an immunoglobulin is to communicate to the immune system when the immunoglobulin binds its target. This is commonly referred to as "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc region to Fc receptors on the surface of cells of the immune system. CDC is mediated through the binding of the Fc with proteins of the complement system, e.g., C1q. In some embodiments, the antigen binding proteins, e.g. monoclonal antibodies, of the invention comprise one or more amino acid substitutions in the constant region to enhance effector function, including ADCC activity, CDC activity, ADCP activity, and/or the clearance or half-life of the antigen binding protein. Exemplary amino acid substitutions (EU numbering) that can enhance effector function include, but are not limited to, E233L, L234L, L234Y, L235S, G236A, S239D, F243L, F243V, P247I, D280H, K290S, K290E, K290N, K290Y, R292P, E294L, Y296W, S298A, S298D, S298V, S298G, S298T, T299A, Y300L, V305I, Q311M, K326A, K326E, K326W, A330S, A330L, A330M, A330F, I332E, D333A, E333S, E333A, K334A, K334V, A339D, A339Q, P396L, or combinations of any of the foregoing.

In other embodiments, the antigen binding proteins (e.g. monoclonal antibodies) of the invention comprise one or more amino acid substitutions in the constant region to reduce effector function. Exemplary amino acid substitutions (EU numbering) that can reduce effector function include, but are not limited to, C220S, C226S, C229S, E233P, L234A, L234V, V234A, L234F, L235A, L235E, G237A, P238S, S267E, H268Q, N297A, N297G, V309L, E318A, L328F, A330S, A331S, P331S or combinations of any of the foregoing.

Glycosylation can contribute to the effector function of antibodies, particularly IgG1 antibodies. Thus, in some embodiments, the antigen binding proteins of the invention may comprise one or more amino acid substitutions that affect the level or type of glycosylation of the binding proteins. Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

In certain embodiments, glycosylation of the antigen binding proteins described herein is increased by adding one or more glycosylation sites, e.g., to the Fc region of the binding protein. Addition of glycosylation sites to the antigen binding protein can be conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence may be altered through changes at the DNA level, particularly by mutating the DNA encoding the target polypeptide at preselected bases such that codons are generated that will translate into the desired amino acids.

The invention also encompasses production of antigen binding protein molecules with altered carbohydrate structure resulting in altered effector activity, including antigen binding proteins with absent or reduced fucosylation that exhibit improved ADCC activity. Various methods are known in the art to reduce or eliminate fucosylation. For example, ADCC effector activity is mediated by binding of the antibody molecule to the FcγRIII receptor, which has been shown to be dependent on the carbohydrate structure of the N-linked glycosylation at the N297 residue of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (see Yamane-Ohnuki el al., Biotechnol Bioeng. 87(5):614-22, 2004). Similar effects can be accomplished through decreasing the activity of alpha-1,6-fucosyl transferase enzyme or other enzymes in the fucosylation pathway, e.g., through siRNA or antisense RNA treatment, engineering cell lines to knockout the enzyme(s), or culturing with selective glycosylation inhibitors (see Rothman et al., Mol Immunol. 26(12):1113-23, 1989). Some host cell strains, e.g. Lec13 or rat hybridoma YB2/0 cell line naturally produce antibodies with lower fucosylation levels (see Shields et al., J Biol Chem. 277(30):26733-40, 2002 and Shinkawa et al., J Biol Chem. 278(5):3466-73, 2003). An increase in the level of bisected carbohydrate, e.g. through recombinantly producing antibody in cells that overexpress GnTIII enzyme, has also been determined to increase ADCC activity (see Umana et al., Nat Biotechnol. 17(2):176-80, 1999).

In other embodiments, glycosylation of the antigen binding proteins described herein is decreased or eliminated by removing one or more glycosylation sites, e.g., from the Fc region of the binding protein. Amino acid substitutions that eliminate or alter N-linked glycosylation sites can reduce or eliminate N-linked glycosylation of the antigen binding protein. In certain embodiments, the antigen binding proteins described herein comprise a mutation at position N297 (EU numbering), such as N297Q, N297A, or N297G. In one particular embodiment, the antigen binding proteins of the invention comprise an Fc region from a human IgG1 antibody with a N297G mutation. To improve the stability of molecules comprising a N297 mutation, the Fc region of the molecules may be further engineered. For instance, in some embodiments, one or more amino acids in the Fc region are substituted with cysteine to promote disulfide bond formation in the dimeric state. Residues corresponding to V259, A287, R292, V302, L306, V323, or I332 (EU numbering) of an IgG1 Fc region may thus be substituted with cysteine. Preferably, specific pairs of residues are substituted with cysteine such that they preferentially form a disulfide bond with each other, thus limiting or preventing disulfide bond scrambling. Preferred pairs include, but are not limited to, A287C and L306C, V259C and L306C, R292C and V302C, and V323C and I332C. In particular embodiments, the antigen binding proteins described herein comprise an Fc region from a human IgG1 antibody with mutations R292C and V302C. In such embodiments, the Fc region may also comprise a N297G mutation.

Modifications of the antigen binding proteins of the invention to increase serum half-life also may desirable, for example, by incorporation of or addition of a salvage receptor binding epitope (e.g., by mutation of the appropriate region or by incorporating the epitope into a peptide tag that is then fused to the antigen binding protein at either end or in the middle, e.g., by DNA or peptide synthesis; see, e.g., WO96/32478) or adding molecules such as PEG or other water soluble polymers, including polysaccharide polymers. The salvage receptor binding epitope preferably constitutes a region wherein any one or more amino acid residues from one or two loops of an Fc region are transferred to an analogous position in the antigen binding protein. Even more preferably, three or more residues from one or two loops of the Fc region are transferred. Still more preferred, the epitope is taken from the CH2 domain of the Fc region (e.g., an IgG Fc region) and transferred to the CH1, CH3, or VH region, or more than one such region, of the antigen binding protein. Alternatively, the epitope is taken from the CH2 domain of the Fc region and transferred to the CL region or VL region, or both, of the antigen binding protein. See International applications WO 97/34631 and WO 96/32478 for a description of Fc variants and their interaction with the salvage receptor.

The present invention includes one or more isolated polynucleotides or isolated nucleic acids encoding the antigen binding proteins, such as monoclonal antibodies, described herein. Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention can be derived from human sources as well as non-human species.

Relevant amino acid sequences from an immunoglobulin or region thereof (e.g. variable region, Fc region, etc.) or polypeptide of interest may be determined by direct protein sequencing, and suitable encoding nucleotide sequences can be designed according to a universal codon table. Alternatively, genomic or cDNA encoding monoclonal antibodies or binding fragments thereof of the invention can be isolated and sequenced from cells producing such antibodies using conventional procedures (e.g., by using oligonucleotide probes that are capable of binding specifically to genes encoding the heavy and light chains of the monoclonal antibodies).

An "isolated nucleic acid," which is used interchangeably herein with "isolated polynucleotide," is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning: A Laboratory Manual, 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region. Unless specified otherwise, the left-hand end of any single-stranded polynucleotide sequence discussed herein is the 5' end: the left-hand direction of double-stranded polynucleotide sequences is referred to as the 5' direction. The direction of 5' to Y production of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The present invention also includes nucleic acids that hybridize under moderately stringent conditions, and more preferably highly stringent conditions, to nucleic acids encoding polypeptides as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a prewashing solution containing 5×SSC, 0.5% SDS, 1.0 mM EDTA (pH 8.0), hybridization buffer of about 50% formamide, 6×SSC, and a hybridization temperature of about 55° C. (or other similar hybridization solutions, such as one containing about 50% formamide, with a hybridization temperature of about 42° C.), and washing conditions of about 60° C., in 0.5×SSC, 0.1% SDS. Generally, highly stringent conditions are defined as hybridization conditions as above, but with washing at approximately 68° C., 0.2×SSC, 0.1% SDS. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989).

When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids above 18 base pairs in length, Tm (° C.)=81.5+16.6(log 10 [Na+])+0.41(% G+C)−(600/N), where N is the number of bases in the hybrid, and [Na+] is the concentration of sodium ions in the hybridization buffer ([Na+] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99/o, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

Variants of the antigen binding proteins described herein can be prepared by site-specific mutagenesis of nucleotides in the DNA encoding the polypeptide, using cassette or PCR mutagenesis or other techniques well known in the art, to produce DNA encoding the variant, and thereafter expressing the recombinant DNA in cell culture as outlined herein. However, antigen binding proteins comprising variant CDRs having up to about 100-150 residues may be prepared by in vitro synthesis using established techniques. The variants typically exhibit the same qualitative biological activity as the naturally occurring analogue, e.g., binding to antigen. Such variants include, for example, deletions and/or insertions and/or substitutions of residues within the amino acid sequences of the antigen binding proteins. Any combination of deletion, insertion, and substitution is made to arrive at the final construct, provided that the final construct possesses the desired characteristics. The amino acid changes also may alter post-translational processes of the antigen binding protein, such as changing the number or position of glycosylation sites. In certain embodiments, antigen binding protein variants are prepared with the intent to modify those amino acid residues which are directly involved in epitope binding. In other embodiments, modification of residues which are not directly involved in epitope binding or residues not involved in epitope binding in any way, is desirable, for purposes discussed herein. Mutagenesis within any of the CDR regions and/or framework regions is contemplated. Covariance analysis techniques can be employed by the skilled artisan to design useful modifications in the amino acid sequence of the antigen binding protein. See, e.g., Choulier, et al., Proteins 41:475-484, 2000; Demarest et al., J. Mol. Biol. 335:41-48, 2004; Hugo et al., Protein Engineering 16(5):381-86, 2003; Aurora et al., US Patent Publication No. 2008/0318207 A1; Glaser et al., US Patent Publication No. 2009/0048122 A1; Urech et al., WO 2008/110348 A1; Borras et al., WO 2009/000099 A2. Such modifications determined by covariance analysis can improve potency, pharmacokinetic, pharmacodynamic, and/or manufacturability characteristics of an antigen binding protein.

Table 6 shows exemplary nucleic acid sequences encoding the light and heavy chain variable regions of anti-PACAP antibodies, and Table 7 lists exemplary nucleic acid sequences encoding the full-length light and heavy chains of the anti-PACAP antibodies. Polynucleotides encoding the anti-PACAP variable regions and full chains can be used to construct the antigen binding proteins described herein.

TABLE 6

Exemplary Anti-PACA PVariable Region Nucleic Acid Sequences

| Antibody ID | Designation | Nucleic Acid Sequence | SEQ ID NO: |
|---|---|---|---|
| \multicolumn{4}{c}{Light chain variable regions} |

| Antibody ID | Designation | Nucleic Acid Sequence | SEQ ID NO: |
|---|---|---|---|
| mAb1 | LV-01 | GCCGATGTCGTGATGACCCAGACTCCATCCCCCGTGTCTGCAGCTG TGGGAGGCACAGTCACCATCAATTGCCGGGCCAGTGAGGACATTG AAAGCTTTTTAGCCTGGTATCAGCAGAAACCAGGGCAGCCTCCCA AGCTCCTGATCTCCAGGACATCCACTCTGGAATCTGGGGTCTCATC GCGGTTCAAAGGCAGTGGATCGGGGACAGAGTTCATTCTCACCAT CAGCGACCTGGAGTGTGCCGATGCTGCCACTTACTACTGTCAATGT ACTGATGGTAGTAGTAGTAGTAGTAGTTATGGTTGGGATGCTTTCG GCGGAGGGACCGAGGTGGTGGTCAAAGGT | 72 |
| mAb2 | LV-02 | GCCGATGTCGTGATGACCCAGACTCCATCCCCCGTGTCTGCGCAGG TGGGAGGCACAGTCACCATCAATTGCCAGGCCAGTGAGAGCATTG ATAGTGACTTATCCTGGTATCAACAGAAACCAGGGCAGCCTCCCA AGCTCCTGATCTACAGGACATTCACTCTGGAATCTGGGGTCCCATC GCGGTTCAAAGGCAGTGGATCTGGGACAGACTACACTCTCACCAT CAGCGACCTGGAGTGTGCCGATGCTGCCATTTACTACTGTCAATGC ACTGATGGTAGTAGTATTAGTGGTAGTTATGGTTGGGATGCTTTCG GCGGAGGGACCGAGGTGGTGGTCAAAGGT | 73 |
| mAb3 | LV-03 | GCCGATGTCGTGATGACCCAGACTCCATCCCCCGTGTCTGCAGCTG TGGGAGGCACAGTCACCATCAATTGCCGGGCCAGTGAGGACATTG AAAGCTTTTTAGCCTGGTATCAGCAGAAACCAGGGCAGCCTCCCA AGCTCCTGATGTCCAGGACATCCACTCTGGAATCTGGGGTCCCATC GCGGTTCAAAGGCAGTGGATCTGGGACAGAGTTCACTCTCACCAT CAGCGACCTGGAGTGTGCCGATGCTGCCACATATTACTGTCAATGT ACTGATGGTAGTAGTAGTAGTAGTAGTTATGGTTGGGATGCTTTCG GCGGAGGGACCGAGGTGGTGGTCAAAGGT | 74 |
| mAb4 | LV-04 | GCTGACATTGTGATGACCCAGACTCCAGCCTCCGTGTCTGGAGCTG TGGGAGGCACAGTCACCATCAAGTGCCAGGCCAGTCAGAGCATTA GGAATGAATTATCCTGGTATCAGCAGAAACCAGGGCAGCCTCCCA AGCTCCTGATCTACAAGGCATCCACTCTGGCATCTGGGGTCCCATC GCGGTTCAGTGGCAGTGGATTTGGGACAGAGTTCACTCTCACCATC AGCGGTGTGCAGTGTGATGATGCTGCCACTTACTACTGTCAAAAC AATTATGGTACTAGGCGTAATAATTATGTTTTTCCTTTCGGCGGAG GGACCGAGGTGGTGGTCAAAGGT | 75 |
| mAb5 | LV-05 | GCTGACATCGTGCTGACCCAGACTCCAGCCTCCGTGTCTGCAGCTG TGGGAGGCACAGTCAGCATCAGTTGCCAGTCCAGTGAAAGTGTTT ATAATAACAACTACTTATCCTGGTTTCAGCAGAAACCAGGGCAGC CTCCCAAGCTCCTGATCTATGGTGCATCCACTCTGGCATCTGGGGT CCCATCGCGGTTTGAAGGCAGTGGATCTGGGACACAGTTCACTCTC ACCATCAGCGACGTGCAGTGTGATGATGCTGCCACTTACTACTGTC TAGGCGATTATATTATTATTGAGAATATTTTCGGCGGAGGGACCGA GGTGGTGGTCAAAGGT | 76 |
| mAb6 | LV-06 | GCGCAAGTGCTGACCCAGACTCCAGCCTCCGTGTCTGCGGCTGTG GGAGGCACAGTCACCATCAATTGCCAGGCCAGTCAGAGTGTTTAT AACAACAAAAATTTAGCCTGGTATCAGCAGAAACCAGGGCAGCC TCCCAAGCTCCTGATCTATTTTTCATCCACTCTGGCATCTGGGGTCC CATCGCGGTTCAGAGGCAGTGGATCTGGGACACAGTTCACTCTCA CCATCAGTGGCGTGCAGTGTGGCGATGCTGCCACTTACTACTGTCT AGGCGAATTTGGTAGTATTTGGGCTTTCGGCGGAGGGACCGAGGT GGTGGTCAAAGGT | 77 |

| \multicolumn{4}{c}{Heavy chain variable regions} |

| Antibody ID | Designation | Nucleic Acid Sequence | SEQ ID NO: |
|---|---|---|---|
| mAb1 | HV-01 | CAGTCGTTGGAGGAGTCCGGGGGAGACCTGGTCAAGCCTGGGG CATCTCTGACACTCACCTGCAAAGCCTCTGGAATCGCCTTCAGTAA CGACTACATGTGCTGGGTCCGCCAGGCTCCAGGGAAGGGGCTGGA GTGGATCGCATGTATTTTTACTGGTAGTAGTGGTAGTACTTACTAC GCGAGCTGGGCGAAAGGTCGATTCACCATCTCCAAAACCTCGTCG ACCACGGTGACTCTGCAAATGACCAGTCTGACAGCCGCGGACACG GCCACCTATTTCTGTGCGAGAGATAGGGCTATTTCTGTACTTGGTT ATTTCTATGCTGCATACTTCTTTGACTTCTGGGGCCCAGGCACCCT GGTCACCGTCTCCTCA | 78 |

TABLE 6-continued

Exemplary Anti-PACA PVariable Region Nucleic Acid Sequences

| Antibody ID | Designation | Nucleic Acid Sequence | SEQ ID NO: |
|---|---|---|---|
| mAb2 | HV-02 | CAGTCGTTGGAGGAGTCCGGGGAGGCCTGGTCCAGCCTGAGG GATCCCTGACACTCACCTGCACAGCTTCTGGATTCTCCTTCAATAG CAGCTCCTACATGTGCTGGGTCCGCCAGGCTCCAGGGAAGGGGCT GGAGTGGATCGGATGCATTTTTACTGGTAGTAGTGGTAATACCTAC TACGCGACCTGGGCGCAAGGTCGATTCACCATCTCCAAGACCTCG ACCACGGTGACTCTGGAAATGACCAGTCTGACAGCCGCGGACACG GCCACCTATTTCTGTGCGAGAGATAGGGCTTATTTTTTGGTTGGTT ATTTCTATGCTACATATTATTTTGACTTATGGGGCCCAGGCACCCT GGTCACCGTCTCCTCA | 79 |
| mAb3 | HV-03 | CAGTCGTTGGAGGAGTCCGGGGGAGGCCTGGTCCAGCCTGGGG CATCTCTGACACTCACCTGTACAGCCTCTGGATTCTCCTTCAGTAG CAACTACTACATGTGCTGGGTCCGCCAGGCTCCAGGGAAGGGGCT GGAGTGGATCGCATGCATTTTTACTGGTAGTAGTGGTAGCACTTAC TACGCGAGCTGGGCGAAAGGCCGATTCACCATCTCCAAAACCTCG TCGACCACGGTGACTCTGCACGTGACCAGTCTGACAGCCGCGGAC ACGGCCACCTATTTCTGTGCGAGAGATAGGGCTTTGTCTGTTGTTG GTTATTTCTATGCTGCATACTACTTTGACTTCTGGGGCCCAGGCAC CCTGGTCACCGTCTCCTCA | 80 |
| mAb4 | HV-04 | CAGTCGGTGGAGGAGTCCGGGGGTCGCCTGGTCACGCCTGGGACA CCCCTGACACTCACCTGCACAGCCTCTGGAATCGACCTCAGTAGCT ATGCAATGATCTGGGTCCGCCAGGCTCCAGGAGAGGGACTGGAAT ACATCGGATTCATTGATGCTGGTGATGGTAACACTTACTACGCGAG CTGGGCAAAAGGCCGATTCACCATCTCCAAAACCTCGACCACGGT GGATCTGAAAATCACCAGTCCGACAACCGAGGACACGGCCACCTA TTTCTGTGCCAGAGGAGATCCTGGTTGGAGTAATGGTTTTGCCTTG TGGGGCCAAGGCACCCTGGTCACCGTCTCCTCA | 81 |
| mAb5 | HV-05 | CAGTCGGTGGAGGAGTCCGGGGGTCGCCTGGTCACGCCTGGGACA CCCCTGACACTCACCTGCACAGTCTCTGGATTCTCCCTCAGTACCT ACAATATGTGCTGGGTCCGCCAGGCTCCAGGGAAGGGCTTGGAAT GGGTCGGTTTCATTAATTCTGATGATAGCGCGTACTACGCGAGCTG GGCGAAAGGCCGCTTCACCTTCTCCAAGACCTCGACCACGGTGGA TCTGAAAATCGCCAGTCCGACAACCGAGGACACGGCCACCTATTT CTGTGCCAGATATGATTGGGATTATTATTATAGTCGGTTGGATCTC TGGGGCCCGGGCACCCTGGTCACCGTCTCCTCA | 82 |
| mAb6 | HV-06 | CAGCTGGAGGAGTCCGGGGGAGGCCTGGTCCAGCCTGGGGCATCC CTGACACTCACCTGCACAACTTCTGGATTCTCTCTCAGTGATAATT ATTTGTGTTGGGTCCGCCAGGCTCCAGGGCGTGGGCTGGAGTGGG TCGCATGCATTGGAATTGTTCTTCGTAGTACTGGTGCCACTTACTA CGCGAGCTGGGCGGAAGGCCGATTCACCATCTCCAAAACCTCGCC GACCACGGTGACTCTGGAGATGACCAGTCTGACAGCCGCGGACAC GGCCACCTACTTCTGTGCGCTAGATCTCGGATATGGTGGTCCTTTG TGGGGCCCGGGCACCCTGGTCACCGTCTCCTCA | 83 |

TABLE 7

Exemplary Anti-PACAP Light and Heavy Chain Nucleic Acid Sequences

| Antibody ID | Designation | Nucleic Acid Sequence | SEQ ID NO: |
|---|---|---|---|
| Light chains | | | |
| mAb1 | LC-01 | GCCGATGTCGTGATGACCCAGACTCCATCCCCCGTGTCTGCAGCTG TGGGAGGCACAGTCACCATCAATTGCCGGGCCAGTGAGGACATTG AAAGCTTTTTAGCCTGGTATCAGCAGAAACCAGGGCAGCCTCCCA AGCTCCTGATCTCCAGGACATCCACTCTGGAATCTGGGGTCTCATC GCGGTTCAAAGGCAGTGGATCGGGGACAGAGTTCATTCTCACCAT CAGCGACCTGGAGTGTGCCGATGCTGCCACTTACTACTGTCAATGT ACTGATGGTAGTAGTAGTAGTAGTAGTTATGGTTGGGATGCTTTCG GCGGAGGGACCGAGGTGGTGGTCAAAGGTGATCCAGTTGCACCTA CTGTCCTCCTCTTCCCACCATCTAGCGATGAGGTGGCAACTGGAAC AGTCACCATCGTGTGTGTGGCGAATAAATACTTTCCCGATGTCACC GTCACCTGGGAGGTGGATGGCACCACCCAAACAACTGGCATCGAG | 84 |

TABLE 7-continued

Exemplary Anti-PACAP Light and Heavy Chain Nucleic Acid Sequences

| Antibody ID | Designation | Nucleic Acid Sequence | SEQ ID NO: |
|---|---|---|---|
| | | AACAGTAAAACACCGCAGAATTCTGCAGATTGTACCTACAACCTC AGCAGCACTCTGACACTGACCAGCACACAGTACAACAGCCACAAA GAGTACACCTGCAAGGTGACCCAGGGCACGACCTCAGTCGTCCAG AGCTTCAGTAGGAAGAACTGT | |
| mAb2 | LC-02 | GCCGATGTCGTGATGACCCAGACTCCATCCCCCGTGTCTGCGCAGG TGGGAGGCACAGTCACCATCAATTGCCAGGCCAGTGAGAGCATTG ATAGTGACTTATCCTGGTATCAACAGAAACCAGGGCAGCCTCCCA AGCTCCTGATCTACAGGACATTCACTCTGGAATCTGGGGTCCCATC GCGGTTCAAAGGCAGTGGATCTGGGACAGACTACACTCTCACCAT CAGCGACCTGGAGTGTGCCGATGTGCTGCCATTTACTACTGTCAATGC ACTGATGGTAGTAGTATTAGTGGTAGTTATGGTTGGGATGCTTTCG GCGGAGGGACCGAGGTGGTGGTCAAAGGTGATCCAGTTGCACCTA CTGTCCTCCTCTTCCCACCATCTAGCGATGAGGTGGCAACTGGAAC AGTCACCATCGTGTGTGTGGCGAATAAATACTTTCCCGATGTCACC GTCACCTGGGAGGTGGATGGCACCACCCAAACAACTGGCATCGAG AACAGTAAAACACCGCAGAATTCTGCAGATTGTACCTACAACCTC AGCAGCACTCTGACACTGACCAGCACACAGTACAACAGCCACAAA GAGTACACCTGCAAGGTGACCCAGGGCACGACCTCAGTCGTCCAG AGCTTCAGTAGGAAGAACTGT | 85 |
| mAb3 | LC-03 | GCCGATGTCGTGATGACCCAGACTCCATCCCCCGTGTCTGCAGCTG TGGGAGGCACAGTCACCATCAATTGCCGGGCCAGTGAGGACATTG AAAGCTTTTTAGCCTGGTATCAGCAGAAACCAGGGCAGCCTCCCA AGCTCCTGATGTCCAGGACATCCACTCTGGAATCTGGGGTCCCATC GCGGTTCAAAGGCAGTGGATCTGGGACAGAGTTCACTCTCACCAT CAGCGACCTGGAGTGTGCCGATGTGCTGCCACATATTACTGTCAATGT ACTGATGGTAGTAGTAGTAGTAGTAGTTATGGTTGGGATGCTTTCG GCGGAGGGACCGAGGTGGTGGTCAAAGGTGATCCAGTTGCACCTA CTGTCCTCCTCTTCCCACCATCTAGCGATGAGGTGGCAACTGGAAC AGTCACCATCGTGTGTGTGGCGAATAAATACTTTCCCGATGTCACC GTCACCTGGGAGGTGGATGGCACCACCCAAACAACTGGCATCGAG AACAGTAAAACACCGCAGAATTCTGCAGATTGTACCTACAACCTC AGCAGCACTCTGACACTGACCAGCACACAGTACAACAGCCACAAA GAGTACACCTGCAAGGTGACCCAGGGCACGACCTCAGTCGTCCAG AGCTTCAGTAGGAAGAACTGT | 86 |
| mAb4 | LC-04 | GCTGACATTGTGATGACCCAGACTCCAGCCTCCGTGTCTGGAGCTG TGGGAGGCACAGTCACCATCAAGTGCCAGGCCAGTCAGAGCATTA GGAATGAATTATCCTGGTATCAGCAGAAACCAGGGCAGCCTCCCA AGCTCCTGATCTACAAGGCATCCACTCTGGCATCTGGGGTCCCATC GCGGTTCAGTGGCAGTGGATTTGGGACAGAGTTCACTCTCACCATC AGCGGTGTGCAGTGTGATGATGCTGCCACTTACTACTGTCAAAAC AATTATGGTACTAGGCGTAATAATTATGTTTTTCCTTTCGGCGGAG GGACCGAGGTGGTGGTCAAAGGTGATCCAGTTGCACCTACTGTCC TCCTCTTCCCACCATCTAGCGATGAGGTGGCAACTGGAACAGTCAC CATCGTGTGTGTGGCGAATAAATACTTTCCCGATGTCACCGTCACC TGGGAGGTGGATGGCACCACCCAAACAACTGGCATCGAGAACAGT AAAACACCGCAGAATTCTGCAGATTGTACCTACAACCTCAGCAGC ACTCTGACACTGACCAGCACACAGTACAACAGCCACAAAGAGTAC ACCTGCAAGGTGACCCAGGGCACGACCTCAGTCGTCCAGAGCTTC AGTAGGAAGAACTGT | 87 |
| mAb5 | LC-05 | GCTGACATCGTGCTGACCCAGACTCCAGCCTCCGTGTCTGCAGCTG TGGGAGGCACAGTCAGCATCAGTTGCCAGTCCAGTGAAAGTGTTT ATAATAACAACTACTTATCCTGGTTTCAGCAGAAACCAGGGCAGC CTCCCAAGCTCCTGATCTATGGTGCATCCACTCTGGCATCTGGGGT CCCATCGCGGTTTGAAGGCAGTGGATCTGGGACACAGTTCACTCTC ACCATCAGCGACGTGCAGTGTGATGATGCTGCCACTTACTACTGTC TAGGCGATTATATTATTATTGAGAATATTTCGGCGGAGGGACCGA GGTGGTGGTCAAAGGTGATCCAGTTGCACCTACTGTCCTCCTCTTC CCACCATCTAGCGATGAGGTGGCAACTGGAACAGTCACCATCGTG TGTGTGGCGAATAAATACTTTCCCGATGTCACCGTCACCTGGGAGG TGGATGGCACCACCCAAACAACTGGCATCGAGAACAGTAAAACAC CGCAGAATTCTGCAGATTGTACCTACAACCTCAGCAGCACTCTGAC ACTGACCAGCACACAGTACAACAGCCACAAAGAGTACACCTGCAA GGTGACCCAGGGCACGACCTCAGTCGTCCAGAGCTTCAGTAGGAA GAACTGT | 88 |
| mAb6 | LC-06 | GCGCAAGTGCTGACCCAGACTCCAGCCTCCGTGTCTGCGGCTGTG GGAGGCACAGTCACCATCAATTGCCAGGCCAGTCAGAGTGTTTAT AACAACAAAAATTTAGCCTGGTATCAGCAGAAACCAGGGCAGCC TCCCAAGCTCCTGATCTATTTTTCATCCACTCTGGCATCTGGGGTCC CATCGCGGTTCAGAGGCAGTGGATCTGGGACACAGTTCACTCTCA | 89 |

TABLE 7-continued

Exemplary Anti-PACAP Light and Heavy Chain Nucleic Acid Sequences

| Antibody ID | Designation | Nucleic Acid Sequence | SEQ ID NO: |
|---|---|---|---|
| | | CCATCAGTGGCGTGCAGTGTGGCGATGCTGCCACTTACTACTGTCT AGGCGAATTTGGTAGTATTTGGGCTTTCGGCGGAGGGACCGAGGT GGTGGTCAAAGGTGATCCAGTTGCACCTACTGTCCTCCTCTTCCCA CCATCTAGCGATGAGGTGGCAACTGGAACAGTCACCATCGTGTGT GTGGCGAATAAATACTTTCCCGATGTCACCGTCACCTGGGAGGTG GATGGCACCACCCAAACAACTGGCATCGAGAACAGTAAAACACCG CAGAATTCTGCAGATTGTACCTACAACCTCAGCAGCACTCTGACAC TGACCAGCACACAGTACAACAGCCACAAAGAGTACACCTGCAAGG TGACCCAGGGCACGACCTCAGTCGTCCAGAGCTTCAGTAGGAAGA ACTGT | |

Heavy chains

| mAb1 | HC-01 | CAGTCGTTGGAGGAGTCCGGGGGAGACCTGGTCAAGCCTGGGG CATCTCTGACACTCACCTGCAAAGCCTCTGGAATCGCCTTCAGTAA CGACTACATGTGCTGGGTCCGCCAGGCTCCAGGGAAGGGGCTGGA GTGGATCGCATGTATTTTTACTGGTAGTAGTGGTAGTACTTACTAC GCGAGCTGGGCGAAAGGTCGATTCACCATCTCCAAAACCTCGTCG ACCACGGTGACTCTGCAAATGACCAGTCTGACAGCCGCGGACACG GCCACCTATTTCTGTGCGAGAGATAGGGCTATTTCTGTACTTGGTT ATTTCTATGCTGCATACTTCTTTGACTTCTGGGGCCCAGGCACCCT GGTCACCGTCTCCTCAGGGCAACCTAAGGCTCCATCAGTCTTCCCA CTGGCCCCCTGCTGCGGGGACACACCCAGCTCCACGGTGACCTTG GGCTGCCTGGTCAAAGGCTACCTCCCGGAGCCAGTGACCGTGACC TGGAACTCGGGCACCCTCACCAATGGGGTACGCACCTTCCCGTCC GTCCGGCAGTCCTCAGGCCTCTACTCGCTGAGCAGCGTGGTGAGC GTGACCTCAAGCAGCCAGCCCGTCACCTGCAACGTGGCCCACCCA GCCACCAACACCAAAGTGGACAAGACCGTTGCGCCCTCGACATGC AGCAAGCCCACGTGCCCACCCCCTGAACTCCTGGGGGGACCGTCT GTCTTCATCTTCCCCCCAAAACCCAAGGACACCCTCATGATCTCAC GCACCCCCGAGGTCACATGCGTGGTGGTGGACGTGAGCCAGGATG ACCCCGAGGTGCAGTTCACATGGTACATAAACAACGAGCAGGTGC GCACCGCCCGGCCGCCGCTACGGGAGCAGCAGTTCAACAGCACGA TCCGCGTGGTCAGCACCCTCCCCATCGCGCACCAGGACTGGCTGA GGGGCAAGGAGTTCAAGTGCAAAGTCCACAACAAGGCACTCCCG GCCCCCATCGAGAAAACCATCTCCAAAGCCAGGGGCAGCCCCTG GAGCCGAAGGTCTACACCATGGGCCCTCCCCGGGAGGAGCTGAGC AGCAGGTCGGTCAGCCTGACCTGCATGATCAACGGCTTCTACCCTT CCGACATCTCGGTGGAGTGGGAGAAGAACGGGAAGGCAGAGGAC AACTACAAGACCACGCCGGCCGTGCTGGACAGCGACGGCTCCTAC TTCCTCTACAGCAAGCTCTCAGTGCCCACGAGTGAGTGGCAGCGG GGCGACGTCTTCACCTGCTCCGTGATGCACGAGGCCTTGCACAACC ACTACACGCAGAAGTCCATCTCCCGCTCTCCGGGTAAA | 90 |
| mAb2 | HC-02 | CAGTCGTTGGAGGAGTCCGGGGGAGGCCTGGTCCAGCCTGAGG GATCCCTGACACTCACCTGCACAGCTTCTGGATTCTCCTTCAATAG CAGCTCCTACATGTGCTGGGTCCGCCAGGCTCCAGGGAAGGGGCT GGAGTGGATCGGATGCATTTTTACTGGTAGTAGTGGTAATACCTAC TACGCGACCTGGGCGCAAGGTCGATTCACCATCTCCAAGACCTCG ACCACGGTGACTCTGGAAATGACCAGTCTGACAGCCGCGGACACG GCCACCTATTTCTGTGCGAGAGATAGGGCTTATTTTTTGGTTGGTT ATTTCTATGCTACATATTATTTGACTTATGGGGCCCAGGCACCCT GGTCACCGTCTCCTCAGGGCAACCTAAGGCTCCATCAGTCTTCCCA CTGGCCCCCTGCTGCGGGGACACACCCTCTAGCACGGTGACCTTG GGCTGCCTGGTCAAAGGCTACCTCCCGGAGCCAGTGACCGTGACC TGGAACTCGGGCACCCTCACCAATGGGGTACGCACCTTCCCGTCC GTCCGGCAGTCCTCAGGCCTCTACTCGCTGAGCAGCGTGGTGAGC GTGACCTCAAGCAGCCAGCCCGTCACCTGCAACGTGGCCCACCCA GCCACCAACACCAAAGTGGACAAGACCGTTGCGCCCTCGACATGC AGCAAGCCCACGTGCCCACCCCCTGAACTCCTGGGGGGACCGTCT GTCTTCATCTTCCCCCCAAAACCCAAGGACACCCTCATGATCTCAC GCACCCCCGAGGTCACATGCGTGGTGGTGGACGTGAGCCAGGATG ACCCCGAGGTGCAGTTCACATGGTACATAAACAACGAGCAGGTGC GCACCGCCCGGCCGCCGCTACGGGAGCAGCAGTTCAACAGCACGA TCCGCGTGGTCAGCACCCTCCCCATCGCGCACCAGGACTGGCTGA GGGGCAAGGAGTTCAAGTGCAAAGTCCACAACAAGGCACTCCCG GCCCCCATCGAGAAAACCATCTCCAAAGCCAGGGGCAGCCCCTG GAGCCGAAGGTCTACACCATGGGCCCTCCCCGGGAGGAGCTGAGC AGCAGGTCGGTCAGCCTGACCTGCATGATCAACGGCTTCTACCCTT CCGACATCTCGGTGGAGTGGGAGAAGAACGGGAAGGCAGAGGAC AACTACAAGACCACGCCGGCCGTGCTGGACAGCGACGGCTCCTAC TTCCTCTACAGCAAGCTCTCAGTGCCCACGAGTGAGTGGCAGCGG GGCGACGTCTTCACCTGCTCCGTGATGCACGAGGCCTTGCACAACC ACTACACGCAGAAGTCCATCTCCCGCTCTCCGGGTAAA | 91 |

TABLE 7-continued

Exemplary Anti-PACAP Light and Heavy Chain Nucleic Acid Sequences

| Antibody ID | Designation | Nucleic Acid Sequence | SEQ ID NO: |
|---|---|---|---|
| mAb3 | HC-03 | CAGTCGTTGGAGGAGTCCGGGGGAGGCCTGGTCCAGCCTGGGG CATCTCTGACACTCACCTGTACAGCCTCTGGATTCTCCTTCAGTAG CAACTACTACATGTGCTGGGTCCGCCAGGCTCCAGGGAAGGGGCT GGAGTGGATCGCATGCATTTTTACTGGTAGTAGTGGTAGCACTTAC TACGCGAGCTGGGCGAAAGGCCGATTCACCATCTCCAAAACCTCG TCGACCACGGTGACTCTGCACGTGACCAGTCTGACAGCCGCGGAC ACGGCCACCTATTTCTGTGCGAGAGATAGGGCTTTGTCTGTTGTTG GTTATTTCTATGCTGCATACTACTTTGACTTCTGGGGCCCAGGCAC CCTGGTCACCGTCTCCTCAGGGCAACCTAAGGCTCCATCAGTCTTC CCACTGGCCCCCTGCTGCGGGGACACACCCTCTAGCACGGTGACC TTGGGCTGCCTGGTCAAAGGCTACCTCCCGGAGCCAGTGACCGTG ACCTGGAACTCGGGCACCCTCACCAATGGGGTACGCACCTTCCCG TCCGTCCGGCAGTCCTCAGGCCTCTACTCGCTGAGCAGCGTGGTGA GCGTGACCTCAAGCAGCCAGCCCGTCACCTGCAACGTGGCCCACC CAGCCACCAACACCAAAGTGGACAAGACCGTTGCGCCCTCGACAT GCAGCAAGCCCACGTGCCCACCCCCTGAACTCCTGGGGGGACCGT CTGTCTTCATCTTCCCCCCAAAACCCAAGGACACCCTCATGATCTC ACGCACCCCCGAGGTCACATGCGTGGTGGTGGACGTGAGCCAGGA TGACCCCGAGGTGCAGTTCACATGGTACATAAACAACGAGCAGGT GCGCACCGCCCGGCCGCCGCTACGGGAGCAGCAGTTCAACAGCAC GATCCGCGTGGTCAGCACCCTCCCCATCGCGCACCAGGACTGGCT GAGGGGCAAGGAGTTCAAGTGCAAAGTCCACAACAAGGCACTCCC GGCCCCCATCGAGAAAACCATCTCCAAAGCCAGAGGGCAGCCCCT GGAGCCGAAGGTCTACACCATGGGCCCTCCCCGGGAGGAGCTGAG CAGCAGGTCGGTCAGCCTGACCTGCATGATCAACGGCTTCTACCCT TCCGACATCTCGGTGGAGTGGGAGAAGAACGGGAAGGCAGAGGA CAACTACAAGACCACGCCGGCCGTGCTGGACAGCGACGGCTCCTA CTTCCTCTACAGCAAGCTCTCAGTGCCCACGAGTGAGTGGCAGCG GGGCGACGTCTTCACCTGCTCCGTGATGCACGAGGCCTTGCACAA CCACTACACGCAGAAGTCCATCTCCCGCTCTCCGGGTAAA | 92 |
| mAb4 | HC-04 | CAGTCGGTGGAGGAGTCCGGGGGTCGCCTGGTCACGCCTGGGACA CCCCTGACACTCACCTGCACAGCCTCTGGAATCGACCTCAGTAGCT ATGCAATGATCTGGGTCCGCCAGGCTCCAGGAGAGGGACTGGAAT ACATCGGATTCATTGATGCTGGTGATGGTAACACTTACTACGCGAG CTGGGCAAAAGGCCGATTCACCATCTCCAAAACCTCGACCACGGT GGATCTGAAAATCACCAGTCCGACAACCGAGGACACGGCCACCTA TTTCTGTGCCAGAGGAGATCCTGGTTGGAGTAATGGTTTTGCCTTG TGGGGCCAAGGCACCCTGGTCACCGTCTCCTCAGGGCAACCTAAG GCTCCATCAGTCTTCCCACTGGCCCCCTGCTGCGGGGACACACCCT CTAGCACGGTGACCTTGGGCTGCCTGGTCAAAGGCTACCTCCCGG AGCCAGTGACCGTGACCTGGAACTCGGGCACCCTCACCAATGGGG TACGCACCTTCCCGTCCGTCCGGCAGTCCTCAGGCCTCTACTCGCT GAGCAGCGTGGTGAGCGTGACCTCAAGCAGCCAGCCCGTCACCTG CAACGTGGCCCACCCAGCCACCAACACCAAAGTGGACAAGACCGT TGCGCCCTCGACATGCAGCAAGCCCACGTGCCCACCCCCTGAACT CCTGGGGGGACCGTCTGTCTTCATCTTCCCCCCAAAACCCAAGGAC ACCCTCATGATCTCACGCACCCCCGAGGTCACATGCGTGGTGGTG GACGTGAGCCAGGATGACCCCGAGGTGCAGTTCACATGGTACATA AACAACGAGCAGGTGCGCACCGCCCGGCCGCCGCTACGGGAGCA GCAGTTCAACAGCACGATCCGCGTGGTCAGCACCCTCCCCATCGC GCACCAGGACTGGCTGAGGGGCAAGGAGTTCAAGTGCAAAGTCCA CAACAAGGCACTCCCGGCCCCCATCGAGAAAACCATCTCCAAAGC CAGAGGGCAGCCCCTGGAGCCGAAGGTCTACACCATGGGCCCTCC CCGGGAGGAGCTGAGCAGCAGGTCGGTCAGCCTGACCTGCATGAT CAACGGCTTCTACCCTTCCGACATCTCGGTGGAGTGGGAGAAGAA CGGGAAGGCAGAGGACAACTACAAGACCACGCCGGCCGTGCTGG ACAGCGACGGCTCCTACTTCCTCTACAGCAAGCTCTCAGTGCCCAC GAGTGAGTGGCAGCGGGGCGACGTCTTCACCTGCTCCGTGATGCA CGAGGCCTTGCACAACCACTACACGCAGAAGTCCATCTCCCGCTCT CCGGGTAAA | 93 |
| mAb5 | HC-05 | CAGTCGGTGGAGGAGTCCGGGGGTCGCCTGGTCACGCCTGGGACA CCCCTGACACTCACCTGCACAGTCTCTGGATTCTCCCTCAGTACCT ACAATATGTGCTGGGTCCGCCAGGCTCCAGGGAAGGGCTTGGAAT GGGTCGGTTTCATTAATTCTGATGATAGCGCGTACTACGCGAGCTG GGCGAAAGGCCGCTTCACCTTCTCCAAGACCTCGACCACGGTGGA TCTGAAAATCGCCAGTCCGACAACCGAGGACACGGCCACCTATTT CTGTGCCAGATATGATTGGGATTATTATTATAGTCGGTTGGATCTC TGGGGCCGGGCACCCTGGTCACCGTCTCCTCAGGGCAACCTAAG GCTCCATCAGTCTTCCCACTGGCCCCCTGCTGCGGGGACACACCCT CTAGCACGGTGACCTTGGGCTGCCTGGTCAAAGGCTACCTCCCGG AGCCAGTGACCGTGACCTGGAACTCGGGCACCCTCACCAATGGGG | 94 |

TABLE 7-continued

Exemplary Anti-PACAP Light and Heavy Chain Nucleic Acid Sequences

| Antibody ID | Designation | Nucleic Acid Sequence | SEQ ID NO: |
|---|---|---|---|
| | | TACGCACCTTCCCGTCCGTCCGGCAGTCCTCAGGCCTCTACTCGCT GAGCAGCGTGGTGAGCGTGACCTCAAGCAGCCAGCCCGTCACCTG CAACGTGGCCCACCCAGCCACCAACACCAAAGTGGACAAGACCGT TGCGCCCTCGACATGCAGCAAGCCCACGTGCCCACCCCCTGAACT CCTGGGGGGACCGTCTGTCTTCATCTTCCCCCCAAAACCCAAGGAC ACCCTCATGATCTCACGCACCCCCGAGGTCACATGCGTGGTGGTG GACGTGAGCCAGGATGACCCCGAGGTGCAGTTCACATGGTACATA AACAACGAGCAGGTGCGCACCGCCCGGCCGCCGCTACGGGAGCA GCAGTTCAACAGCACGATCCGCGTGGTCAGCACCCTCCCCATCGC GCACCAGGACTGGCTGAGGGGCAAGGAGTTCAAGTGCAAAGTCCA CAACAAGGCACTCCCGGCCCCCATCGAGAAAACCATCTCCAAAGC CAGAGGGCAGCCCCTGGAGCCGAAGGTCTACACCATGGGCCCTCC CCGGGAGGAGCTGAGCAGCAGGTCGGTCAGCCTGACCTGCATGAT CAACGGCTTCTACCCTTCCGACATCTCGGTGGAGTGGGAGAAGAA CGGGAAGGCAGAGGACAACTACAAGACCACGCCGGCCGTGCTGG ACAGCGACGGCTCCTACTTCCTCTACAGCAAGCTCTCAGTGCCCAC GAGTGAGTGGCAGCGGGGCGACGTCTTCACCTGCTCCGTGATGCA CGAGGCCTTGCACAACCACTACACGCAGAAGTCCATCTCCCGCTCT CCGGGTAAA | |
| mAb6 | HC-06 | CAGCTGGAGGAGTCCGGGGGAGGCCTGGTCCAGCCTGGGGCATCC CTGACACTCACCTGCACAACTTCTGGATTCTCTCTCAGTGATAATT ATTTGTGTTGGGTCCGCCAGGCTCCAGGGCGTGGGCTGGAGTGGG TCGCATGCATTGGAATTGTTCTTCGTAGTACTGGTGCCACTTACTA CGCGAGCTGGGCGGAAGGCCGATTCACCATCTCCAAAACCTCGCC GACCACGGTGACTCTGGAGATGACCAGTCTGACAGCCGCGGACAC GGCCACCTACTTCTGTGCGCTAGATCTCGGATATGGTGGTCCTTTG TGGGGCCCGGGCACCCTGGTCACCGTCTCCTCAGGGCAACCTAAG GCTCCATCAGTCTTCCCACTGGCCCCCTGCTGCGGGGACACACCCT CTAGCACGGTGACCTTGGGCTGCCTGGTCAAAGGCTACCTCCCGG AGCCAGTGACCGTGACCTGGAACTCGGGCACCCTCACCAATGGGG TACGCACCTTCCCGTCCGTCCGGCAGTCCTCAGGCCTCTACTCGCT GAGCAGCGTGGTGAGCGTGACCTCAAGCAGCCAGCCCGTCACCTG CAACGTGGCCCACCCAGCCACCAACACCAAAGTGGACAAGACCGT TGCGCCCTCGACATGCAGCAAGCCCACGTGCCCACCCCCTGAACT CCTGGGGGGACCGTCTGTCTTCATCTTCCCCCCAAAACCCAAGGAC ACCCTCATGATCTCACGCACCCCCGAGGTCACATGCGTGGTGGTG GACGTGAGCCAGGATGACCCCGAGGTGCAGTTCACATGGTACATA AACAACGAGCAGGTGCGCACCGCCCGGCCGCCGCTACGGGAGCA GCAGTTCAACAGCACGATCCGCGTGGTCAGCACCCTCCCCATCGC GCACCAGGACTGGCTGAGGGGCAAGGAGTTCAAGTGCAAAGTCCA CAACAAGGCACTCCCGGCCCCCATCGAGAAAACCATCTCCAAAGC CAGAGGGCAGCCCCTGGAGCCGAAGGTCTACACCATGGGCCCTCC CCGGGAGGAGCTGAGCAGCAGGTCGGTCAGCCTGACCTGCATGAT CAACGGCTTCTACCCTTCCGACATCTCGGTGGAGTGGGAGAAGAA CGGGAAGGCAGAGGACAACTACAAGACCACGCCGGCCGTGCTGG ACAGCGACGGCTCCTACTTCCTCTACAGCAAGCTCTCAGTGCCCAC GAGTGAGTGGCAGCGGGGCGACGTCTTCACCTGCTCCGTGATGCA CGAGGCCTTGCACAACCACTACACGCAGAAGTCCATCTCCCGCTCT CCGGGTAAA | 95 |

Isolated nucleic acids encoding the anti-PACAP binding domain of the antigen binding proteins of the invention may comprise a nucleotide sequence that is at least 80% identical, at least 90% identical, at least 95% identical, or at least 98% identical to any of the nucleotide sequences listed in Table 6. In some embodiments, an isolated nucleic acid encoding an anti-PACAP light chain variable region comprises a sequence that is at least 80% identical, at least 90% identical, at least 95% identical, or at least 98% identical to a sequence selected from SEQ ID NOs: 72 to 77. In certain embodiments, an isolated nucleic acid encoding an anti-PACAP light chain variable region comprises a sequence selected from SEQ ID NOs: 72 to 77. In related embodiments, an isolated nucleic acid encoding an anti-PACAP heavy chain variable region comprises a sequence that is at least 80% identical, at least 90% identical, at least 95% identical, or at least 98% identical to a sequence selected from SEQ ID NOs: 78 to 83. In other related embodiments, an isolated nucleic acid encoding an anti-PACAP heavy chain variable region comprises a sequence selected from SEQ ID NOs: 78 to 83.

In embodiments in which the antigen binding protein of the invention is an antibody, the isolated nucleic acid encoding the antibody light chain and heavy chain may comprise a nucleotide sequence that is at least 60% identical, at least 70% identical, at least 80% identical, at least 90% identical, at least 95% identical, or at least 98% identical to any of the nucleotide sequences listed in Table 7. In certain embodiments, the isolated nucleic acid encoding a light chain of an anti-PACAP antibody of the invention comprises a sequence that is at least 60% identical, at least 70% identical, at least 80% identical, at least 90% identical, at least 95% identical, or at least 98% identical to a sequence selected from SEQ ID NOs: 84 to 89. In some embodiments, the isolated nucleic acid encoding a light chain of an anti-PACAP antibody comprises a sequence selected from SEQ ID NOs: 84 to 89.

In these and other embodiments, the isolated nucleic acid encoding a heavy chain of an anti-PACAP antibody of the invention may comprise a nucleotide sequence that is at least 60% identical, at least 70% identical, at least 80% identical, at least 90% identical, at least 95% identical, or at least 98% identical to a sequence selected from SEQ ID NOs: 90 to 95. In certain embodiments, the isolated nucleic acid encoding a heavy chain of an anti-PACAP antibody of the invention comprises a sequence selected from SEQ ID NOs: 90 to 95.

The nucleic acid sequences provided in Tables 6 and 7 are exemplary only. As will be appreciated by those in the art, due to the degeneracy of the genetic code, an extremely large number of nucleic acids may be made, all of which encode the CDRs, variable regions, and heavy and light chains or other components of the antigen binding proteins described herein. Thus, having identified a particular amino acid sequence, those skilled in the art could make any number of different nucleic acids, by simply modifying the sequence of one or more codons in a way which does not change the amino acid sequence of the encoded protein.

The present invention also includes vectors comprising one or more nucleic acids encoding one or more components of the antigen binding proteins of the invention (e.g. variable regions, light chains, and heavy chains). The term "vector" refers to any molecule or entity (e.g., nucleic acid, plasmid, bacteriophage or virus) used to transfer protein coding information into a host cell. Examples of vectors include, but are not limited to, plasmids, viral vectors, non-episomal mammalian vectors and expression vectors, for example, recombinant expression vectors. The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. For instance, in some embodiments, signal peptide sequences may be appended/fused to the amino terminus of any of the polypeptides sequences listed in Tables 2 and 5. In certain embodiments, a signal peptide having the amino acid sequence of MDMRVPAQLLGLLLLWLRGARC (SEQ ID NO: 96) is fused to the amino terminus of any of the polypeptide sequences in Tables 2 and 5. In other embodiments, a signal peptide having the amino acid sequence of MAWALLLLTLLTQGTGSWA (SEQ ID NO: 97) is fused to the amino terminus of any of the polypeptide sequences in Tables 2 and 5. In still other embodiments, a signal peptide having the amino acid sequence of MTCSPLLLTL-LIHCTGSWA (SEQ ID NO: 98) is fused to the amino terminus of any of the polypeptide sequences in Tables 2 and 5. Other suitable signal peptide sequences that can be fused to the amino terminus of the polypeptide sequences described herein include: MEAPAQLLFLLLLWLPDTTG (SEQ ID NO: 99), MEWTWRVLFLVAAATGAHS (SEQ ID NO: 100), METPAQLLFLLLLWLPDTTG (SEQ ID NO: 101), METPAQLLFLLLLWLPDTTG (SEQ ID NO: 102), MKHLWFFLLLVAAPRWVLS (SEQ ID NO: 103), MEWSWVFLFFLSVTTGVHS (SEQ ID NO: 104), MDI-RAPTQLLGLLLLWLPGAKC (SEQ ID NO: 105), MDI-RAPTQLLGLLLLWLPGARC (SEQ ID NO: 106), MDTRAPTQLLGLLLLWLPGATF (SEQ ID NO: 107), MDTRAPTQLLGLLLLWLPGARC (SEQ ID NO: 108), METGLRWLLLVAVLKGVQC (SEQ ID NO: 109), METGLRWLLLVAVLKGVQCQE (SEQ ID NO: 110), and MDMRAPTQLLGLLLLWLPGARC (SEQ ID NO: 111). Other signal peptides are known to those of skill in the art and may be fused to any of the polypeptide chains listed in Tables 2 and 5, for example, to facilitate or optimize expression in particular host cells.

Typically, expression vectors used in the host cells to produce the antigen binding proteins of the invention will contain sequences for plasmid maintenance and for cloning and expression of exogenous nucleotide sequences encoding the components of the antigen binding proteins. Such sequences, collectively referred to as "flanking sequences," in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the polypeptide coding sequence; the oligonucleotide tag sequence encodes polyHis (such as hexaHis), FLAG, HA (hemaglutinin influenza virus), myc, or another "tag" molecule for which commercially available antibodies exist. This tag is typically fused to the polypeptide upon expression of the polypeptide, and can serve as a means for affinity purification or detection of the polypeptide from the host cell. Affinity purification can be accomplished, for example, by column chromatography using antibodies against the tag as an affinity matrix. Optionally, the tag can subsequently be removed from the purified polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using routine methods for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using known methods for nucleic acid synthesis.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as one or more components of the antigen binding proteins described herein. As a result, increased quantities of a polypeptide are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the polypeptide. The term "operably linked" as used herein refers to the linkage of two or more nucleic acid sequences in such a manner that a nucleic acid molecule capable of directing the transcription of a given gene and/or the synthesis of a desired protein molecule is produced. For example, a control sequence in a vector that is "operably linked" to a protein coding sequence is ligated thereto so that expression of the protein coding sequence is achieved under conditions compatible with the transcriptional activity of the control sequences. More specifically, a promoter and/or enhancer sequence, including any combination of cis-acting transcriptional control elements is operably linked to a coding sequence if it stimulates or modulates the transcription of the coding sequence in an appropriate host cell or other expression system.

Promoters are non-transcribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known. A suitable promoter is operably linked to the DNA encoding e.g., heavy chain, light chain, or other component of the antigen binding proteins of the invention, by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thornsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78: 1444-1445); promoter and regulatory sequences from the metallothionine gene Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315: 115-122); the immunoglobulin gene control region that is active in lymphoid cells (Grosschedl et al., 1984, Cell 38:647-658; Adames et al., 1985, Nature 318:533-538; Alexander et al., 1987, Mol. Cell. Biol. 7: 1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-fetoprotein gene control region that is active in liver (Krumlauf et al., 1985, Mol. Cell. Biol. 5: 1639-1648; Hammer et al., 1987, Science 253:53-58); the alpha 1-antitrypsin gene control region that is active in liver (Kelsey et al., 1987, Genes and Devel. 1: 161-171); the beta-globin gene control region that is active in myeloid cells (Mogram et al, 1985, Nature 315:338-340; Kollias et al, 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234: 1372-1378).

An enhancer sequence may be inserted into the vector to increase transcription of DNA encoding a component of the antigen binding proteins (e.g., light chain, heavy chain, or variable regions) by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-fetoprotein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antigen binding protein. The choice of signal peptide or leader depends on the type of host cells in which the antibody binding protein is to be produced, and a heterologous signal sequence can replace the native signal sequence. Examples of signal peptides are described above. Other signal peptides that are functional in mammalian host cells include the signal sequence for interleukin-7 (IL-7) described in U.S. Pat. No. 4,965,195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The expression vectors that are provided may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art. The expression vectors can be introduced into host cells to thereby produce proteins, including fusion proteins, encoded by nucleic acids as described herein.

After the vector has been constructed and the one or more nucleic acid molecules encoding the components of the antigen binding proteins described herein has been inserted into the proper site(s) of the vector or vectors, the completed vector(s) may be inserted into a suitable host cell for amplification and/or polypeptide expression. Thus, the present invention encompasses an isolated host cell comprising one or more expression vectors encoding the components of the antigen binding proteins. The term "host cell" as used herein refers to a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. A host cell that comprises an isolated nucleic acid of the invention, preferably operably linked to at least one expression control sequence (e.g. promoter or enhancer), is a "recombinant host cell."

The transformation of an expression vector for an antigen binding protein into a selected host cell may be accomplished by well-known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus*, such as *B. subtilis* and *B. licheniformis, Pseudomonas*, and *Streptomyces*. Eukaryotic microbes such as filamentous fungi or yeast are suitable cloning or expression hosts for recombinant polypeptides. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces*, such as *Schwanniomyces occidentalis*; and filamentous fungi, such as, e.g., *Neurrospora, Penicillium, Tolypocladium*, and *Aspergillus* hosts such as *A. nidulans* and *A. niger*.

Host cells for the expression of glycosylated antigen binding proteins can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of antigen binding proteins from such cells has become routine procedure. Mammalian cell lines available as hosts for expression are well known in the art and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68, 1982); MRC 5 cells or FS4 cells; mammalian myeloma cells, and a number of other cell lines. In certain embodiments, cell lines may be selected through determining which cell lines have high expression levels and constitutively produce antigen binding proteins with PACAP binding properties. In another embodiment, a cell line from the B cell lineage that does not make its own antibody but has a capacity to make and secrete a heterologous antibody can be selected. CHO cells are preferred host cells in some embodiments for expressing the antigen binding proteins of the invention.

Host cells are transformed or transfected with the above-described nucleic acids or vectors for production of antigen binding proteins and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of antigen binding proteins. Thus, the present invention also provides a method for producing an antigen binding protein described herein, such as a monoclonal antibody or binding fragment thereof, comprising culturing a host cell comprising one or more expression vectors described herein in a culture medium under conditions permitting expression of the antigen binding protein encoded by the one or more expression vectors; and recovering the antigen binding protein from the culture medium or host cell.

The host cells used to produce the antigen binding proteins of the invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham et al., Meth. Enz. 58: 44, 1979; Barnes et al., Anal. Biochem. 102: 255, 1980; U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinary skilled artisan.

Upon culturing the host cells, the antigen binding protein can be produced intracellularly, in the periplasmic space, or directly secreted into the medium. If the antigen binding protein is produced intracellularly, as a first step, the particulate debris, either host cells or lysed fragments, is removed, for example, by centrifugation or ultrafiltration. The antigen binding protein can be purified using, for example, hydroxyapatite chromatography, cation or anion exchange chromatography, or preferably affinity chromatography, using the antigen(s) of interest or protein A or protein G as an affinity ligand. Protein A can be used to purify proteins that include polypeptides that are based on human γ1, γ2, or γ4 heavy chains (Lindmark et al., J. Immunol. Meth. 62: 1-13, 1983). Protein G is recommended for all mouse isotypes and for human γ3 (Guss et al., EMBO J. 5: 15671575, 1986). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a CH3 domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the particular antigen binding protein to be recovered.

In certain embodiments, the invention provides a composition (e.g. a pharmaceutical composition) comprising one or a plurality of the antigen binding proteins of the invention (e.g. monoclonal antibodies or binding fragments thereof) together with pharmaceutically acceptable diluents, carriers, excipients, solubilizers, emulsifiers, preservatives, and/or adjuvants. Pharmaceutical compositions of the invention include, but are not limited to, liquid, frozen, and lyophilized compositions. "Pharmaceutically-acceptable" refers to molecules, compounds, and compositions that are non-toxic to human recipients at the dosages and concentrations employed and/or do not produce allergic or adverse reactions when administered to humans. In some embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Methods and suitable materials for formulating molecules for therapeutic use are known in the pharmaceutical arts, and are described, for example, in REMINGTON'S PHARMACEUTICAL SCIENCES, 18th Edition, (A. R. Genrmo, ed.), 1990, Mack Publishing Company.

In some embodiments, the pharmaceutical composition of the invention comprises a standard pharmaceutical carrier, such as a sterile phosphate buffered saline solution, bacteriostatic water, and the like. A variety of aqueous carriers may be used, e.g., water, buffered water, 0.4% saline, 0.3% glycine and the like, and may include other proteins for enhanced stability, such as albumin, lipoprotein, globulin, etc., subjected to mild chemical modifications or the like.

Exemplary concentrations of the antigen binding proteins in the formulation may range from about 0.1 mg/ml to about 200 mg/ml or from about 0.1 mg/mL to about 50 mg/mL, or from about 0.5 mg/mL to about 25 mg/mL, or alternatively from about 2 mg/mL to about 10 mg/mL. An aqueous formulation of the antigen binding protein may be prepared in a pH-buffered solution, for example, at pH ranging from about 4.5 to about 6.5, or from about 4.8 to about 5.5, or alternatively about 5.0. Examples of buffers that are suitable for a pH within this range include acetate (e.g. sodium acetate), succinate (such as sodium succinate), gluconate, histidine, citrate and other organic acid buffers. The buffer concentration can be from about 1 mM to about 200 mM, or from about 10 mM to about 60 mM, depending, for example, on the buffer and the desired isotonicity of the formulation.

A tonicity agent, which may also stabilize the antigen binding protein, may be included in the formulation. Exemplary tonicity agents include polyols, such as mannitol, sucrose or trehalose. Preferably the aqueous formulation is isotonic, although hypertonic or hypotonic solutions may be suitable. Exemplary concentrations of the polyol in the formulation may range from about 1% to about 15% w/v.

A surfactant may also be added to the antigen binding protein formulation to reduce aggregation of the formulated antigen binding protein and/or minimize the formation of particulates in the formulation and/or reduce adsorption. Exemplary surfactants include nonionic surfactants such as polysorbates (e.g. polysorbate 20 or polysorbate 80) or poloxamers (e.g. poloxamer 188). Exemplary concentrations of surfactant may range from about 0.001% to about 0.5%, or from about 0.005% to about 0.2%, or alternatively from about 0.004% to about 0.01% w/v.

In one embodiment, the formulation contains the above-identified agents (i.e. antigen binding protein, buffer, polyol and surfactant) and is essentially free of one or more preservatives, such as benzyl alcohol, phenol, m-cresol, chlorobutanol and benzethonium chloride. In another embodiment, a preservative may be included in the formulation, e.g., at concentrations ranging from about 0.1% to about 2%, or alternatively from about 0.5% to about 1%. One or more other pharmaceutically acceptable carriers, excipients or stabilizers such as those described in REMINGTON'S PHARMACEUTICAL SCIENCES, 18th Edition, (A. R. Genrmo, ed.), 1990, Mack Publishing Company, may be included in the formulation provided that they do not adversely affect the desired characteristics of the formulation.

Therapeutic formulations of the antigen binding protein are prepared for storage by mixing the antigen binding protein having the desired degree of purity with optional physiologically acceptable carriers, excipients or stabilizers (REMINGTON'S PHARMACEUTICAL SCIENCES, 18th Edition, (A. R. Genrmo, ed.), 1990, Mack Publishing Company), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, maltose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In one embodiment, a suitable formulation of the claimed invention contains an isotonic buffer such as a phosphate, acetate, or TRIS buffer in combination with a tonicity agent, such as a polyol, sorbitol, sucrose or sodium chloride, which tonicifies and stabilizes. One example of such a tonicity agent is 5% sorbitol or sucrose. In addition, the formulation could optionally include a surfactant at 0.01% to 0.02% wt/vol, for example, to prevent aggregation or improve stability. The pH of the formulation may range from 4.5-6.5 or 4.5 to 5.5. Other exemplary descriptions of pharmaceutical formulations for antigen binding proteins may be found in US Patent Publication No. 2003/0113316 and U.S. Pat. No. 6,171,586, each of which is hereby incorporated by reference in its entirety.

Suspensions and crystal forms of antigen binding proteins are also contemplated. Methods to make suspensions and crystal forms are known to one of skill in the art.

The formulations to be used for in vivo administration must be sterile. The compositions of the invention may be sterilized by conventional, well known sterilization techniques. For example, sterilization is readily accomplished by filtration through sterile filtration membranes. The resulting solutions may be packaged for use or filtered under aseptic conditions and lyophilized, the lyophilized preparation being combined with a sterile solution prior to administration.

The process of freeze-drying is often employed to stabilize polypeptides for long-term storage, particularly when the polypeptide is relatively unstable in liquid compositions. A lyophilization cycle is usually composed of three steps: freezing, primary drying, and secondary drying (see Williams and Polli, Journal of Parenteral Science and Technology, Volume 38, Number 2, pages 48-59, 1984). In the freezing step, the solution is cooled until it is adequately frozen. Bulk water in the solution forms ice at this stage. The ice sublimes in the primary drying stage, which is conducted by reducing chamber pressure below the vapor pressure of the ice, using a vacuum. Finally, sorbed or bound water is removed at the secondary drying stage under reduced chamber pressure and an elevated shelf temperature. The process produces a material known as a lyophilized cake. Thereafter the cake can be reconstituted prior to use.

The standard reconstitution practice for lyophilized material is to add back a volume of pure water (typically equivalent to the volume removed during lyophilization), although dilute solutions of antibacterial agents are sometimes used in the production of pharmaceuticals for parenteral administration (see Chen, Drug Development and Industrial Pharmacy, Volume 18: 1311-1354, 1992).

Excipients have been noted in some cases to act as stabilizers for freeze-dried products (see Carpenter et al., Volume 74: 225-239, 1991). For example, known excipients include polyols (including mannitol, sorbitol and glycerol); sugars (including glucose and sucrose); and amino acids (including alanine, glycine and glutamic acid).

In addition, polyols and sugars are also often used to protect polypeptides from freezing and drying-induced damage and to enhance the stability during storage in the dried state. In general, sugars, in particular disaccharides, are effective in both the freeze-drying process and during storage. Other classes of molecules, including mono- and disaccharides and polymers such as PVP, have also been reported as stabilizers of lyophilized products.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Sustained-release preparations may be prepared. Suitable examples of sustained-release preparations include semipermeable matrices of solid hydrophobic polymers containing the antigen binding protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The formulations of the invention may be designed to be short-acting, fast-releasing, long-acting, or sustained-releasing as described herein. Thus, the pharmaceutical formulations may also be formulated for controlled release or for slow release.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

The antigen binding protein is administered by any suitable means, including parenteral, subcutaneous, intraperitoneal, intrapulmonary, and intranasal, and, if desired for local treatment, intralesional administration. Parenteral administration includes intravenous, intraarterial, intraperitoneal, intramuscular, intradermal or subcutaneous administration. In addition, the antigen binding protein is suitably administered by pulse infusion, particularly with declining doses of the antigen binding protein. Preferably, the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site. Most preferably, the antigen binding protein of the invention is administered intravenously or subcutaneously in a physiological solution at a dose ranging between 0.01 mg/kg to 100 mg/kg at a frequency ranging from daily to weekly to monthly (e.g. every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of once per week, once every two weeks, or once a month.

The antigen binding proteins described herein (e.g. monoclonal antibodies and binding fragments thereof) are useful for treating or ameliorating a condition associated with the biological activity of PACAP in a patient in need thereof. As used herein, the term "treating" or "treatment" is an intervention performed with the intention of preventing the development or altering the pathology of a disorder. Accordingly, "treatment" refers to both therapeutic treatment and prophylactic or preventative measures. Those in need of treatment include those already diagnosed with or suffering from the disorder or condition as well as those in which the disorder or condition is to be prevented. "Treatment" includes any indicia of success in the amelioration of an injury, pathology or condition, including any objective or subjective parameter such as abatement, remission, diminishing of symptoms, or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, self-reporting by a patient, neuropsychiatric exams, and/or a psychiatric evaluation.

Accordingly, in some embodiments, the present invention provides a method for treating or preventing a condition associated with the biological activity of PACAP, such as activation of VPAC1, VPAC2, and/or PAC1 receptors, in a patient in need thereof, comprising administering to the patient an effective amount of an antigen binding protein described herein. In particular embodiments, the antigen binding protein is a monoclonal antibody or binding fragment thereof. The term "patient" includes human patients. PACAP biological activity has been implicated in various physiological processes, including cardiovascular function, metabolic and endocrine function, inflammation, stress response, and regulation of the autonomic nervous system, particularly the balance between the sympathetic and parasympathetic systems. See, e.g., Tanida et al., Regulatory Peptides, Vol. 161: 73-80, 2010; Moody et al., Curr. Opin. Endocrinol. Diabetes Obes., Vol. 18: 61-67, 2011; and Hashimoto et al., Current Pharmaceutical Design, Vol. 17: 985-989, 2011.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a particular condition (e.g. chronic pain, headache or migraine). In some embodiments, the effective amount is a therapeutically effective amount or a prophylactically effective amount. A "therapeutically effective amount" is an amount sufficient to remedy a disease state (e.g., a headache, migraine, or chronic pain) or symptom(s), particularly a state or symptom(s) associated with the disease state, or otherwise prevent, hinder, retard or reverse the progression of the disease state or any other undesirable symptom associated with the disease in any way whatsoever (i.e. that provides "therapeutic efficacy"). A "prophylactically effective amount" is an amount of a pharmaceutical composition that, when administered to a subject, will have the intended prophylactic effect, e.g., preventing or delaying the onset (or reoccurrence) of the condition (e.g. headache or migraine), or reducing the likelihood of the onset (or reoccurrence) of the condition (e.g. headache, migraine, or headache symptoms). The full therapeutic or prophylactic effect does not necessarily occur by administration of one dose, and may occur only after administration of a series of doses. Thus, a therapeutically or prophylactically effective amount may be administered in one or more administrations.

In certain embodiments, the present invention provides a method for inhibiting activation of the PAC1 receptor in a patient having a headache condition comprising administering to the patient an effective amount of an antigen binding protein, such as a monoclonal antibody or binding fragment thereof, described herein. In some embodiments, the method may treat or prevent symptoms of the headache condition in the patient. Accordingly, the present invention also includes a method for treating or preventing a headache condition, particularly migraine headache, in a patient in need thereof comprising administering to the patient an effective amount of an antigen binding protein (e.g. monoclonal antibody or binding fragment thereof) described herein. In certain embodiments, the antigen binding protein administered to the patient specifically binds to the C-terminal domain of PACAP38, for example within amino acids 28 to 38 of SEQ ID NO: 1. In one embodiment, the antigen binding proteins bind to an epitope within residues 28 to 37 of PACAP38 (SEQ ID NO: 1). In another embodiment, the antigen binding proteins bind to an epitope within residues 34 to 38 of PACAP38 (SEQ ID NO: 1). As described in Example 2 herein, it has been found that monoclonal antibodies that bind to this C-terminal region of PACAP38 are surprisingly potent inhibitors of PACAP38-induced PAC1 receptor activation (e.g. with IC50 values less than 500 pM as measured by a cell-based cAMP assay), and as such would be useful therapeutics for treating or preventing migraine headache, in particular, as explained in further detail below. In some embodiments, the antigen binding protein administered to the patient specifically binds to a polypeptide consisting of the sequence of SEQ ID NO: 4, but does not significantly bind to a polypeptide consisting of the sequence of SEQ ID NO: 5. In other embodiments, the antigen binding protein administered to the patient specifically binds to a polypeptide consisting of the sequence of SEQ ID NO: 4 and/or a polypeptide consisting of the sequence of SEQ ID NO: 126. In certain embodiments, the antigen binding protein administered to the patient binds to a polypeptide consisting of the sequence of SEQ ID NO: 4 with a binding affinity at least 2-fold greater than that for a polypeptide consisting of the sequence of SEQ ID NO: 115 as measured by a surface plasmon resonance assay. In other embodiments, the antigen binding protein administered to the patient binds to a polypeptide consisting of the sequence of SEQ ID NO: 4 with a binding affinity at least 5-fold greater than that for a polypeptide consisting of the sequence of SEQ ID NO: 115 as measured by a surface plasmon resonance assay. In still other embodiments, the antigen binding protein administered to the patient binds to a polypeptide consisting of the sequence of SEQ ID NO: 4 with a binding affinity at least 10-fold greater than that for a polypeptide consisting of the sequence of SEQ ID NO: 115 as measured by a surface plasmon resonance assay.

In some embodiments of the methods of the invention, the headache condition to be treated, prevented or ameliorated is migraine. Migraine headaches are recurrent headaches lasting about 4 to about 72 hours that are characterized by unilateral, pulsating, and/or moderate to severe pain and/or pain that is exacerbated by physical activity. Migraine headaches are often accompanied by nausea, vomiting, and/or sensitivity to light (photophobia), sound (phonophobia), or smell. In some patients, an aura precedes the onset of the migraine headache. The aura is typically a visual, sensory, language, or motor disturbance that signals the headache will soon occur. The methods described herein prevent, treat, or ameliorate one or more symptoms of migraine headaches with and without aura in human patients.

PACAP38, through activation of its receptors, induces vasodilation, particularly vasodilation of the dura vasculature (Schytz et al., Neurotherapeutics, Vol. 7(2):191-196, 2010). The PACAP38/PAC1 receptor signaling cascade, in particular, has been implicated in migraine pathophysiology (Amin et al., Brain, Vol. 137: 779-794, 2014). Infusion of PACAP38, which has a higher affinity for the PAC1 receptor than the VPAC1 and VPAC2 receptors, causes migraine-like headache in migraine patients (Schytz et al., Brain 132:16-25, 2009; Amin et al., Brain, Vol. 137: 779-794, 2014). In addition, PACAP38 levels are elevated in cranial circulation in patients experiencing a migraine attack, and the PACAP38 levels are reduced following treatment of the migraine symptoms with triptans (Tuka et al., Cephalalgia, Vol. 33, 1085-1095, 2013; Zagami et al., Ann. Clin. Transl. Neurol., Vol. 1: 1036-1040, 2014). These reports suggest that endogenous release of PACAP38 is an important trigger of migraine headache and its effects are primarily mediated through activation of the PAC1 receptor.

In some embodiments, the patients to be treated according to the methods of the invention have, suffer from, or are diagnosed with episodic migraine. Episodic migraine is diagnosed when patients with a history of migraine (e.g. at least five lifetime attacks of migraine headache) have 14 or fewer migraine headache days per month. A "migraine headache day" includes any calendar day during which a patient experiences the onset, continuation, or recurrence of a "migraine headache" with or without aura lasting greater than 30 minutes. A "migraine headache" is a headache associated with nausea or vomiting or sensitivity to light or sound and/or a headache characterized by at least two of the following pain features: unilateral pain, throbbing pain, moderate to severe pain intensity, or pain exacerbated by physical activity. In certain embodiments, patients having, suffering from, or diagnosed with episodic migraine have at least four, but less than 15 migraine headache days per month on average. In related embodiments, patients having, suffering from, or diagnosed with episodic migraine have fewer than 15 headache days per month on average. As used herein, a "headache day" is any calendar day in which the patient experiences a migraine headache as defined herein or any headache that lasts greater than 30 minutes or requires acute headache treatment.

In certain embodiments, the patients to be treated according to the methods of the invention have, suffer from, or are diagnosed with chronic migraine. Chronic migraine is diagnosed when migraine patients (i.e. patients with at least five lifetime attacks of migraine headache) have 15 or more headache days per month and at least 8 of the headache days are migraine headache days. In some embodiments, patients having, suffering from, or diagnosed with chronic migraine have 15 or more migraine headache days per month on average. In certain embodiments of the methods described herein, administration of an antigen binding protein of the invention prevents, reduces, or delays the progression of episodic migraine to chronic migraine in the patient.

In other embodiments, the present invention provides a method for treating or ameliorating cluster headache in a patient in need thereof comprising administering to the patient an effective amount of an antigen binding protein (e.g. monoclonal antibody or binding fragment thereof) described herein. Cluster headache is a condition that involves, as its most prominent feature, recurrent, severe headaches on one side of the head, typically around the eye (see Nesbitt el al., BMJ, Vol. 344:e2407, 2012). Some doctors and scientists have described the pain resulting from cluster headaches as the most intense pain a human can endure—worse than giving birth, burns or broken bones. Cluster headaches often occur periodically: spontaneous remissions interrupt active periods of pain. Cluster headaches are often accompanied by cranial autonomic symptoms, such as tearing, nasal congestion, ptosis, pupil constriction, facial blushing, sweating, and swelling around the eye, often confined to the side of the head with the pain. The average age of onset of cluster headache is ~30-50 years. It is more prevalent in males with a male to female ratio of about 2.5:1 to about 3.5:1. Sphenopalatine ganglion (SPG) stimulation has been used for the treatment of cluster headache. A neurostimulation system, which delivers low-level (but high frequency, physiologic-blocking) electrical stimulation to the SPG, has demonstrated efficacy in relieving the acute debilitating pain of cluster headache in a recent clinical trial (see Schoenen J, el al., Cephalalgia, Vol. 33(10):816-30, 2013). In view of this evidence and because PACAP is one of the major neurotransmitters in SPG, inhibition of PACAP signaling with an antigen binding protein described herein is expected to have efficacy in treating cluster headache in humans.

Other conditions associated with PACAP biological activity that may be treated according to the methods of the invention include, but are not limited to, inflammatory skin conditions, such as rosacea (see U.S. Patent Publication No. 20110229423), chronic pain syndromes, such as neuropathic pain (see Jongsma et al., Neuroreport, Vol. 12: 2215-2219, 2001; Hashimoto et al., Annals of the New York Academy of Sciences, Vol. 1070: 75-89, 2006), tension-type headaches, hemiplegic migraine, retinal migraine, anxiety disorders, such as posttraumatic stress disorder (see Hammack and May, Biol. Psychiatry, Vol. 78(3):167-177, 2015), irritable bowel syndrome, and vasomotor symptoms (e.g. hot flashes, facial flushing, sweating, and night sweats), such as those associated with menopause. In one embodiment, the condition is chronic pain. In another embodiment, the condition is neuropathic pain. In any of the methods described herein, the treatment can comprise prophylactic treatment. Prophylactic treatment refers to treatment designed to be taken before the onset of a condition or an attack (e.g. before a migraine attack or onset of a cluster headache episode) to reduce the frequency, severity, and/or length of the symptoms (e.g. migraine or cluster headaches) in the patient.

The antigen binding proteins of the invention are useful for detecting PACAP (i.e. PACAP38 and PACAP27) in biological samples and identification of cells or tissues that express the PACAP peptide. For instance, the antigen binding proteins can be used in diagnostic assays, e.g., immunoassays to detect and/or quantify PACAP peptide expressed in a tissue or cell or presence in a bodily fluid, such as cerebrospinal fluid, blood, serum, or plasma. In some embodiments, the antigen binding proteins can be used to differentially detect and/or quantitate PACAP38 from PACAP27. For instance, N-terminal or central domain binding antibodies described herein (e.g. mAb4, mAb5, and mAb6) can bind to both PACAP38 and PACAP27, whereas C-terminal antibodies described herein (e.g. mAb1, mAb2, and mAb3) can only bind to PACAP38. Thus, N-terminal/central domain antigen binding proteins and C-terminal antigen binding proteins can be employed in immunoassays to detect PACAP38, PACAP27, or both in various tissues and bodily fluids. In addition, the antigen binding proteins described herein can be used to inhibit VPAC1, VPAC2, and/or PAC1 receptor from forming a complex with PACAP, thereby modulating the biological activity of these receptors in a cell or tissue. Such biological activities include vasodilation.

The antigen binding proteins described herein can be used for diagnostic purposes to detect, diagnose, or monitor diseases and/or conditions associated with PACAP38, including migraine, cluster headache, and anxiety disorders, such as posttraumatic stress disorder. Elevated levels of PACAP38 in blood have been associated with these conditions. See, e.g., Ressler et al., Nature, Vol. 470: 492-497, 2011; Tuka et al., Cephalalgia, Vol. 33, 1085-1095, 2013; Zagami et al., Ann. Clin. Transl. Neurol., Vol. 1: 1036-1040, 2014. Also provided are methods for the detection of the presence of PACAP in a sample using classical immunohistological methods known to those of skill in the art (e.g., Tijssen, 1993, Practice and Theory of Enzyme Immunoassays, Vol 15 (Eds R. H. Burdon and P. H. van Knippenberg, Elsevier, Amsterdam); Zola, 1987, Monoclonal Antibodies: A Manual of Techniques, pp. 147-158 (CRC Press, Inc.); Jalkanen et al., 1985, J. Cell. Biol. 101:976-985; Jalkanen et al., 1987, J. Cell Biol. 105:3087-3096). Examples of methods useful in the detection of the presence of PACAP include immunoassays, such as the enzyme linked immunosorbent assay (ELISA) and the radioimmunoassay (RIA), using the antigen binding proteins described herein. The detection of PACAP can be performed in vivo or in vitro.

For diagnostic applications, the antigen binding protein can be labeled with a detectable labeling group. Suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used.

In another embodiment, the antigen binding proteins described herein can be used to identify a cell or cells that express PACAP38 and/or PACAP27. In a specific embodiment, the antigen binding protein is labeled with a labeling group and the binding of the labeled antigen binding protein to PACAP38 and/or PACAP27 is detected. The antigen binding proteins, particularly the binding proteins that specifically bind to the C-terminus of PACAP38, can also be used in immunoprecipitation assays to separate PACAP38 from PACAP27 in biological samples. In a further specific embodiment, the binding of the antigen binding protein to PACAP is detected in vivo. In a further specific embodiment, the antigen binding protein is isolated and measured using techniques known in the art. See, for example, Harlow and Lane, 1988, Antibodies: A Laboratory Manual, New York: Cold Spring Harbor (ed. 1991 and periodic supplements); John E. Coligan, ed., 1993, Current Protocols In Immunology New York: John Wiley & Sons.

The following examples, including the experiments conducted and the results achieved, are provided for illustrative purposes only and are not to be construed as limiting the scope of the appended claims.

EXAMPLES

Example 1. Generation of Anti-PACAP Antibodies

Rabbits were immunized with human PACAP38 peptide (HSDGIFTDSYSRYRKQMAVKKYLAAVLGKRYKQRVKNK; SEQ ID NO: 1). Monoclonal antibodies were generated from the immunized rabbits using the Selected Lymphocyte Antibody Method (SLAM) as described in Babcook el al., Proc. Natl. Acad. Sci. USA, Vol. 93: 7843-7848, 1996. Briefly, B cells were harvested from spleens from the immunized rabbits and expanded in culture. The supernatant from the expanded B-cell cultures was initially screened for binding to an amino terminal PACAP38 peptide (HSDGIFTDSYSRY; SEQ ID NO: 5) and a carboxy terminal PACAP38 peptide (GKRYKQRVKNK; SEQ ID NO: 4) using an ELISA assay. From the initial screen, 2,935 N-terminal and/or C-terminal binders were identified. The affinity of these antibodies for full-length human PACAP38 (SEQ ID NO: 1) was assessed by ELISA assay. The top 53 antibodies with the highest affinity to full-length human PACAP38 and that bound only the N-terminal peptide or the C-terminal peptide were screened for binding to vasoactive intestinal peptide (VIP; HSDAVFTDNYTRLRKQMAVKKYLNSILN; SEQ ID NO: 3) at 10-fold higher concentrations than that used for the full-length PACAP38 peptide to identify antibodies that did not cross-react with VIP. Data for the top 13 hits from the VIP counter-screen are shown in Table 8 below. Generally, these antibodies had high affinity to full-length PACAP38 and bound to either the N-terminal PACAP peptide (SEQ ID NO: 5) or C-terminal PACAP peptide (SEQ ID NO: 4), but did not significantly bind to VIP.

TABLE 8

ELISA Assay Screening Data for Anti-PACAP Antibodies[1]

| Antibody Designation | C-terminal Peptide 500 ng/mL | N-terminal Peptide 500 ng/mL | Full-length PACAP38 10 ng/mL | VIP 100 ng/mL |
|---|---|---|---|---|
| 1 (c20) | 5.33 | 0.05 | 4.09 | 0.08 |
| 2 (c81) | 3.74 | 0.06 | 3.39 | 0.09 |
| 3 (c89) | 3.59 | 0.06 | 3.17 | 0.07 |
| 7 (c8) | 0.59 | 0.07 | 3.93 | 0.08 |
| 8 (c15) | 0.41 | 0.07 | 3.38 | 0.07 |
| 9 (c64) | 0.69 | 0.07 | 3.61 | 0.07 |
| 4 (c47) | 0.05 | 3.68 | 2.09 | 0.24 |
| 5 (c71) | 0.05 | 1.34 | 3.21 | 0.12 |
| 6 (c55) | 0.05 | 4.24 | 3.55 | 0.95 |
| 10 | 0.05 | 1.02 | 2.06 | 0.06 |
| 11 | 0.06 | 1.72 | 1.70 | 0.13 |
| 12 (c26) | 0.08 | 0.38 | 6.00 | 0.20 |
| 13 | 0.07 | 0.31 | 4.19 | 1.62 |

[1]Optical Density values are provided; higher values indicate a higher level of binding The top 13 hits from the supernatant screens were evaluated in the hemolytic plaque assay to identify and isolate single antibody forming cells (AFCs) as described in Babcook et al., Proc. Natl. Acad. Sci. USA, Vol. 93: 7843-7848, 1996. The central AFC in each plaque was isolated, and mRNA was subsequently isolated from the single cell. The antibody sequences were amplified from the single cell mRNA using reverse-transcriptase PCR. Six of the monoclonal antibodies (3 C-terminal binders and 3 N-terminal binders) were cloned, recombinantly expressed, and purified. The amino acid sequences for each of the six antibodies (mAb1, mAb2, mAb3, mAb4, mAb5, and mAb6) are shown in Tables 1 (CDRs), 2 (variable regions), and 5 (full heavy and light chains).

Example 2. Neutralizing Activity of Anti-PACAP Monoclonal Antibodies

The recombinantly-produced, purified monoclonal antibodies (mAbs) were evaluated for binding to full-length human PACAP38 (SEQ ID NO: 1) and its isoform PACAP27 (HSDGIFTDSYSRYRKQMAVKKYLAAVL; SEQ ID NO: 2) using an ELISA assay. The ELISA assay used unlabeled mAbs 1 to 6 as capture reagents at the concentration of 13 nM. Analyte PACAP38 (SEQ ID NO: 1) and its isoform PACAP27 (SEQ ID NO: 2) were evaluated at two concentration levels (6.6 and 657 pM for PACAP38; 9.5 and 956 pM for PACAP27). Biotinylated mAbs 1 to 6 at the concentration of 5 nM were the secondary assay reagents. Neutravidin Horseradish Peroxidase (HRP) reacted with the biotinylated mAbs and produced colorimetric signals, optical density, in the presence of 3,3',5,5'-Tetramethylbenzidine (TMB) substrate solution. The intensity of optical density corresponded to the analyte concentration. The results of this assay revealed that mAb1, mAb2, and mAb3 bound to PACAP38, but not PACAP27. MAb4, mAbs, and mAb6 bound to both PACAP38 and PACAP27. The results suggest that mAbs 1, 2, and 3 bind to PACAP38 at an epitope within amino acids 28 to 38 of PACAP38, and the data are consistent with the data in Table 8 in Example 1 showing that these three mAbs bind to a C-terminal PACAP peptide, but not an N-terminal peptide.

Next, the functional activity of the six mAbs was assessed using a cell-based PAC1 receptor activity assay. Both PACAP38 and PACAP27 are agonists of the PAC1 receptor, activation of which results in an increase in intracellular cAMP. The assay employed a human neuroblastoma-derived cell line (SH-SY5Y; Biedler J L, et al., Cancer Res. 38: 3751-3757, 1978) obtained from ATCC (ATCC Number CRL-2266; "CRL-2266 cells"). CRL-2266 cells express human PAC1 receptor (Monaghan et al., J Neurochem. 104(1): 74-88, 2008). The LANCE Ultra cAMP assay kit (PerkinElmer, Boston, Mass.) was used to measure cAMP concentration.

On the day of the assay, the frozen CRL-2266 cells were thawed at 37° C. and were washed once with assay buffer. 10 µL of cell suspension containing 2,000 cells was added into 96 half-area white plates. After adding 5 µL of the anti-PACAP monoclonal antibody (10 point dose response curve: concentration range from 1 µM to 0.5 fM), the mixture was incubated for 30 min at room temperature. Then, 5 µL of either human PACAP38 (10 pM final concentration) or human PACAP27 (10 pM final concentration) was added and the mixture was further incubated for 15 min at room temperature. After human PACAP38 or PACAP27 stimulation, 20 µL of detection mix was added and incubated for 45 minutes at room temperature. The plates were read on EnVision instrument (PerkinElmer, Boston, Mass.) at emission wavelength 665 nm. Data were processed and analyzed by Prizm (GraphPad Software Inc.).

Figure 2A:
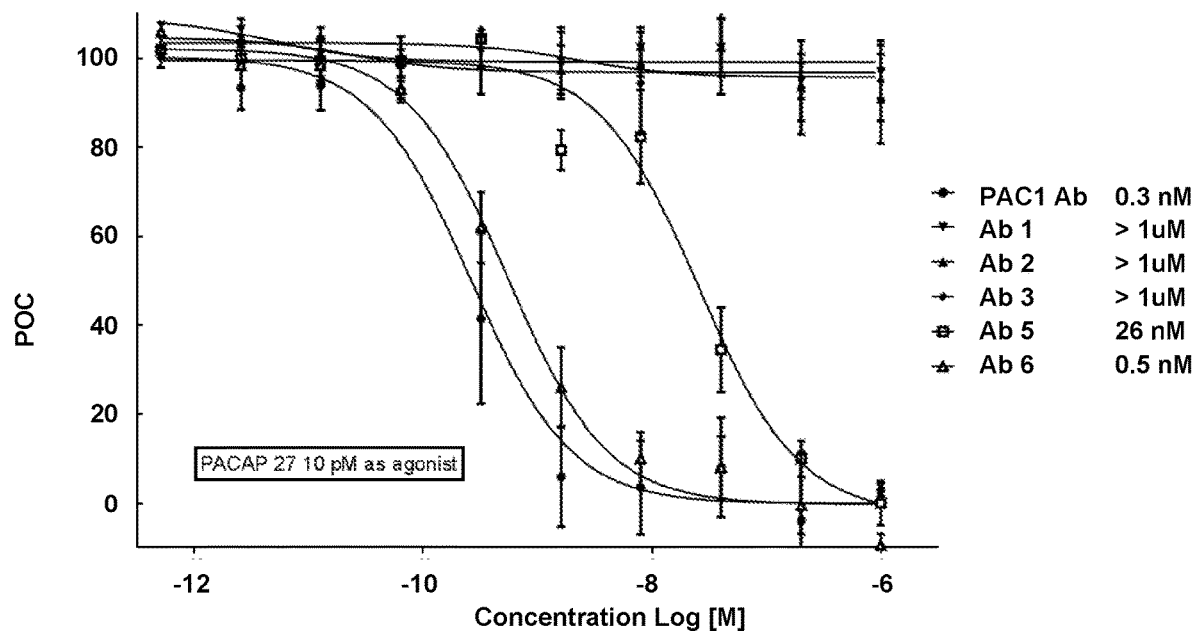
FIGS. 2A and 2B depict dose-response curves for monoclonal anti-PACAP antibodies (Ab1, Ab2, Ab3, Ab4, Ab5, and Ab6) and a monoclonal anti-PAC1 receptor antibody (PAC1 Ab) for inhibition of PACAP27-induced activation of the human PAC1 receptor. The IC50 values for each of the antibodies are listed to the right of the antibody designation in the legend.
Figure 2B:
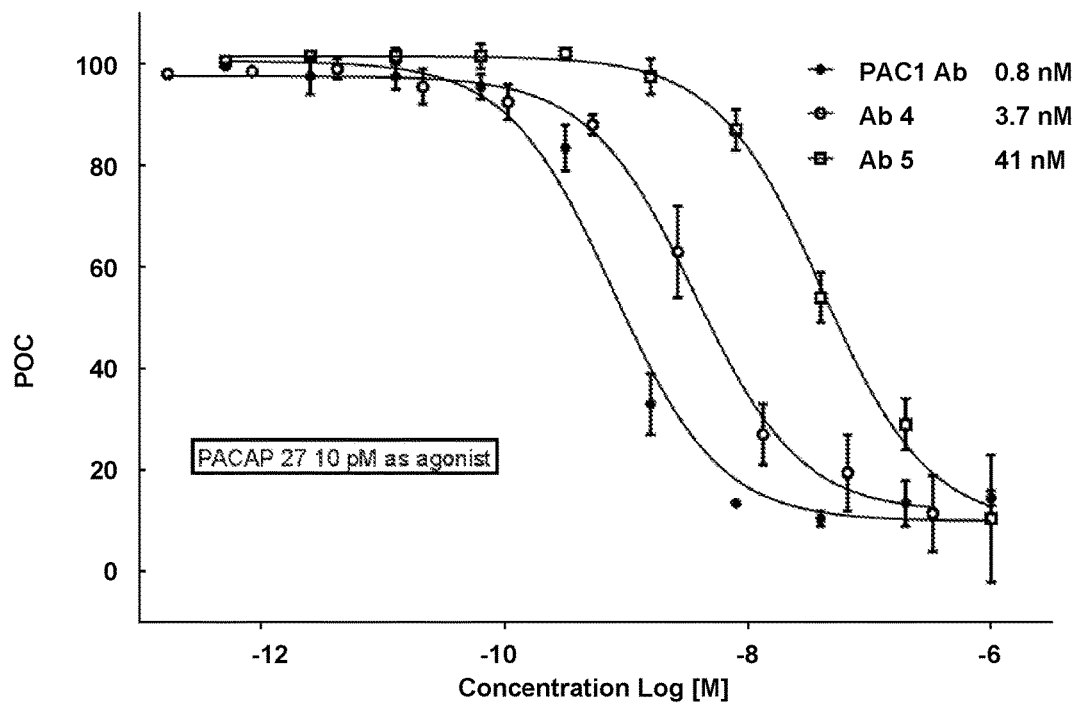

FIG. 1 depicts the dose-response curve for each of the six mAbs for inhibiting PACAP38-induced activation of the PAC1 receptor. The IC50 values for each of the antibodies are shown to the right of the antibody designations in the legend. MAb1, mAb2, and mAb3, all of which bind to the C-terminus of PACAP38, potently inhibited PAC1 receptor activation by PACAP38 with IC50 values in the subnanomolar range. The C-terminal binders were more potent than the N-terminal binders (mAbs 4, 5, and 6). MAbs 1, 2, and 3 were about 10-fold more potent than a human antibody against the human PAC1 receptor (PAC1 Ab). Consistent with the data from the PACAP peptide binding experiments, mAbs 1, 2, and 3 did not inhibit PACAP27-induced activation of the PAC1 receptor. See FIGS. 2A and 2B. Thus, antibodies that bind within amino acids 28 to 38 of PACAP38 exhibit ligand-specific inhibition of PAC1 receptor activity, whereas antibodies that bind to the N-terminus of PACAP38 inhibit PAC1 receptor activation induced by both ligands.

Previous structure-function studies report that the N-terminus of the PACAP peptide is critical for activation of the PAC1 receptor. For example, truncations of the peptide at the N-terminus result in loss of potency in PAC1 receptor-mediated adenylate cyclase activity and peptides lacking the first five N-terminal amino acids are converted into competitive antagonists (Robberecht et al., Mol. Pharmacol., Vol. 42: 347-355, 1992). The conformation of the N-terminal domain comprised of the first seven amino acids of the PACAP peptide is essential for PAC1 receptor binding and subsequent activation of the receptor (Bourgault el al., J. Med. Chem., Vol. 52: 3308-3316, 2009).

In contrast, truncations at the C-terminus of PACAP38 do not significantly affect the ability of the peptide to activate the PAC1 receptor although the binding affinity of the peptide is reduced. PACAP27, PACAP(1-23), and PACAP (1-21) all act as full PAC1 receptor agonists despite lacking the C-terminal 11, 15, and 17 amino acids, respectively (Inooka et al., Nature Structural Biology, Vol. 8: 161-165, 2001; Bourgault at al., J. Mol. Neurosci., Vol. 36: 260-269, 2008). Consistent with the apparent lack of importance of the C-terminal amino acids in receptor activation, an antibody that bound to a peptide consisting of amino acids 31-38 of PACAP38 had no inhibitory effect on PACAP38-induced cAMP production in rat PC12 cells (i.e. the antibody had no neutralization activity). See U.S. Pat. No. 5,486,472. Given these reports in the field, it is surprising and unexpected that the three monoclonal antibodies that bind to PACAP38 within amino acids 28-38 (mAbs 1, 2, and 3) were more potent in inhibiting PACAP38-induced PAC1 receptor activation than the antibodies that bind to the N-terminus of PACAP38.

Example 3. Epitope Mapping of Anti-PACAP Antibodies

The binding epitopes of anti-PACAP antibodies were evaluated by using the Biacore 3000 biosensor-based instrument (GE Healthcare USA). The Biacore 3000 instrument utilizes surface plasmon resonance (SPR) technology to measure mass increase on the sensor-chip surface. The binding interactions are measured in real-time and recorded as Response Units (RU). Each binding profile (cycle) is stored in a "sensorgram" in real-time. Generally, Biacore technology entails immobilizing a ligand of interest on to a flow-cell of the sensor-chip via a coupling chemistry. The analyte (e.g. putative binding partner to the ligand of interest) is injected across the immobilized ligand allowing it to bind to the ligand-immobilized surface. The magnitude of the response is directly proportional to the mass increase on the immobilized surface due to the binding of the analyte.

In this experiment, various peptide fragments of PACAP38 were incubated with each of the six antibodies (mAb1, mAb2, mAb3, mAb4, mAb5, and mAb6) described in Example 2 and evaluated for their ability to inhibit binding of the antibodies to full-length PACAP38 immobilized on the sensor-chip. The binding epitopes for each of the antibodies were deduced from the set of peptides that were able to inhibit the binding of each antibody to full-length PACAP38.

Full-length PACAP38 peptide (SEQ ID NO: 1) was diluted to 2 μM in acetate buffer and immobilized on to flow cell 2 or 4 of a CM5 sensor chip by amine coupling chemistry. The targeted immobilization density was estimated to be around 1000 RU. A blank, reference surface on flow cell 1 or 3 was also prepared using an amine coupling chemistry to calculate the net binding using the following equation:

Net binding=Active surface RU−Reference surface RU

Each of the six anti-PACAP antibodies was incubated at a 1:200 molar ratio (Ab:peptide fragment) with each of the peptide fragments in Table 9 at an ambient temperature for 2 hours prior to analysis. Full-length PACAP38 peptide (SEQ ID NO: 1) was also mixed in with each antibody separately as a control to demonstrate inhibition of antibody binding, thereby confirming the specificity of the antibody for PACAP38. A second control containing 6.5 nM antibody was prepared in sample diluent to be used as the untreated control sample for each antibody. Full-length PACAP38, buffer, and each peptide fragment were also tested to evaluate non-specific binding to the immobilized PACAP38 surface.

TABLE 9

PACAP38 Peptide Fragments used for Epitope Mapping

| Peptide No. | Amino Acid Positions within PACAP38 | Sequence | SEQ ID NO. |
|---|---|---|---|
| 1 | 1-27 | HSDGIFTDSYSRYRKQMAVKKYLAAVL | 2 |
| 2 | 26-33 | VLGKRYKQ | 112 |
| 3 | 6-37 | FTDSYSRYRKQMAVKKYLAAVLGKRYKQRVKN | 113 |
| 4 | 6-35 | FTDSYSRYRKQMAVKKYLAAVLGKRYKQRV | 114 |
| 5 | 31-38 | YKQRVKNK | 115 |
| 6 | 27-38 | LGKRYKQRVKNK | 116 |
| 7 | 14-38 | RKQMAVKKYLAAVLGKRYKQRVKNK | 117 |
| 8 | 11-27 | SRYRKQMAVKKYLAAVL | 118 |
| 9 | 4-27 | GIFTDSYSRYRKQMAVKKYLAAVL | 119 |
| 10 | 1-13 | HSDGIFTDSYSRY | 5 |
| 11 | 6-38 | FTDSYSRYRKQMAVKKYLAAVLGKRYKQRVKNK | 120 |
| 12 | 6-36 | FTDSYSRYRKQMAVKKYLAAVLGKRYKQRVK | 121 |
| 13 | 6-20 | FTDSYSRYRKQMAVK | 122 |
| 14 | 9-18 | SYSRYRKQMA | 123 |
| 15 | 16-23 | QMAVKKYL | 124 |
| 16 | 19-25 | VKKYLAA | 125 |
| 17 | 34-38 | RVKNK | 126 |
| 18 | 28-38 | GKRYKQRVKNK | 4 |
| 19 | 30-37 | RYKQRVKN | 127 |

Each sample was injected at 5 μl/min for 60 seconds and it travelled either through flow cell 1 (blank surface) into flow cell 2 (PACAP38 surface) or through flow cell 3 (blank surface) into flow cell 4 (PACAP38 surface). A baseline report was taken at 15 seconds prior to each sample injection. The sample binding report was taken at 45 seconds after completion of each injection. The chip surface was regenerated after each sample using a 100 mM HCl injection.

Untreated antibody samples for each of the six antibodies were tested before and after the testing of samples comprising the antibody/peptide mixtures (i.e. treated antibody samples) to assess the immobilized PACAP38 surface integrity for its binding capability over time. An average of the untreated antibody binding response was used to calculate percent inhibition by each peptide fragment using the following equation:

Percent inhibition={(Avg. untreated Ab RU−Treated Ab RU)/Avg. untreated Ab RU}×100

The anti-PACAP antibody was considered to be reactive to the peptide fragment if the percent inhibition was greater than 50%.

Figure 3A:
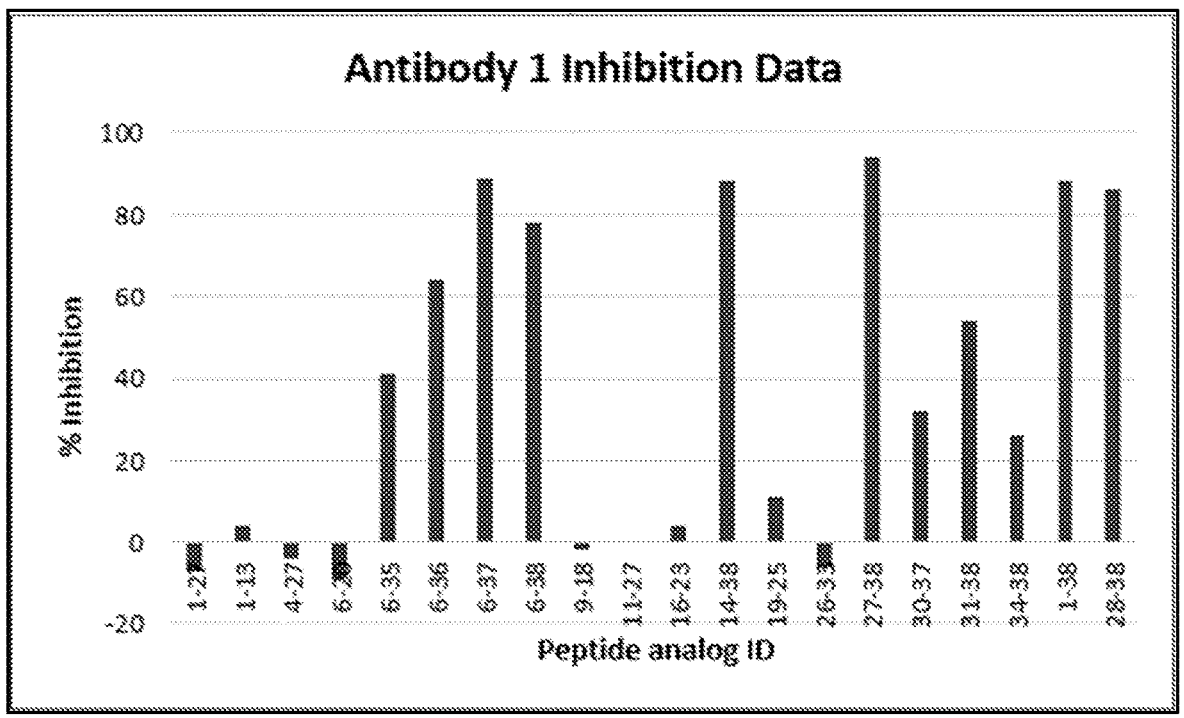
FIG. 3A is a bar graph showing the percent inhibition of monoclonal anti-PACAP antibody 1 (Ab1) binding to full-length PACAP38 by each of the peptide fragments consisting of the indicated amino acid residues of human PACAP38 (SEQ ID NO: 1).
Figure 3B:
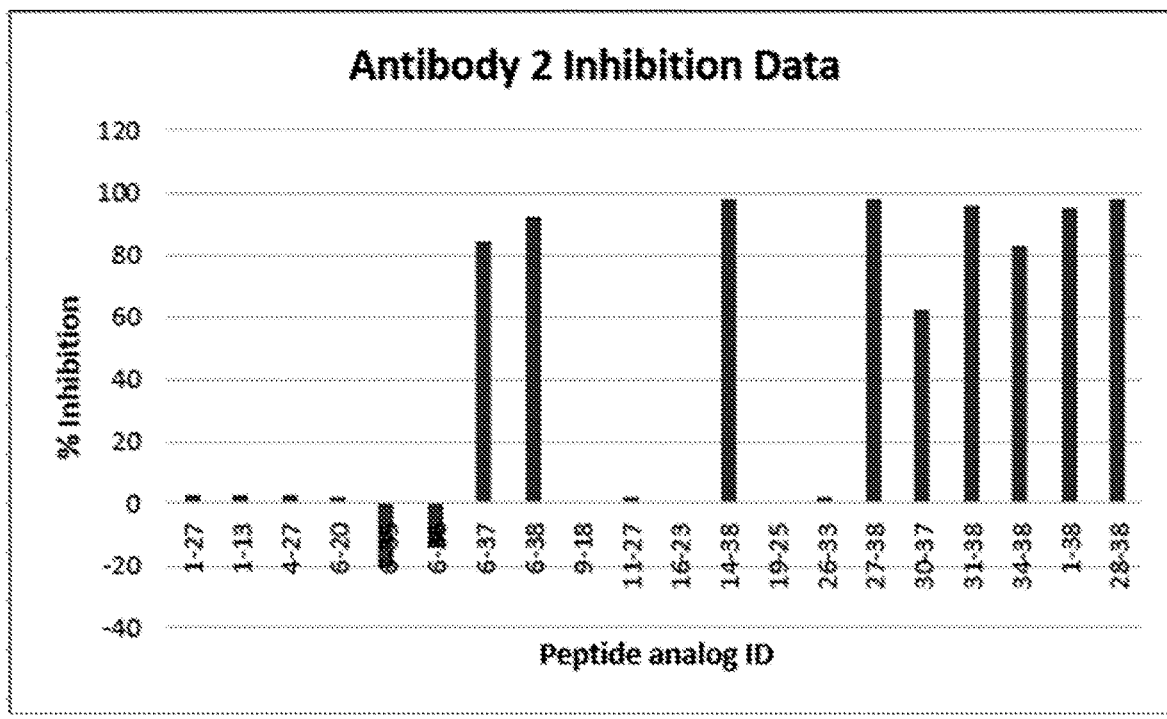
FIG. 3B is a bar graph showing the percent inhibition of monoclonal anti-PACAP antibody 2 (Ab2) binding to full-length PACAP38 by each of the peptide fragments consisting of the indicated amino acid residues of human PACAP38 (SEQ ID NO: 1).
Figure 3C:
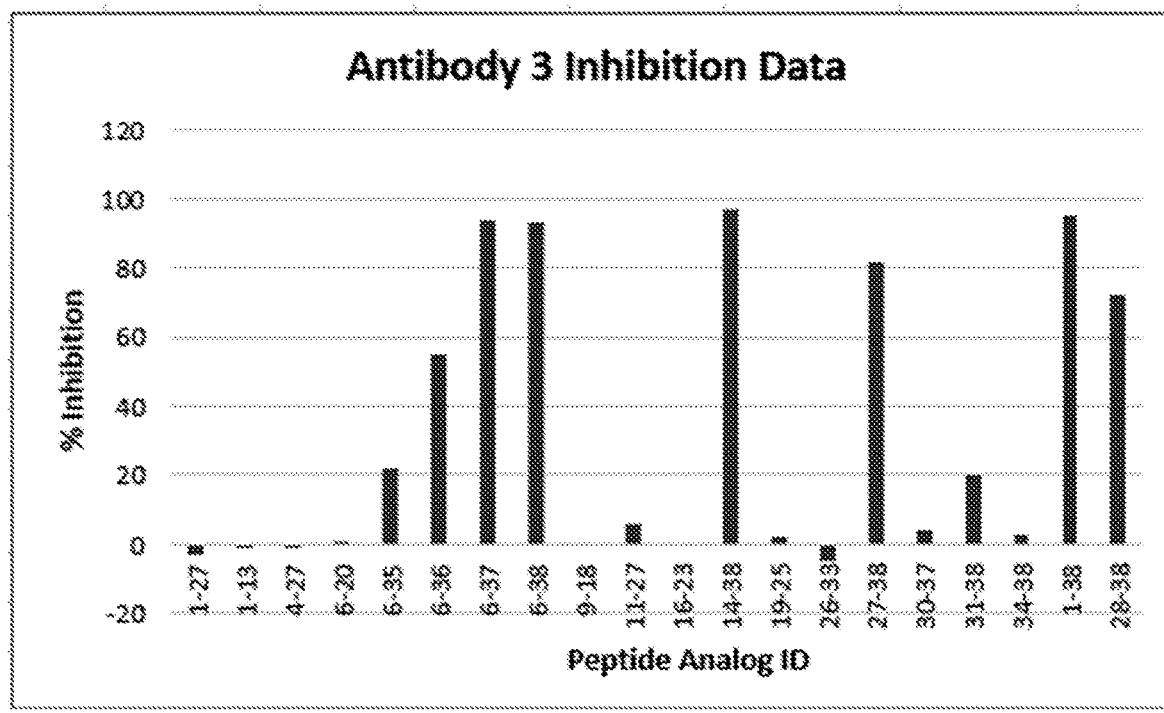
FIG. 3C is a bar graph showing the percent inhibition of monoclonal anti-PACAP antibody 3 (Ab3) binding to full-length PACAP38 by each of the peptide fragments consisting of the indicated amino acid residues of human PACAP38 (SEQ ID NO: 1).

The results of the analysis for each of the six antibodies are shown in FIGS. 3A-3F. Consistent with the results from the ELISA-based screening assay described in Example 1, mAb1, mAb2, and mAb3 bound to PACAP38 between amino acids 28 to 38. As shown in FIG. 3A, the binding of mAb1 to full-length PACAP38 was nearly completely inhibited by peptide fragments comprising amino acids 28-38 as well as a peptide consisting of amino acids 6-37, suggesting that the binding epitope for mAb1 is within amino acids 28 to 37 of PACAP38. The inhibition of mAb1 binding diminished with peptides containing C-terminal truncations (compare % inhibition for peptide fragments 6-35, 6-36, 6-37, and 6-38) and was completely eliminated by deletion of amino acids 34-38 (see % inhibition for peptide fragment consisting of amino acids 26-33), suggesting that the final four C-terminal amino acid residues are important for mAb1 binding to PACAP38. Similar results were obtained for mAb2, except that a peptide fragment consisting of amino acids 34 to 38 of PACAP38 was also able to nearly completely block binding of mAb2 to PACAP38, indicating that the binding epitope for this antibody can be narrowed down to amino acids 34 to 38 of PACAP38 (FIG. 3B). Binding of mAb3 to PACAP38 was substantially inhibited by peptide fragments comprising amino acids 28-38 as well as a peptide fragment comprising amino acids 6-37 (FIG. 3C). These results suggest that the binding epitope for mAb3 is located within amino acid residues 28 to 37 of PACAP38.

Figure 3D:
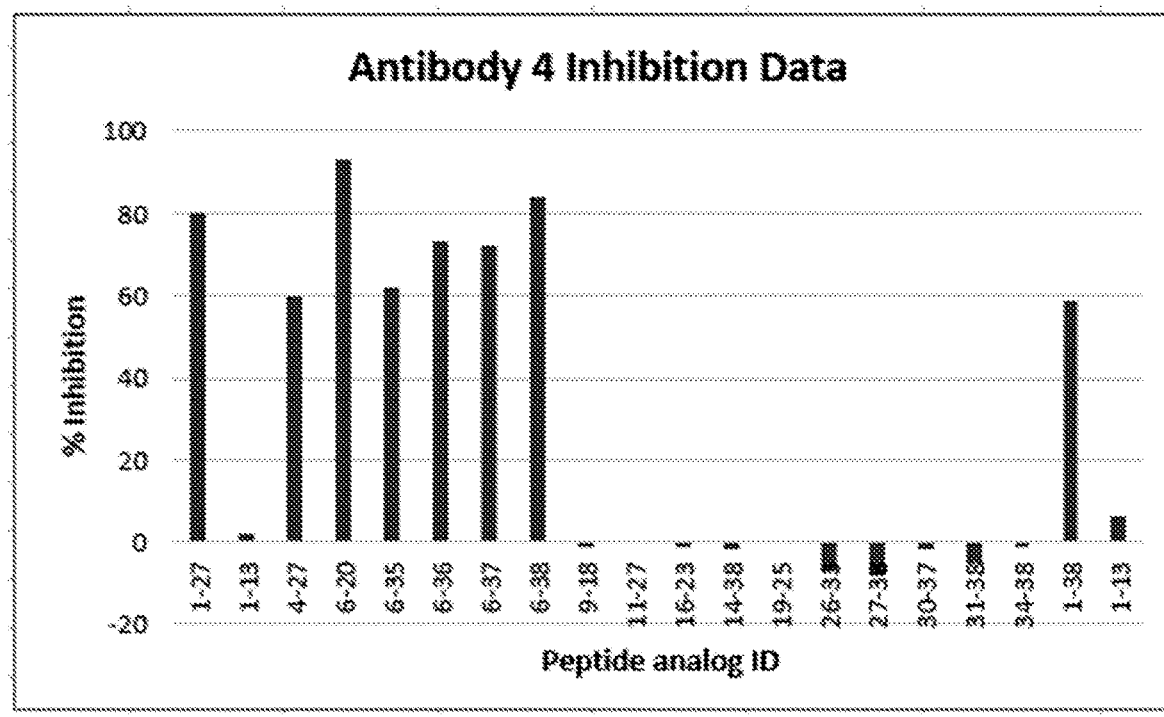
FIG. 3D is a bar graph showing the percent inhibition of monoclonal anti-PACAP antibody 4 (Ab4) binding to full-length PACAP38 by each of the peptide fragments consisting of the indicated amino acid residues of human PACAP38 (SEQ ID NO: 1).
Figure 3E:
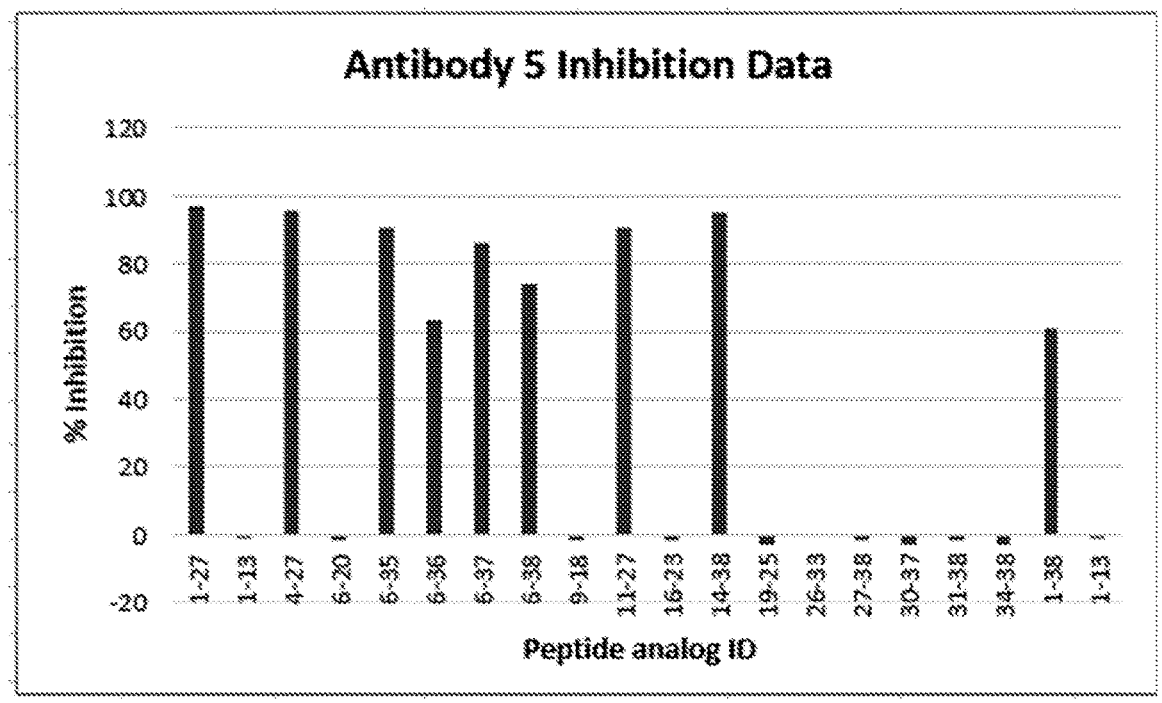
FIG. 3E is a bar graph showing the percent inhibition of monoclonal anti-PACAP antibody 5 (Ab5) binding to full-length PACAP38 by each of the peptide fragments consisting of the indicated amino acid residues of human PACAP38 (SEQ ID NO: 1).
Figure 3F:
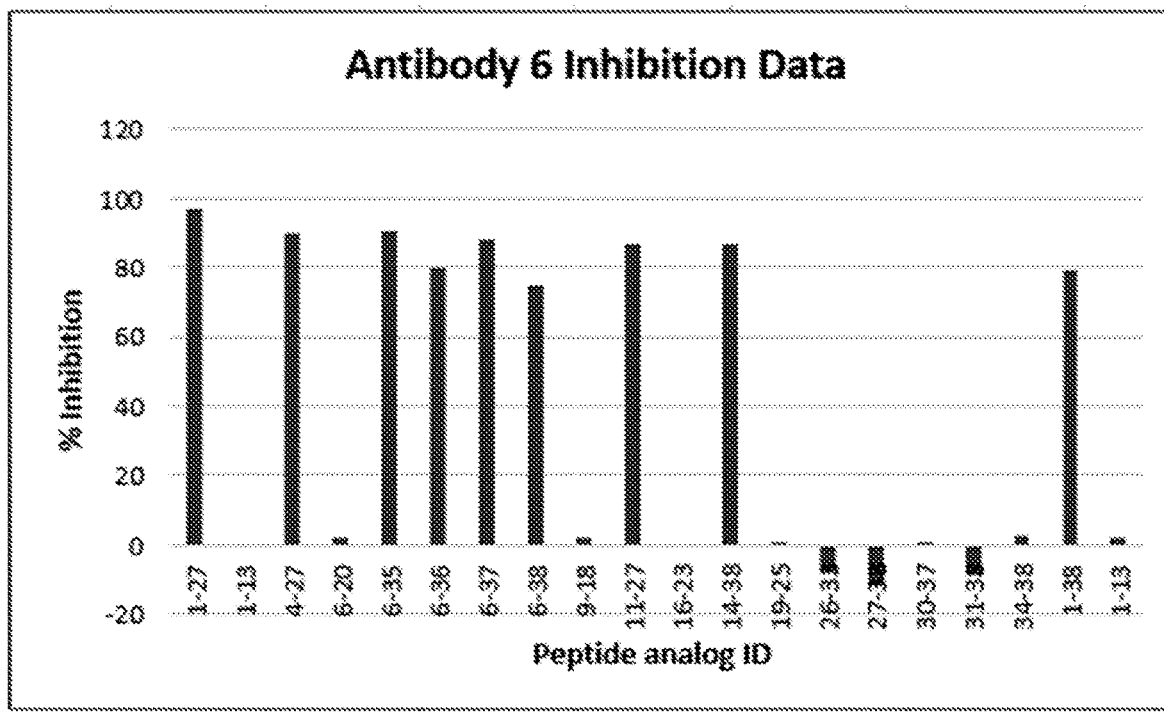
FIG. 3F is a bar graph showing the percent inhibition of monoclonal anti-PACAP antibody 6 (Ab6) binding to full-length PACAP38 by each of the peptide fragments consisting of the indicated amino acid residues of human PACAP38 (SEQ ID NO: 1).

The binding of mAb4 to PACAP38 was inhibited by PACAP27 and peptide fragments consisting of amino acids 4-27, amino acids 6-20, amino acids 6-35, amino acids 6-36, amino acids 6-37, and amino acids 6-38 (FIG. 3D). Mab4 binding was not inhibited by a peptide fragment consisting of amino acids 27-38. Based on these results, mAb4 most likely binds to PACAP38 within amino acid residues 6 to 20. The binding of mAb5 to PACAP38 was almost completely inhibited by PACAP27 and peptide fragments consisting of amino acids 4-27, amino acids 11-27, amino acids 6-35, and amino acids 14-38, but was not inhibited by peptide fragments consisting of amino acids 26-33 or amino acids 27-38 (FIG. 3E). Therefore, the binding epitope for mAb5 can be conservatively estimated to be between 14-27 amino acids of PACAP38. Similar results were obtained with mAb6 also suggesting that the binding epitope for mAb6 is between 14-27 amino acids of PACAP38 (FIG. 3F). In contrast to the results with the ELISA-based screening assay described in Example 1, mAb4, mAb5, and mAb6 did not bind to the N-terminal peptide consisting of amino acids 1-13 of PACAP38. The reason for this result is unclear. However, mAb4, mAb5, and mAb6 did not bind to the C-terminal peptide consisting of amino acids 28-38 and remained selective towards the N-terminal region of PACAP38.

Example 4. Inhibition of Vasodilation by Anti-PACAP Antibodies

PACAP38 is a vasodilatory peptide that when administered intradermally can cause an increase in local dermal blood flow in rodents, cynomolgus monkeys (cynos) and humans. This increase in local dermal blood flow (DBF) can be measured by laser Doppler imaging and the prevention of this effect by an anti-PACAP antibody can serve as a translational pharmacodynamic (PD) model of antagonism of PACAP biological activity.

To evaluate the efficacy of the anti-PACAP antibodies of the invention in inhibiting receptor activation in vivo, the ability of the antibodies to inhibit DBF induced by intradermal administration of PACAP38 in rats, cynos, and/or humans is tested. Specifically, animals are administered an anti-PACAP antibody (e.g. mAbs 1, 2, 3, 4, 5, or 6) or placebo subcutaneously or intravenously at one or more concentrations. Subsequently, PACAP38 peptide is injected intradermally into the abdomen (rats) or forearm or thigh (cynos or humans) and local DBF in the area of the injection site is measured by laser Doppler imaging prior to and periodically (e.g. every five or ten minutes) after injection. The detected intensity fluctuations are processed to give parameters of flux (proportional to tissue blood flow) and concentration (proportional to the concentration of moving blood cells). DBF is measured as Flux (relative units) or % change from baseline [100×(individual post-PACAP flux-individual baseline flux)/individual baseline flux]. An IC50 value for the anti-PACAP antibody can be calculated from a dose-response curve of antibody concentration vs. Flux. Ability of the anti-PACAP antibody to inhibit PACAP38-induced DBF can be used to predict the in vivo efficacy of the antibody to inhibit PACAP38-induced receptor activation and possible efficacy in treating PACAP/PAC1 receptor-mediated disorders, such as cluster headache and migraine.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. An isolated monoclonal antibody or binding fragment thereof that specifically binds to human pituitary adenylate cyclase-activating polypeptide (PACAP) and inhibits PACAP-induced activation of human PAC1 receptor comprising (i) a light chain variable region comprising complementarity determining regions CDRL1, CDRL2, and CDRL3, and (ii) a heavy chain variable region comprising complementarity determining regions CDRH1, CDRH2, and CDRH3, wherein:
   (a) CDRL1, CDRL2, and CDRL3 have the sequences of SEQ ID NOs: 32, 37, and 42, respectively, and CDRH1, CDRH2, and CDRH3 have the sequences of SEQ ID NOs: 48, 53, and 59, respectively;
   (b) CDRL1, CDRL2, and CDRL3 have the sequences of SEQ ID NOs: 33, 38, and 43, respectively, and CDRH1, CDRH2, and CDRH3 have the sequences of SEQ ID NOs: 49, 54, and 60, respectively; or
   (c) CDRL1, CDRL2, and CDRL3 have the sequences of SEQ ID NOs: 34, 39, and 44, respectively, and CDRH1, CDRH2, and CDRH3 have the sequences of SEQ ID NOs: 50, 55, and 61, respectively.

2. The isolated monoclonal antibody or binding fragment thereof of claim 1, wherein the monoclonal antibody or binding fragment comprises a light chain variable region comprising a sequence that is at least 90% identical to a sequence selected from SEQ ID NOs: 24, 26, or 28; and a heavy chain variable region comprising a sequence that is at least 90% identical to a sequence selected from SEQ ID NOs: 25, 27, or 29.

3. The isolated monoclonal antibody or binding fragment thereof of claim 1, wherein the monoclonal antibody or binding fragment comprises:
   (a) a light chain variable region comprising the sequence of SEQ ID NO: 24 and a heavy chain variable region comprising the sequence of SEQ ID NO: 25;
   (b) a light chain variable region comprising the sequence of SEQ ID NO: 26 and a heavy chain variable region comprising the sequence of SEQ ID NO: 27; or
   (c) a light chain variable region comprising the sequence of SEQ ID NO: 28 and a heavy chain variable region comprising the sequence of SEQ ID NO: 29.

4. The isolated monoclonal antibody or binding fragment thereof of claim 1, wherein the monoclonal antibody or binding fragment thereof is a humanized antibody or binding fragment thereof.

5. The isolated monoclonal antibody of claim 4, wherein the humanized monoclonal antibody comprises an Fc region from a human IgG1, IgG2, IgG3, or IgG4 antibody.

6. The isolated monoclonal antibody of claim 5, wherein the humanized monoclonal antibody comprises an Fc region from a human IgG1 antibody.

7. The isolated monoclonal antibody of claim 6, wherein the Fc region comprises a N297G mutation, wherein the amino acid position is according to EU numbering.

8. A composition comprising the monoclonal antibody or binding fragment thereof of claim 1 and a pharmaceutically acceptable diluent, excipient, or carrier.

9. An isolated polynucleotide encoding the monoclonal antibody or binding fragment thereof of claim 1.

10. An expression vector comprising the polynucleotide of claim 9.

11. A host cell comprising the expression vector of claim 10.

12. A method of producing an anti-PACAP monoclonal antibody or binding fragment thereof comprising culturing the host cell of claim 11 under conditions that allow expression of the antibody or binding fragment; and recovering the antibody or binding fragment from the culture medium or host cell.

13. A method for inhibiting activation of human PAC1 receptor in a patient having a headache condition comprising administering to the patient an effective amount of a monoclonal antibody or binding fragment thereof of claim 1.

14. A method for treating or reducing the occurrence of preventing a headache condition in a patient in need thereof comprising administering to the patient an effective amount of a monoclonal antibody or binding fragment thereof of claim 1.

15. The method of claim 14, wherein the headache condition is cluster headache.

16. The method of claim 14, wherein the monoclonal antibody or binding fragment thereof is administered to the patient as a prophylactic treatment.

17. The method of claim 14, wherein the headache condition is migraine.

18. The method of claim 17, wherein the migraine is episodic migraine.

19. The method of claim 17, wherein the migraine is chronic migraine.

\* \* \* \* \*

SEQUENCE LISTING

<160> NUMBER OF SEQ ID NOS: 127

<210> SEQ ID NO 1
<211> LENGTH: 38
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 27
<212> TYPE: PRT
<213> ORGANISM: Homo sapiens

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 3
<211> LENGTH: 28
<212> TYPE: PRT
<213> ORGANISM: Homo sapiens

<400> SEQUENCE: 3

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 11
<212> TYPE: PRT
<213> ORGANISM: Artificial Sequence
<220> FEATURE:
<223> OTHER INFORMATION: polypeptide

<400> SEQUENCE: 4

Gly Lys Arg Tyr Lys Gln Arg Val Lys Asn Lys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: polypeptide

<400> SEQUENCE: 5

His Ser Asp Gly Ile Phe Thr Asp Ser Tyr Ser Arg Tyr
1               5                   10

<210> SEQ ID NO 6
<211> LENGTH: 219
<212> TYPE: PRT
<213> ORGANISM: Artificial Sequence
<220> FEATURE:
<223> OTHER INFORMATION: polypeptide

<400> SEQUENCE: 6

Ala Asp Val Val Met Thr Gln Thr Pro Ser Pro Val Ser Ala Ala Val
1               5                   10                  15

Gly Gly Thr Val Thr Ile Asn Cys Arg Ala Ser Glu Asp Ile Glu Ser
            20                  25                  30

Phe Leu Ala Trp Tyr Gln Gln Lys Pro Gly Gln Pro Pro Lys Leu Leu
        35                  40                  45

Ile Ser Arg Thr Ser Thr Leu Glu Ser Gly Val Ser Ser Arg Phe Lys
    50                  55                  60

Gly Ser Gly Ser Gly Thr Glu Phe Ile Leu Thr Ile Ser Asp Leu Glu
65                  70                  75                  80

Cys Ala Asp Ala Ala Thr Tyr Tyr Cys Gln Cys Thr Asp Gly Ser Ser
                85                  90                  95

Ser Ser Ser Ser Tyr Gly Trp Asp Ala Phe Gly Gly Gly Thr Glu Val
                100                 105                 110

Val Val Lys Gly Asp Pro Val Ala Pro Thr Val Leu Leu Phe Pro Pro
            115                 120                 125

Ser Ser Asp Glu Val Ala Thr Gly Thr Val Thr Ile Val Cys Val Ala
        130                 135                 140

Asn Lys Tyr Phe Pro Asp Val Thr Val Thr Trp Glu Val Asp Gly Thr
145                 150                 155                 160

```
Thr Gln Thr Thr Gly Ile Glu Asn Ser Lys Thr Pro Gln Asn Ser Ala
                165                 170                 175

Asp Cys Thr Tyr Asn Leu Ser Ser Thr Leu Thr Leu Thr Ser Thr Gln
            180                 185                 190

Tyr Asn Ser His Lys Glu Tyr Thr Cys Lys Val Thr Gln Gly Thr Thr
        195                 200                 205

Ser Val Val Gln Ser Phe Ser Arg Lys Asn Cys
    210                 215
```

<210> SEQ ID NO 7
<211> LENGTH: 449
<212> TYPE: PRT
<213> ORGANISM: Artificial Sequence
<220> FEATURE:
<223> OTHER INFORMATION: polypeptide

<400> SEQUENCE: 7

```
Gln Ser Leu Glu Glu Ser Gly Gly Asp Leu Val Lys Pro Gly Ala Ser
1               5                   10                  15

Leu Thr Leu Thr Cys Lys Ala Ser Gly Ile Ala Phe Ser Asn Asp Tyr
            20                  25                  30

Met Cys Trp Val Arg Gln Ala Pro Gly Lys Gly Leu Glu Trp Ile Ala
        35                  40                  45

Cys Ile Phe Thr Gly Ser Ser Gly Ser Thr Tyr Tyr Ala Ser Trp Ala
    50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Arg Ala Ile Ser Val Leu Gly Tyr Phe Tyr Ala Ala Tyr Phe
            100                 105                 110

Phe Asp Phe Trp Gly Pro Gly Thr Leu Val Thr Val Ser Ser Gly Gln
        115                 120                 125

Pro Lys Ala Pro Ser Val Phe Pro Leu Ala Pro Cys Cys Gly Asp Thr
    130                 135                 140

Pro Ser Ser Thr Val Thr Leu Gly Cys Leu Val Lys Gly Tyr Leu Pro
145                 150                 155                 160

Glu Pro Val Thr Val Thr Trp Asn Ser Gly Thr Leu Thr Asn Gly Val
                165                 170                 175

Arg Thr Phe Pro Ser Val Arg Gln Ser Ser Gly Leu Tyr Ser Leu Ser
            180                 185                 190

Ser Val Val Ser Val Thr Ser Ser Gln Pro Val Thr Cys Asn Val
        195                 200                 205

Ala His Pro Ala Thr Asn Thr Lys Val Asp Lys Thr Val Ala Pro Ser
    210                 215                 220

Thr Cys Ser Lys Pro Thr Cys Pro Pro Glu Leu Leu Gly Gly Pro
225                 230                 235                 240

Ser Val Phe Ile Phe Pro Pro Lys Pro Lys Asp Thr Leu Met Ile Ser
                245                 250                 255

Arg Thr Pro Glu Val Thr Cys Val Val Val Asp Val Ser Gln Asp Asp
            260                 265                 270

Pro Glu Val Gln Phe Thr Trp Tyr Ile Asn Asn Glu Gln Val Arg Thr
        275                 280                 285

Ala Arg Pro Pro Leu Arg Glu Gln Gln Phe Asn Ser Thr Ile Arg Val
    290                 295                 300
```

Val Ser Thr Leu Pro Ile Ala His Gln Asp Trp Leu Arg Gly Lys Glu
305                 310                 315                 320

Phe Lys Cys Lys Val His Asn Lys Ala Leu Pro Ala Pro Ile Glu Lys
                325                 330                 335

Thr Ile Ser Lys Ala Arg Gly Gln Pro Leu Glu Pro Lys Val Tyr Thr
            340                 345                 350

Met Gly Pro Pro Arg Glu Glu Leu Ser Ser Arg Ser Val Ser Leu Thr
        355                 360                 365

Cys Met Ile Asn Gly Phe Tyr Pro Ser Asp Ile Ser Val Glu Trp Glu
370                 375                 380

Lys Asn Gly Lys Ala Glu Asp Asn Tyr Lys Thr Thr Pro Ala Val Leu
385                 390                 395                 400

Asp Ser Asp Gly Ser Tyr Phe Leu Tyr Ser Lys Leu Ser Val Pro Thr
                405                 410                 415

Ser Glu Trp Gln Arg Gly Asp Val Phe Thr Cys Ser Val Met His Glu
            420                 425                 430

Ala Leu His Asn His Tyr Thr Gln Lys Ser Ile Ser Arg Ser Pro Gly
        435                 440                 445

Lys

<210> SEQ ID NO 8
<211> LENGTH: 219
<212> TYPE: PRT
<213> ORGANISM: Artificial Sequence
<220> FEATURE:
<223> OTHER INFORMATION: polypeptide

<400> SEQUENCE: 8

Ala Asp Val Val Met Thr Gln Thr Pro Ser Pro Val Ser Ala Gln Val
1               5                   10                  15

Gly Gly Thr Val Thr Ile Asn Cys Gln Ala Ser Glu Ser Ile Asp Ser
            20                  25                  30

Asp Leu Ser Trp Tyr Gln Gln Lys Pro Gly Gln Pro Pro Lys Leu Leu
        35                  40                  45

Ile Tyr Arg Thr Phe Thr Leu Glu Ser Gly Val Pro Ser Arg Phe Lys
    50                  55                  60

Gly Ser Gly Ser Gly Thr Asp Tyr Thr Leu Thr Ile Ser Asp Leu Glu
65                  70                  75                  80

Cys Ala Asp Ala Ala Ile Tyr Tyr Cys Gln Cys Thr Asp Gly Ser Ser
                85                  90                  95

Ile Ser Gly Ser Tyr Gly Trp Asp Ala Phe Gly Gly Gly Thr Glu Val
            100                 105                 110

Val Val Lys Gly Asp Pro Val Ala Pro Thr Val Leu Leu Phe Pro Pro
        115                 120                 125

Ser Ser Asp Glu Val Ala Thr Gly Thr Val Thr Ile Val Cys Val Ala
130                 135                 140

Asn Lys Tyr Phe Pro Asp Val Thr Val Thr Trp Glu Val Asp Gly Thr
145                 150                 155                 160

Thr Gln Thr Thr Gly Ile Glu Asn Ser Lys Thr Pro Gln Asn Ser Ala
                165                 170                 175

Asp Cys Thr Tyr Asn Leu Ser Ser Thr Leu Thr Leu Thr Ser Thr Gln
            180                 185                 190

Tyr Asn Ser His Lys Glu Tyr Thr Cys Lys Val Thr Gln Gly Thr Thr
        195                 200                 205

```
Ser Val Val Gln Ser Phe Ser Arg Lys Asn Cys
    210                 215

<210> SEQ ID NO 9
<211> LENGTH: 449
<212> TYPE: PRT
<213> ORGANISM: Artificial Sequence
<220> FEATURE:
<223> OTHER INFORMATION: polypeptide

<400> SEQUENCE: 9

Gln Ser Leu Glu Glu Ser Gly Gly Leu Val Gln Pro Glu Gly Ser
1               5                   10                  15

Leu Thr Leu Thr Cys Thr Ala Ser Gly Phe Ser Phe Asn Ser Ser
            20                  25                  30

Tyr Met Cys Trp Val Arg Gln Ala Pro Gly Lys Gly Leu Glu Trp Ile
            35                  40                  45

Gly Cys Ile Phe Thr Gly Ser Ser Gly Asn Thr Tyr Tyr Ala Thr Trp
        50                  55                  60

Ala Gln Gly Arg Phe Thr Ile Ser Lys Thr Ser Thr Thr Val Thr Leu
65                  70                  75                  80

Glu Met Thr Ser Leu Thr Ala Ala Asp Thr Ala Thr Tyr Phe Cys Ala
                85                  90                  95

Arg Asp Arg Ala Tyr Phe Leu Val Gly Tyr Phe Tyr Ala Thr Tyr Tyr
            100                 105                 110

Phe Asp Leu Trp Gly Pro Gly Thr Leu Val Thr Val Ser Ser Gly Gln
        115                 120                 125

Pro Lys Ala Pro Ser Val Phe Pro Leu Ala Pro Cys Cys Gly Asp Thr
130                 135                 140

Pro Ser Ser Thr Val Thr Leu Gly Cys Leu Val Lys Gly Tyr Leu Pro
145                 150                 155                 160

Glu Pro Val Thr Val Thr Trp Asn Ser Gly Thr Leu Thr Asn Gly Val
                165                 170                 175

Arg Thr Phe Pro Ser Val Arg Gln Ser Ser Gly Leu Tyr Ser Leu Ser
            180                 185                 190

Ser Val Val Ser Val Thr Ser Ser Ser Gln Pro Val Thr Cys Asn Val
        195                 200                 205

Ala His Pro Ala Thr Asn Thr Lys Val Asp Lys Thr Val Ala Pro Ser
210                 215                 220

Thr Cys Ser Lys Pro Thr Cys Pro Pro Pro Glu Leu Leu Gly Gly Pro
225                 230                 235                 240

Ser Val Phe Ile Phe Pro Pro Lys Pro Lys Asp Thr Leu Met Ile Ser
                245                 250                 255

Arg Thr Pro Glu Val Thr Cys Val Val Val Asp Val Ser Gln Asp Asp
            260                 265                 270

Pro Glu Val Gln Phe Thr Trp Tyr Ile Asn Asn Glu Gln Val Arg Thr
        275                 280                 285

Ala Arg Pro Pro Leu Arg Glu Gln Gln Phe Asn Ser Thr Ile Arg Val
290                 295                 300

Val Ser Thr Leu Pro Ile Ala His Gln Asp Trp Leu Arg Gly Lys Glu
305                 310                 315                 320

Phe Lys Cys Lys Val His Asn Lys Ala Leu Pro Ala Pro Ile Glu Lys
                325                 330                 335

Thr Ile Ser Lys Ala Arg Gly Gln Pro Leu Glu Pro Lys Val Tyr Thr
            340                 345                 350
```

-continued

```
Met Gly Pro Pro Arg Glu Glu Leu Ser Ser Arg Ser Val Ser Leu Thr
            355                 360                 365
Cys Met Ile Asn Gly Phe Tyr Pro Ser Asp Ile Ser Val Glu Trp Glu
    370                 375                 380
Lys Asn Gly Lys Ala Glu Asp Asn Tyr Lys Thr Thr Pro Ala Val Leu
385                 390                 395                 400
Asp Ser Asp Gly Ser Tyr Phe Leu Tyr Ser Lys Leu Ser Val Pro Thr
                405                 410                 415
Ser Glu Trp Gln Arg Gly Asp Val Phe Thr Cys Ser Val Met His Glu
            420                 425                 430
Ala Leu His Asn His Tyr Thr Gln Lys Ser Ile Ser Arg Ser Pro Gly
            435                 440                 445
Lys

<210> SEQ ID NO 10
<211> LENGTH: 219
<212> TYPE: PRT
<213> ORGANISM: Artificial Sequence
<220> FEATURE:
<223> OTHER INFORMATION: polypeptide

<400> SEQUENCE: 10

Ala Asp Val Val Met Thr Gln Thr Pro Ser Pro Val Ser Ala Ala Val
1               5                   10                  15
Gly Gly Thr Val Thr Ile Asn Cys Arg Ala Ser Glu Asp Ile Glu Ser
                20                  25                  30
Phe Leu Ala Trp Tyr Gln Gln Lys Pro Gly Gln Pro Pro Lys Leu Leu
            35                  40                  45
Met Ser Arg Thr Ser Thr Leu Glu Ser Gly Val Pro Ser Arg Phe Lys
        50                  55                  60
Gly Ser Gly Ser Gly Thr Glu Phe Thr Leu Thr Ile Ser Asp Leu Glu
65                  70                  75                  80
Cys Ala Asp Ala Ala Thr Tyr Tyr Cys Gln Cys Thr Asp Gly Ser Ser
                85                  90                  95
Ser Ser Ser Ser Tyr Gly Trp Asp Ala Phe Gly Gly Gly Thr Glu Val
                100                 105                 110
Val Val Lys Gly Asp Pro Val Ala Pro Thr Val Leu Leu Phe Pro Pro
            115                 120                 125
Ser Ser Asp Glu Val Ala Thr Gly Thr Val Thr Ile Val Cys Val Ala
        130                 135                 140
Asn Lys Tyr Phe Pro Asp Val Thr Val Thr Trp Glu Val Asp Gly Thr
145                 150                 155                 160
Thr Gln Thr Thr Gly Ile Glu Asn Ser Lys Thr Pro Gln Asn Ser Ala
                165                 170                 175
Asp Cys Thr Tyr Asn Leu Ser Ser Thr Leu Thr Leu Thr Ser Thr Gln
                180                 185                 190
Tyr Asn Ser His Lys Glu Tyr Thr Cys Lys Val Thr Gln Gly Thr Thr
            195                 200                 205
Ser Val Val Gln Ser Phe Ser Arg Lys Asn Cys
    210                 215

<210> SEQ ID NO 11
<211> LENGTH: 450
<212> TYPE: PRT
<213> ORGANISM: Artificial Sequence
<220> FEATURE:
<223> OTHER INFORMATION: polypeptide
```

<400> SEQUENCE: 11

```
Gln Ser Leu Glu Glu Ser Gly Gly Leu Val Gln Pro Gly Ala Ser
1               5                   10                  15

Leu Thr Leu Thr Cys Thr Ala Ser Gly Phe Ser Phe Ser Ser Asn Tyr
            20                  25                  30

Tyr Met Cys Trp Val Arg Gln Ala Pro Gly Lys Gly Leu Glu Trp Ile
        35                  40                  45

Ala Cys Ile Phe Thr Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu His Val Thr Ser Leu Thr Ala Ala Asp Thr Ala Thr Tyr Phe Cys
                85                  90                  95

Ala Arg Asp Arg Ala Leu Ser Val Val Gly Tyr Phe Tyr Ala Ala Tyr
            100                 105                 110

Tyr Phe Asp Phe Trp Gly Pro Gly Thr Leu Val Thr Val Ser Ser Gly
        115                 120                 125

Gln Pro Lys Ala Pro Ser Val Phe Pro Leu Ala Pro Cys Cys Gly Asp
    130                 135                 140

Thr Pro Ser Ser Thr Val Thr Leu Gly Cys Leu Val Lys Gly Tyr Leu
145                 150                 155                 160

Pro Glu Pro Val Thr Val Thr Trp Asn Ser Gly Thr Leu Thr Asn Gly
                165                 170                 175

Val Arg Thr Phe Pro Ser Val Arg Gln Ser Ser Gly Leu Tyr Ser Leu
            180                 185                 190

Ser Ser Val Val Ser Val Thr Ser Ser Ser Gln Pro Val Thr Cys Asn
        195                 200                 205

Val Ala His Pro Ala Thr Asn Thr Lys Val Asp Lys Thr Val Ala Pro
    210                 215                 220

Ser Thr Cys Ser Lys Pro Thr Cys Pro Pro Glu Leu Leu Gly Gly
225                 230                 235                 240

Pro Ser Val Phe Ile Phe Pro Pro Lys Pro Lys Asp Thr Leu Met Ile
                245                 250                 255

Ser Arg Thr Pro Glu Val Thr Cys Val Val Val Asp Val Ser Gln Asp
            260                 265                 270

Asp Pro Glu Val Gln Phe Thr Trp Tyr Ile Asn Asn Glu Gln Val Arg
        275                 280                 285

Thr Ala Arg Pro Pro Leu Arg Glu Gln Gln Phe Asn Ser Thr Ile Arg
    290                 295                 300

Val Val Ser Thr Leu Pro Ile Ala His Gln Asp Trp Leu Arg Gly Lys
305                 310                 315                 320

Glu Phe Lys Cys Lys Val His Asn Lys Ala Leu Pro Ala Pro Ile Glu
                325                 330                 335

Lys Thr Ile Ser Lys Ala Arg Gly Gln Pro Leu Glu Pro Lys Val Tyr
            340                 345                 350

Thr Met Gly Pro Pro Arg Glu Glu Leu Ser Ser Arg Ser Val Ser Leu
        355                 360                 365

Thr Cys Met Ile Asn Gly Phe Tyr Pro Ser Asp Ile Ser Val Glu Trp
    370                 375                 380

Glu Lys Asn Gly Lys Ala Glu Asp Asn Tyr Lys Thr Thr Pro Ala Val
385                 390                 395                 400

Leu Asp Ser Asp Gly Ser Tyr Phe Leu Tyr Ser Lys Leu Ser Val Pro
```

```
                    405                 410                 415

Thr Ser Glu Trp Gln Arg Gly Asp Val Phe Thr Cys Ser Val Met His
            420                 425                 430

Glu Ala Leu His Asn His Tyr Thr Gln Lys Ser Ile Ser Arg Ser Pro
        435                 440                 445

Gly Lys
    450

<210> SEQ ID NO 12
<211> LENGTH: 217
<212> TYPE: PRT
<213> ORGANISM: Artificial Sequence
<220> FEATURE:
<223> OTHER INFORMATION: polypeptide

<400> SEQUENCE: 12

Ala Asp Ile Val Met Thr Gln Thr Pro Ala Ser Val Ser Gly Ala Val
1               5                   10                  15

Gly Gly Thr Val Thr Ile Lys Cys Gln Ala Ser Gln Ser Ile Arg Asn
            20                  25                  30

Glu Leu Ser Trp Tyr Gln Gln Lys Pro Gly Gln Pro Pro Lys Leu Leu
        35                  40                  45

Ile Tyr Lys Ala Ser Thr Leu Ala Ser Gly Val Pro Ser Arg Phe Ser
    50                  55                  60

Gly Ser Gly Phe Gly Thr Glu Phe Thr Leu Thr Ile Ser Gly Val Gln
65                  70                  75                  80

Cys Asp Asp Ala Ala Thr Tyr Tyr Cys Gln Asn Asn Tyr Gly Thr Arg
                85                  90                  95

Arg Asn Asn Tyr Val Phe Pro Phe Gly Gly Gly Thr Glu Val Val Val
            100                 105                 110

Lys Gly Asp Pro Val Ala Pro Thr Val Leu Leu Phe Pro Pro Ser Ser
        115                 120                 125

Asp Glu Val Ala Thr Gly Thr Val Thr Ile Val Cys Val Ala Asn Lys
    130                 135                 140

Tyr Phe Pro Asp Val Thr Val Thr Trp Glu Val Asp Gly Thr Thr Gln
145                 150                 155                 160

Thr Thr Gly Ile Glu Asn Ser Lys Pro Gln Asn Ser Ala Asp Cys
                165                 170                 175

Thr Tyr Asn Leu Ser Ser Thr Leu Thr Leu Thr Ser Thr Gln Tyr Asn
            180                 185                 190

Ser His Lys Glu Tyr Thr Cys Lys Val Thr Gln Gly Thr Thr Ser Val
        195                 200                 205

Val Gln Ser Phe Ser Arg Lys Asn Cys
    210                 215

<210> SEQ ID NO 13
<211> LENGTH: 440
<212> TYPE: PRT
<213> ORGANISM: Artificial Sequence
<220> FEATURE:
<223> OTHER INFORMATION: polypeptide

<400> SEQUENCE: 13

Gln Ser Val Glu Glu Ser Gly Gly Arg Leu Val Thr Pro Gly Thr Pro
1               5                   10                  15

Leu Thr Leu Thr Cys Thr Ala Ser Gly Ile Asp Leu Ser Ser Tyr Ala
            20                  25                  30
```

```
Met Ile Trp Val Arg Gln Ala Pro Gly Glu Gly Leu Glu Tyr Ile Gly
             35                  40                  45
Phe Ile Asp Ala Gly Asp Gly Asn Thr Tyr Tyr Ala Ser Trp Ala Lys
 50                  55                  60
Gly Arg Phe Thr Ile Ser Lys Thr Ser Thr Thr Val Asp Leu Lys Ile
 65                  70                  75                  80
Thr Ser Pro Thr Thr Glu Asp Thr Ala Thr Tyr Phe Cys Ala Arg Gly
                 85                  90                  95
Asp Pro Gly Trp Ser Asn Gly Phe Ala Leu Trp Gly Gln Gly Thr Leu
                100                 105                 110
Val Thr Val Ser Ser Gly Gln Pro Lys Ala Pro Ser Val Phe Pro Leu
            115                 120                 125
Ala Pro Cys Cys Gly Asp Thr Pro Ser Ser Thr Val Thr Leu Gly Cys
130                 135                 140
Leu Val Lys Gly Tyr Leu Pro Glu Pro Val Thr Val Thr Trp Asn Ser
145                 150                 155                 160
Gly Thr Leu Thr Asn Gly Val Arg Thr Phe Pro Ser Val Arg Gln Ser
                165                 170                 175
Ser Gly Leu Tyr Ser Leu Ser Ser Val Val Ser Val Thr Ser Ser Ser
            180                 185                 190
Gln Pro Val Thr Cys Asn Val Ala His Pro Ala Thr Asn Thr Lys Val
                195                 200                 205
Asp Lys Thr Val Ala Pro Ser Thr Cys Ser Lys Pro Thr Cys Pro Pro
210                 215                 220
Pro Glu Leu Leu Gly Gly Pro Ser Val Phe Ile Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser Gln Asp Asp Pro Glu Val Gln Phe Thr Trp Tyr Ile
            260                 265                 270
Asn Asn Glu Gln Val Arg Thr Ala Arg Pro Pro Leu Arg Glu Gln Gln
                275                 280                 285
Phe Asn Ser Thr Ile Arg Val Val Ser Thr Leu Pro Ile Ala His Gln
290                 295                 300
Asp Trp Leu Arg Gly Lys Glu Phe Lys Cys Lys Val His Asn Lys Ala
305                 310                 315                 320
Leu Pro Ala Pro Ile Glu Lys Thr Ile Ser Lys Ala Arg Gly Gln Pro
                325                 330                 335
Leu Glu Pro Lys Val Tyr Thr Met Gly Pro Pro Arg Glu Glu Leu Ser
            340                 345                 350
Ser Arg Ser Val Ser Leu Thr Cys Met Ile Asn Gly Phe Tyr Pro Ser
                355                 360                 365
Asp Ile Ser Val Glu Trp Glu Lys Asn Gly Lys Ala Glu Asp Asn Tyr
370                 375                 380
Lys Thr Thr Pro Ala Val Leu Asp Ser Asp Gly Ser Tyr Phe Leu Tyr
385                 390                 395                 400
Ser Lys Leu Ser Val Pro Thr Ser Glu Trp Gln Arg Gly Asp Val Phe
                405                 410                 415
Thr Cys Ser Val Met His Glu Ala Leu His Asn His Tyr Thr Gln Lys
            420                 425                 430
Ser Ile Ser Arg Ser Pro Gly Lys
                435                 440
```

-continued

```
<210> SEQ ID NO 14
<211> LENGTH: 215
<212> TYPE: PRT
<213> ORGANISM: Artificial Sequence
<220> FEATURE:
<223> OTHER INFORMATION: polypeptide

<400> SEQUENCE: 14

Ala Asp Ile Val Leu Thr Gln Thr Pro Ala Ser Val Ser Ala Val
1               5                   10                  15

Gly Gly Thr Val Ser Ile Ser Cys Gln Ser Ser Glu Ser Val Tyr Asn
                20                  25                  30

Asn Asn Tyr Leu Ser Trp Phe Gln Gln Lys Pro Gly Gln Pro Pro Lys
            35                  40                  45

Leu Leu Ile Tyr Gly Ala Ser Thr Leu Ala Ser Gly Val Pro Ser Arg
        50                  55                  60

Phe Glu Gly Ser Gly Ser Gly Thr Gln Phe Thr Leu Thr Ile Ser Asp
65                  70                  75                  80

Val Gln Cys Asp Asp Ala Ala Thr Tyr Tyr Cys Leu Gly Asp Tyr Ile
                85                  90                  95

Ile Ile Glu Asn Ile Phe Gly Gly Gly Thr Glu Val Val Val Lys Gly
            100                 105                 110

Asp Pro Val Ala Pro Thr Val Leu Leu Phe Pro Pro Ser Ser Asp Glu
        115                 120                 125

Val Ala Thr Gly Thr Val Thr Ile Val Cys Val Ala Asn Lys Tyr Phe
    130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
        195                 200                 205

Ser Phe Ser Arg Lys Asn Cys
    210                 215

<210> SEQ ID NO 15
<211> LENGTH: 440
<212> TYPE: PRT
<213> ORGANISM: Artificial Sequence
<220> FEATURE:
<223> OTHER INFORMATION: polypeptide

<400> SEQUENCE: 15

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Asn
                20                  25                  30

Met Cys Trp Val Arg Gln Ala Pro Gly Lys Gly Leu Glu Trp Val Gly
            35                  40                  45

Phe Ile Asn Ser Asp Asp Ser Ala Tyr Tyr Ala Ser Trp Ala Lys Gly
        50                  55                  60

Arg Phe Thr Phe Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Tyr Asp
                85                  90                  95
```

```
Trp Asp Tyr Tyr Tyr Ser Arg Leu Asp Leu Trp Gly Pro Gly Thr Leu
            100                 105                 110

Val Thr Val Ser Ser Gly Gln Pro Lys Ala Pro Ser Val Phe Pro Leu
        115                 120                 125

Ala Pro Cys Cys Gly Asp Thr Pro Ser Ser Thr Val Thr Leu Gly Cys
    130                 135                 140

Leu Val Lys Gly Tyr Leu Pro Glu Pro Val Thr Val Thr Trp Asn Ser
145                 150                 155                 160

Gly Thr Leu Thr Asn Gly Val Arg Thr Phe Pro Ser Val Arg Gln Ser
                165                 170                 175

Ser Gly Leu Tyr Ser Leu Ser Ser Val Val Ser Val Thr Ser Ser Ser
            180                 185                 190

Gln Pro Val Thr Cys Asn Val Ala His Pro Ala Thr Asn Thr Lys Val
        195                 200                 205

Asp Lys Thr Val Ala Pro Ser Thr Cys Ser Lys Pro Thr Cys Pro Pro
210                 215                 220

Pro Glu Leu Leu Gly Gly Pro Ser Val Phe Ile Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Asp Asp Pro Glu Val Gln Phe Thr Trp Tyr Ile
            260                 265                 270

Asn Asn Glu Gln Val Arg Thr Ala Arg Pro Pro Leu Arg Glu Gln Gln
        275                 280                 285

Phe Asn Ser Thr Ile Arg Val Val Ser Thr Leu Pro Ile Ala His Gln
290                 295                 300

Asp Trp Leu Arg Gly Lys Glu Phe Lys Cys Lys Val His Asn Lys Ala
305                 310                 315                 320

Leu Pro Ala Pro Ile Glu Lys Thr Ile Ser Lys Ala Arg Gly Gln Pro
                325                 330                 335

Leu Glu Pro Lys Val Tyr Thr Met Gly Pro Pro Arg Glu Glu Leu Ser
            340                 345                 350

Ser Arg Ser Val Ser Leu Thr Cys Met Ile Asn Gly Phe Tyr Pro Ser
        355                 360                 365

Asp Ile Ser Val Glu Trp Glu Lys Asn Gly Lys Ala Glu Asp Asn Tyr
370                 375                 380

Lys Thr Thr Pro Ala Val Leu Asp Ser Asp Gly Ser Tyr Phe Leu Tyr
385                 390                 395                 400

Ser Lys Leu Ser Val Pro Thr Ser Glu Trp Gln Arg Gly Asp Val Phe
                405                 410                 415

Thr Cys Ser Val Met His Glu Ala Leu His Asn His Tyr Thr Gln Lys
            420                 425                 430

Ser Ile Ser Arg Ser Pro Gly Lys
            435                 440

<210> SEQ ID NO 16
<211> LENGTH: 213
<212> TYPE: PRT
<213> ORGANISM: Artificial Sequence
<220> FEATURE:
<223> OTHER INFORMATION: polypeptide

<400> SEQUENCE: 16

Ala Gln Val Leu Thr Gln Thr Pro Ala Ser Val Ser Ala Ala Val Gly
1               5                   10                  15
```

```
Gly Thr Val Thr Ile Asn Cys Gln Ala Ser Gln Ser Val Tyr Asn Asn
                20                  25                  30

Lys Asn Leu Ala Trp Tyr Gln Gln Lys Pro Gly Gln Pro Pro Lys Leu
            35                  40                  45

Leu Ile Tyr Phe Ser Ser Thr Leu Ala Ser Gly Val Pro Ser Arg Phe
    50                  55                  60

Arg Gly Ser Gly Ser Gly Thr Gln Phe Thr Leu Thr Ile Ser Gly Val
65                  70                  75                  80

Gln Cys Gly Asp Ala Ala Thr Tyr Tyr Cys Leu Gly Glu Phe Gly Ser
                85                  90                  95

Ile Trp Ala Phe Gly Gly Gly Thr Glu Val Val Lys Gly Asp Pro
            100                 105                 110

Val Ala Pro Thr Val Leu Leu Phe Pro Pro Ser Ser Asp Glu Val Ala
        115                 120                 125

Thr Gly Thr Val Thr Ile Val Cys Val Ala Asn Lys Tyr Phe Pro Asp
        130                 135                 140

Val Thr Val Thr Trp Glu Val Asp Gly Thr Thr Gln Thr Thr Gly Ile
145                 150                 155                 160

Glu Asn Ser Lys Thr Pro Gln Asn Ser Ala Asp Cys Thr Tyr Asn Leu
                165                 170                 175

Ser Ser Thr Leu Thr Leu Thr Ser Thr Gln Tyr Asn Ser His Lys Glu
            180                 185                 190

Tyr Thr Cys Lys Val Thr Gln Gly Thr Thr Ser Val Val Gln Ser Phe
        195                 200                 205

Ser Arg Lys Asn Cys
        210

<210> SEQ ID NO 17
<211> LENGTH: 440
<212> TYPE: PRT
<213> ORGANISM: Artificial Sequence
<220> FEATURE:
<223> OTHER INFORMATION: polypeptide

<400> SEQUENCE: 17

Gln Leu Glu Glu Ser Gly Gly Gly Leu Val Gln Pro Gly Ala Ser Leu
1               5                   10                  15

Thr Leu Thr Cys Thr Thr Ser Gly Phe Ser Leu Ser Asp Asn Tyr Leu
                20                  25                  30

Cys Trp Val Arg Gln Ala Pro Gly Arg Gly Leu Glu Trp Val Ala Cys
            35                  40                  45

Ile Gly Ile Val Leu Arg Ser Thr Gly Ala Thr Tyr Tyr Ala Ser Trp
    50                  55                  60

Ala Glu Gly Arg Phe Thr Ile Ser Lys Thr Ser Pro Thr Thr Val Thr
65                  70                  75                  80

Leu Glu Met Thr Ser Leu Thr Ala Ala Asp Thr Ala Thr Tyr Phe Cys
                85                  90                  95

Ala Leu Asp Leu Gly Tyr Gly Gly Pro Leu Trp Gly Pro Gly Thr Leu
            100                 105                 110

Val Thr Val Ser Ser Gly Gln Pro Lys Ala Pro Ser Val Phe Pro Leu
        115                 120                 125

Ala Pro Cys Cys Gly Asp Thr Pro Ser Ser Thr Val Thr Leu Gly Cys
        130                 135                 140

Leu Val Lys Gly Tyr Leu Pro Glu Pro Val Thr Val Thr Trp Asn Ser
145                 150                 155                 160
```

```
Gly Thr Leu Thr Asn Gly Val Arg Thr Phe Pro Ser Val Arg Gln Ser
                165                 170                 175
Ser Gly Leu Tyr Ser Leu Ser Ser Val Val Ser Val Thr Ser Ser Ser
            180                 185                 190
Gln Pro Val Thr Cys Asn Val Ala His Pro Ala Thr Asn Thr Lys Val
        195                 200                 205
Asp Lys Thr Val Ala Pro Ser Thr Cys Ser Lys Pro Thr Cys Pro Pro
    210                 215                 220
Pro Glu Leu Leu Gly Gly Pro Ser Val Phe Ile Phe Pro Pro Lys Pro
225                 230                 235                 240
Lys Asp Thr Leu Met Ile Ser Arg Thr Pro Glu Val Thr Cys Val Val
                245                 250                 255
Val Asp Val Ser Gln Asp Asp Pro Glu Val Gln Phe Thr Trp Tyr Ile
            260                 265                 270
Asn Asn Glu Gln Val Arg Thr Ala Arg Pro Pro Leu Arg Glu Gln Gln
        275                 280                 285
Phe Asn Ser Thr Ile Arg Val Val Ser Thr Leu Pro Ile Ala His Gln
    290                 295                 300
Asp Trp Leu Arg Gly Lys Glu Phe Lys Cys Lys Val His Asn Lys Ala
305                 310                 315                 320
Leu Pro Ala Pro Ile Glu Lys Thr Ile Ser Lys Ala Arg Gly Gln Pro
                325                 330                 335
Leu Glu Pro Lys Val Tyr Thr Met Gly Pro Pro Arg Glu Glu Leu Ser
            340                 345                 350
Ser Arg Ser Val Ser Leu Thr Cys Met Ile Asn Gly Phe Tyr Pro Ser
        355                 360                 365
Asp Ile Ser Val Glu Trp Glu Lys Asn Gly Lys Ala Glu Asp Asn Tyr
    370                 375                 380
Lys Thr Thr Pro Ala Val Leu Asp Ser Asp Gly Ser Tyr Phe Leu Tyr
385                 390                 395                 400
Ser Lys Leu Ser Val Pro Thr Ser Glu Trp Gln Arg Gly Asp Val Phe
                405                 410                 415
Thr Cys Ser Val Met His Glu Ala Leu His Asn His Tyr Thr Gln Lys
            420                 425                 430
Ser Ile Ser Arg Ser Pro Gly Lys
        435                 440

<210> SEQ ID NO 18
<211> LENGTH: 116
<212> TYPE: PRT
<213> ORGANISM: Artificial Sequence
<220> FEATURE:
<223> OTHER INFORMATION: polypeptide

<400> SEQUENCE: 18

Ala Asp Val Val Met Thr Gln Thr Pro Ser Pro Val Ser Ala Ala Val
1               5                   10                  15
Gly Gly Thr Val Thr Ile Asn Cys Arg Ala Ser Glu Asp Ile Glu Ser
            20                  25                  30
Phe Leu Ala Trp Tyr Gln Gln Lys Pro Gly Gln Pro Pro Lys Leu Leu
        35                  40                  45
Ile Ser Arg Thr Ser Thr Leu Glu Ser Gly Val Ser Ser Arg Phe Lys
    50                  55                  60
Gly Ser Gly Ser Gly Thr Glu Phe Ile Leu Thr Ile Ser Asp Leu Glu
65                  70                  75                  80
```

```
Cys Ala Asp Ala Ala Thr Tyr Tyr Cys Gln Cys Thr Asp Gly Ser Ser
                85                  90                  95

Ser Ser Ser Ser Tyr Gly Trp Asp Ala Phe Gly Gly Thr Glu Val
            100                 105                 110

Val Val Lys Gly
        115

<210> SEQ ID NO 19
<211> LENGTH: 126
<212> TYPE: PRT
<213> ORGANISM: Artificial Sequence
<220> FEATURE:
<223> OTHER INFORMATION: polypeptide

<400> SEQUENCE: 19

Gln Ser Leu Glu Glu Ser Gly Gly Asp Leu Val Lys Pro Gly Ala Ser
1               5                   10                  15

Leu Thr Leu Thr Cys Lys Ala Ser Gly Ile Ala Phe Ser Asn Asp Tyr
            20                  25                  30

Met Cys Trp Val Arg Gln Ala Pro Gly Lys Gly Leu Glu Trp Ile Ala
        35                  40                  45

Cys Ile Phe Thr Gly Ser Ser Gly Ser Thr Tyr Tyr Ala Ser Trp Ala
50                  55                  60

Lys Gly Arg Phe Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Arg Ala Ile Ser Val Leu Gly Tyr Phe Tyr Ala Ala Tyr Phe
            100                 105                 110

Phe Asp Phe Trp Gly Pro Gly Thr Leu Val Thr Val Ser Ser
        115                 120                 125

<210> SEQ ID NO 20
<211> LENGTH: 116
<212> TYPE: PRT
<213> ORGANISM: Artificial Sequence
<220> FEATURE:
<223> OTHER INFORMATION: polypeptide

<400> SEQUENCE: 20

Ala Asp Val Val Met Thr Gln Thr Pro Ser Pro Val Ser Ala Gln Val
1               5                   10                  15

Gly Gly Thr Val Thr Ile Asn Cys Gln Ala Ser Glu Ser Ile Asp Ser
            20                  25                  30

Asp Leu Ser Trp Tyr Gln Gln Lys Pro Gly Gln Pro Pro Lys Leu Leu
        35                  40                  45

Ile Tyr Arg Thr Phe Thr Leu Glu Ser Gly Val Pro Ser Arg Phe Lys
50                  55                  60

Gly Ser Gly Ser Gly Thr Asp Tyr Thr Leu Thr Ile Ser Asp Leu Glu
65                  70                  75                  80

Cys Ala Asp Ala Ala Ile Tyr Tyr Cys Gln Cys Thr Asp Gly Ser Ser
                85                  90                  95

Ile Ser Gly Ser Tyr Gly Trp Asp Ala Phe Gly Gly Thr Glu Val
            100                 105                 110

Val Val Lys Gly
        115

<210> SEQ ID NO 21
```

```
<211> LENGTH: 126
<212> TYPE: PRT
<213> ORGANISM: Artificial Sequence
<220> FEATURE:
<223> OTHER INFORMATION: polypeptide

<400> SEQUENCE: 21

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Asn Ser Ser Ser
            20                  25                  30

Tyr Met Cys Trp Val Arg Gln Ala Pro Gly Lys Gly Leu Glu Trp Ile
        35                  40                  45

Gly Cys Ile Phe Thr Gly Ser Ser Gly Asn Thr Tyr Tyr Ala Thr Trp
    50                  55                  60

Ala Gln Gly Arg Phe Thr Ile Ser Lys Thr Ser Thr Val Thr Leu
65                  70                  75                  80

Glu Met Thr Ser Leu Thr Ala Ala Asp Thr Ala Thr Tyr Phe Cys Ala
                85                  90                  95

Arg Asp Arg Ala Tyr Phe Leu Val Gly Tyr Phe Tyr Ala Thr Tyr Tyr
            100                 105                 110

Phe Asp Leu Trp Gly Pro Gly Thr Leu Val Thr Val Ser Ser
        115                 120                 125

<210> SEQ ID NO 22
<211> LENGTH: 116
<212> TYPE: PRT
<213> ORGANISM: Artificial Sequence
<220> FEATURE:
<223> OTHER INFORMATION: polypeptide

<400> SEQUENCE: 22

Ala Asp Val Val Met Thr Gln Thr Pro Ser Pro Val Ser Ala Ala Val
1               5                   10                  15

Gly Gly Thr Val Thr Ile Asn Cys Arg Ala Ser Glu Asp Ile Glu Ser
            20                  25                  30

Phe Leu Ala Trp Tyr Gln Gln Lys Pro Gly Gln Pro Pro Lys Leu Leu
        35                  40                  45

Met Ser Arg Thr Ser Thr Leu Glu Ser Gly Val Pro Ser Arg Phe Lys
    50                  55                  60

Gly Ser Gly Ser Gly Thr Glu Phe Thr Leu Thr Ile Ser Asp Leu Glu
65                  70                  75                  80

Cys Ala Asp Ala Ala Thr Tyr Tyr Cys Gln Cys Thr Asp Gly Ser Ser
                85                  90                  95

Ser Ser Ser Ser Tyr Gly Trp Asp Ala Phe Gly Gly Gly Thr Glu Val
            100                 105                 110

Val Val Lys Gly
        115

<210> SEQ ID NO 23
<211> LENGTH: 127
<212> TYPE: PRT
<213> ORGANISM: Artificial Sequence
<220> FEATURE:
<223> OTHER INFORMATION: polypeptide

<400> SEQUENCE: 23

Gln Ser Leu Glu Glu Ser Gly Gly Gly Leu Val Gln Pro Gly Ala Ser
1               5                   10                  15
```

-continued

```
Leu Thr Leu Thr Cys Thr Ala Ser Gly Phe Ser Phe Ser Ser Asn Tyr
            20                  25                  30

Tyr Met Cys Trp Val Arg Gln Ala Pro Gly Lys Gly Leu Glu Trp Ile
        35                  40                  45

Ala Cys Ile Phe Thr Gly Ser Ser Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu His Val Thr Ser Leu Thr Ala Ala Asp Thr Ala Thr Tyr Phe Cys
                85                  90                  95

Ala Arg Asp Arg Ala Leu Ser Val Val Gly Tyr Phe Tyr Ala Ala Tyr
            100                 105                 110

Tyr Phe Asp Phe Trp Gly Pro Gly Thr Leu Val Thr Val Ser Ser
        115                 120                 125
```

<210> SEQ ID NO 24
<211> LENGTH: 114
<212> TYPE: PRT
<213> ORGANISM: Artificial Sequence
<220> FEATURE:
<223> OTHER INFORMATION: polypeptide

<400> SEQUENCE: 24

```
Ala Asp Ile Val Met Thr Gln Thr Pro Ala Ser Val Ser Gly Ala Val
1               5                   10                  15

Gly Gly Thr Val Thr Ile Lys Cys Gln Ala Ser Gln Ser Ile Arg Asn
            20                  25                  30

Glu Leu Ser Trp Tyr Gln Gln Lys Pro Gly Gln Pro Pro Lys Leu Leu
        35                  40                  45

Ile Tyr Lys Ala Ser Thr Leu Ala Ser Gly Val Pro Ser Arg Phe Ser
    50                  55                  60

Gly Ser Gly Phe Gly Thr Glu Phe Thr Leu Thr Ile Ser Gly Val Gln
65                  70                  75                  80

Cys Asp Asp Ala Ala Thr Tyr Tyr Cys Gln Asn Asn Tyr Gly Thr Arg
                85                  90                  95

Arg Asn Asn Tyr Val Phe Pro Phe Gly Gly Gly Thr Glu Val Val Val
            100                 105                 110

Lys Gly
```

<210> SEQ ID NO 25
<211> LENGTH: 117
<212> TYPE: PRT
<213> ORGANISM: Artificial Sequence
<220> FEATURE:
<223> OTHER INFORMATION: polypeptide

<400> SEQUENCE: 25

```
Gln Ser Val Glu Glu Ser Gly Gly Arg Leu Val Thr Pro Gly Thr Pro
1               5                   10                  15

Leu Thr Leu Thr Cys Thr Ala Ser Gly Ile Asp Leu Ser Ser Tyr Ala
            20                  25                  30

Met Ile Trp Val Arg Gln Ala Pro Gly Glu Gly Leu Glu Tyr Ile Gly
        35                  40                  45

Phe Ile Asp Ala Gly Asp Gly Asn Thr Tyr Tyr Ala Ser Trp Ala Lys
    50                  55                  60

Gly Arg Phe Thr Ile Ser Lys Thr Ser Thr Thr Val Asp Leu Lys Ile
65                  70                  75                  80
```

```
Thr Ser Pro Thr Thr Glu Asp Thr Ala Thr Tyr Phe Cys Ala Arg Gly
                85                  90                  95

Asp Pro Gly Trp Ser Asn Gly Phe Ala Leu Trp Gly Gln Gly Thr Leu
            100                 105                 110

Val Thr Val Ser Ser
            115

<210> SEQ ID NO 26
<211> LENGTH: 112
<212> TYPE: PRT
<213> ORGANISM: Artificial Sequence
<220> FEATURE:
<223> OTHER INFORMATION: polypeptide

<400> SEQUENCE: 26

Ala Asp Ile Val Leu Thr Gln Thr Pro Ala Ser Val Ser Ala Ala Val
1               5                   10                  15

Gly Gly Thr Val Ser Ile Ser Cys Gln Ser Ser Glu Ser Val Tyr Asn
            20                  25                  30

Asn Asn Tyr Leu Ser Trp Phe Gln Gln Lys Pro Gly Gln Pro Pro Lys
        35                  40                  45

Leu Leu Ile Tyr Gly Ala Ser Thr Leu Ala Ser Gly Val Pro Ser Arg
    50                  55                  60

Phe Glu Gly Ser Gly Ser Gly Thr Gln Phe Thr Leu Thr Ile Ser Asp
65                  70                  75                  80

Val Gln Cys Asp Asp Ala Ala Thr Tyr Tyr Cys Leu Gly Asp Tyr Ile
                85                  90                  95

Ile Ile Glu Asn Ile Phe Gly Gly Gly Thr Glu Val Val Val Lys Gly
            100                 105                 110

<210> SEQ ID NO 27
<211> LENGTH: 117
<212> TYPE: PRT
<213> ORGANISM: Artificial Sequence
<220> FEATURE:
<223> OTHER INFORMATION: polypeptide

<400> SEQUENCE: 27

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Asn
            20                  25                  30

Met Cys Trp Val Arg Gln Ala Pro Gly Lys Gly Leu Glu Trp Val Gly
        35                  40                  45

Phe Ile Asn Ser Asp Asp Ser Ala Tyr Tyr Ala Ser Trp Ala Lys Gly
    50                  55                  60

Arg Phe Thr Phe Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Tyr Asp
                85                  90                  95

Trp Asp Tyr Tyr Tyr Ser Arg Leu Asp Leu Trp Gly Pro Gly Thr Leu
            100                 105                 110

Val Thr Val Ser Ser
            115

<210> SEQ ID NO 28
<211> LENGTH: 110
<212> TYPE: PRT
<213> ORGANISM: Artificial Sequence
```

<220> FEATURE:
<223> OTHER INFORMATION: polypeptide

<400> SEQUENCE: 28

Ala Gln Val Leu Thr Gln Thr Pro Ala Ser Val Ser Ala Ala Val Gly
1               5                   10                  15

Gly Thr Val Thr Ile Asn Cys Gln Ala Ser Gln Ser Val Tyr Asn Asn
                20                  25                  30

Lys Asn Leu Ala Trp Tyr Gln Gln Lys Pro Gly Gln Pro Pro Lys Leu
            35                  40                  45

Leu Ile Tyr Phe Ser Ser Thr Leu Ala Ser Gly Val Pro Ser Arg Phe
    50                  55                  60

Arg Gly Ser Gly Ser Gly Thr Gln Phe Thr Leu Thr Ile Ser Gly Val
65                  70                  75                  80

Gln Cys Gly Asp Ala Ala Thr Tyr Tyr Cys Leu Gly Glu Phe Gly Ser
                85                  90                  95

Ile Trp Ala Phe Gly Gly Gly Thr Glu Val Val Val Lys Gly
            100                 105                 110

<210> SEQ ID NO 29
<211> LENGTH: 117
<212> TYPE: PRT
<213> ORGANISM: Artificial Sequence
<220> FEATURE:
<223> OTHER INFORMATION: polypeptide

<400> SEQUENCE: 29

Gln Leu Glu Glu Ser Gly Gly Gly Leu Val Gln Pro Gly Ala Ser Leu
1               5                   10                  15

Thr Leu Thr Cys Thr Thr Ser Gly Phe Ser Leu Ser Asp Asn Tyr Leu
                20                  25                  30

Cys Trp Val Arg Gln Ala Pro Gly Arg Gly Leu Glu Trp Val Ala Cys
            35                  40                  45

Ile Gly Ile Val Leu Arg Ser Thr Gly Ala Thr Tyr Tyr Ala Ser Trp
    50                  55                  60

Ala Glu Gly Arg Phe Thr Ile Ser Lys Thr Ser Pro Thr Thr Val Thr
65                  70                  75                  80

Leu Glu Met Thr Ser Leu Thr Ala Ala Asp Thr Ala Thr Tyr Phe Cys
                85                  90                  95

Ala Leu Asp Leu Gly Tyr Gly Gly Pro Leu Trp Gly Pro Gly Thr Leu
            100                 105                 110

Val Thr Val Ser Ser
            115

<210> SEQ ID NO 30
<211> LENGTH: 11
<212> TYPE: PRT
<213> ORGANISM: Artificial Sequence
<220> FEATURE:
<223> OTHER INFORMATION: polypeptide

<400> SEQUENCE: 30

Arg Ala Ser Glu Asp Ile Glu Ser Phe Leu Ala
1               5                   10

<210> SEQ ID NO 31
<211> LENGTH: 11
<212> TYPE: PRT
<213> ORGANISM: Artificial Sequence
<220> FEATURE:

```
<223> OTHER INFORMATION: polypeptide

<400> SEQUENCE: 31

Gln Ala Ser Glu Ser Ile Asp Ser Asp Leu Ser
1               5                   10

<210> SEQ ID NO 32
<211> LENGTH: 11
<212> TYPE: PRT
<213> ORGANISM: Artificial Sequence
<220> FEATURE:
<223> OTHER INFORMATION: polypeptide

<400> SEQUENCE: 32

Gln Ala Ser Gln Ser Ile Arg Asn Glu Leu Ser
1               5                   10

<210> SEQ ID NO 33
<211> LENGTH: 13
<212> TYPE: PRT
<213> ORGANISM: Artificial Sequence
<220> FEATURE:
<223> OTHER INFORMATION: polypeptide

<400> SEQUENCE: 33

Gln Ser Ser Glu Ser Val Tyr Asn Asn Asn Tyr Leu Ser
1               5                   10

<210> SEQ ID NO 34
<211> LENGTH: 13
<212> TYPE: PRT
<213> ORGANISM: Artificial Sequence
<220> FEATURE:
<223> OTHER INFORMATION: polypeptide

<400> SEQUENCE: 34

Gln Ala Ser Gln Ser Val Tyr Asn Asn Lys Asn Leu Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: polypeptide

<400> SEQUENCE: 35

Arg Thr Ser Thr Leu Glu Ser
1               5

<210> SEQ ID NO 36
<211> LENGTH: 7
<212> TYPE: PRT
<213> ORGANISM: Artificial Sequence
<220> FEATURE:
<223> OTHER INFORMATION: polypeptide

<400> SEQUENCE: 36

Arg Thr Phe Thr Leu Glu Ser
1               5

<210> SEQ ID NO 37
<211> LENGTH: 7
<212> TYPE: PRT
<213> ORGANISM: Artificial Sequence
<220> FEATURE:
<223> OTHER INFORMATION: polypeptide
```

<400> SEQUENCE: 37

Lys Ala Ser Thr Leu Ala Ser
1               5

<210> SEQ ID NO 38
<211> LENGTH: 7
<212> TYPE: PRT
<213> ORGANISM: Artificial Sequence
<220> FEATURE:
<223> OTHER INFORMATION: polypeptide

<400> SEQUENCE: 38

Gly Ala Ser Thr Leu Ala Ser
1               5

<210> SEQ ID NO 39
<211> LENGTH: 7
<212> TYPE: PRT
<213> ORGANISM: Artificial Sequence
<220> FEATURE:
<223> OTHER INFORMATION: polypeptide

<400> SEQUENCE: 39

Phe Ser Ser Thr Leu Ala Ser
1               5

<210> SEQ ID NO 40
<211> LENGTH: 16
<212> TYPE: PRT
<213> ORGANISM: Artificial Sequence
<220> FEATURE:
<223> OTHER INFORMATION: polypeptide

<400> SEQUENCE: 40

Gln Cys Thr Asp Gly Ser Ser Ser Ser Ser Tyr Gly Trp Asp Ala
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: polypeptide

<400> SEQUENCE: 41

Gln Cys Thr Asp Gly Ser Ser Ile Ser Gly Ser Tyr Gly Trp Asp Ala
1               5                   10                  15

<210> SEQ ID NO 42
<211> LENGTH: 14
<212> TYPE: PRT
<213> ORGANISM: Artificial Sequence
<220> FEATURE:
<223> OTHER INFORMATION: polypeptide

<400> SEQUENCE: 42

Gln Asn Asn Tyr Gly Thr Arg Arg Asn Asn Tyr Val Phe Pro
1               5                   10

<210> SEQ ID NO 43
<211> LENGTH: 10
<212> TYPE: PRT
<213> ORGANISM: Artificial Sequence
<220> FEATURE:
<223> OTHER INFORMATION: polypeptide

```
<400> SEQUENCE: 43

Leu Gly Asp Tyr Ile Ile Ile Glu Asn Ile
1               5                   10

<210> SEQ ID NO 44
<211> LENGTH: 9
<212> TYPE: PRT
<213> ORGANISM: Artificial Sequence
<220> FEATURE:
<223> OTHER INFORMATION: polypeptide

<400> SEQUENCE: 44

Leu Gly Glu Phe Gly Ser Ile Trp Ala
1               5

<210> SEQ ID NO 45
<211> LENGTH: 5
<212> TYPE: PRT
<213> ORGANISM: Artificial Sequence
<220> FEATURE:
<223> OTHER INFORMATION: polypeptide

<400> SEQUENCE: 45

Asn Asp Tyr Met Cys
1               5

<210> SEQ ID NO 46
<211> LENGTH: 6
<212> TYPE: PRT
<213> ORGANISM: Artificial Sequence
<220> FEATURE:
<223> OTHER INFORMATION: polypeptide

<400> SEQUENCE: 46

Ser Ser Ser Tyr Met Cys
1               5

<210> SEQ ID NO 47
<211> LENGTH: 6
<212> TYPE: PRT
<213> ORGANISM: Artificial Sequence
<220> FEATURE:
<223> OTHER INFORMATION: polypeptide

<400> SEQUENCE: 47

Ser Asn Tyr Tyr Met Cys
1               5

<210> SEQ ID NO 48
<211> LENGTH: 5
<212> TYPE: PRT
<213> ORGANISM: Artificial Sequence
<220> FEATURE:
<223> OTHER INFORMATION: polypeptide

<400> SEQUENCE: 48

Ser Tyr Ala Met Ile
1               5

<210> SEQ ID NO 49
<211> LENGTH: 5
<212> TYPE: PRT
<213> ORGANISM: Artificial Sequence
<220> FEATURE:
<223> OTHER INFORMATION: polypeptide

<400> SEQUENCE: 49
```

Thr Tyr Asn Met Cys
1               5

<210> SEQ ID NO 50
<211> LENGTH: 5
<212> TYPE: PRT
<213> ORGANISM: Artificial Sequence
<220> FEATURE:
<223> OTHER INFORMATION: polypeptide

<400> SEQUENCE: 50

Asp Asn Tyr Leu Cys
1               5

<210> SEQ ID NO 51
<211> LENGTH: 18
<212> TYPE: PRT
<213> ORGANISM: Artificial Sequence
<220> FEATURE:
<223> OTHER INFORMATION: polypeptide

<400> SEQUENCE: 51

Cys Ile Phe Thr Gly Ser Ser Gly Ser Thr Tyr Tyr Ala Ser Trp Ala
1               5                   10                  15

Lys Gly

<210> SEQ ID NO 52
<211> LENGTH: 18
<212> TYPE: PRT
<213> ORGANISM: Artificial Sequence
<220> FEATURE:
<223> OTHER INFORMATION: polypeptide

<400> SEQUENCE: 52

Cys Ile Phe Thr Gly Ser Ser Gly Asn Thr Tyr Tyr Ala Thr Trp Ala
1               5                   10                  15

Gln Gly

<210> SEQ ID NO 53
<211> LENGTH: 17
<212> TYPE: PRT
<213> ORGANISM: Artificial Sequence
<220> FEATURE:
<223> OTHER INFORMATION: polypeptide

<400> SEQUENCE: 53

Phe Ile Asp Ala Gly Asp Gly Asn Thr Tyr Tyr Ala Ser Trp Ala Lys
1               5                   10                  15

Gly

<210> SEQ ID NO 54
<211> LENGTH: 16
<212> TYPE: PRT
<213> ORGANISM: Artificial Sequence
<220> FEATURE:
<223> OTHER INFORMATION: polypeptide

<400> SEQUENCE: 54

Phe Ile Asn Ser Asp Asp Ser Ala Tyr Tyr Ala Ser Trp Ala Lys Gly
1               5                   10                  15

<210> SEQ ID NO 55
<211> LENGTH: 20
<212> TYPE: PRT

```
<213> ORGANISM: Artificial Sequence
<220> FEATURE:
<223> OTHER INFORMATION: polypeptide

<400> SEQUENCE: 55

Cys Ile Gly Ile Val Leu Arg Ser Thr Gly Ala Thr Tyr Tyr Ala Ser
1               5                   10                  15

Trp Ala Glu Gly
            20

<210> SEQ ID NO 56
<211> LENGTH: 18
<212> TYPE: PRT
<213> ORGANISM: Artificial Sequence
<220> FEATURE:
<223> OTHER INFORMATION: polypeptide

<400> SEQUENCE: 56

Asp Arg Ala Ile Ser Val Leu Gly Tyr Phe Tyr Ala Ala Tyr Phe Phe
1               5                   10                  15

Asp Phe

<210> SEQ ID NO 57
<211> LENGTH: 18
<212> TYPE: PRT
<213> ORGANISM: Artificial Sequence
<220> FEATURE:
<223> OTHER INFORMATION: polypeptide

<400> SEQUENCE: 57

Asp Arg Ala Tyr Phe Leu Val Gly Tyr Phe Tyr Ala Thr Tyr Tyr Phe
1               5                   10                  15

Asp Leu

<210> SEQ ID NO 58
<211> LENGTH: 18
<212> TYPE: PRT
<213> ORGANISM: Artificial Sequence
<220> FEATURE:
<223> OTHER INFORMATION: polypeptide

<400> SEQUENCE: 58

Asp Arg Ala Leu Ser Val Val Gly Tyr Phe Tyr Ala Ala Tyr Tyr Phe
1               5                   10                  15

Asp Phe

<210> SEQ ID NO 59
<211> LENGTH: 11
<212> TYPE: PRT
<213> ORGANISM: Artificial Sequence
<220> FEATURE:
<223> OTHER INFORMATION: polypeptide

<400> SEQUENCE: 59

Gly Asp Pro Gly Trp Ser Asn Gly Phe Ala Leu
1               5                   10

<210> SEQ ID NO 60
<211> LENGTH: 12
<212> TYPE: PRT
<213> ORGANISM: Artificial Sequence
<220> FEATURE:
<223> OTHER INFORMATION: polypeptide

<400> SEQUENCE: 60
```

Tyr Asp Trp Asp Tyr Tyr Tyr Ser Arg Leu Asp Leu
1               5                   10

<210> SEQ ID NO 61
<211> LENGTH: 8
<212> TYPE: PRT
<213> ORGANISM: Artificial Sequence
<220> FEATURE:
<223> OTHER INFORMATION: polypeptide

<400> SEQUENCE: 61

Asp Leu Gly Tyr Gly Gly Pro Leu
1               5

<210> SEQ ID NO 62
<211> LENGTH: 27
<212> TYPE: PRT
<213> ORGANISM: Homo sapiens

<400> SEQUENCE: 62

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20                  25

<210> SEQ ID NO 63
<211> LENGTH: 106
<212> TYPE: PRT
<213> ORGANISM: Homo sapiens

<400> SEQUENCE: 63

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 64
<211> LENGTH: 106
<212> TYPE: PRT
<213> ORGANISM: Homo sapiens

<400> SEQUENCE: 64

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 65
<211> LENGTH: 106
<212> TYPE: PRT
<213> ORGANISM: Homo sapiens

<400> SEQUENCE: 65

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 66
<211> LENGTH: 106
<212> TYPE: PRT
<213> ORGANISM: Homo sapiens

<400> SEQUENCE: 66

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105

<210> SEQ ID NO 67
<211> LENGTH: 330
<212> TYPE: PRT
<213> ORGANISM: Homo sapiens

<400> SEQUENCE: 67

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 330
<212> TYPE: PRT
<213> ORGANISM: Homo sapiens

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 69
<211> LENGTH: 330
<212> TYPE: PRT
<213> ORGANISM: Homo sapiens

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys

```
                100                 105                 110
Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 70
<211> LENGTH: 330
<212> TYPE: PRT
<213> ORGANISM: Homo sapiens

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 71
<211> LENGTH: 326
<212> TYPE: PRT
<213> ORGANISM: Homo sapiens

<400> SEQUENCE: 71

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
        210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
290                 295                 300
Ser Val Met His Glu Ala Leu His Asn His Tyr Thr Gln Lys Ser Leu
                310                 315                 320
305
Ser Leu Ser Pro Gly Lys
                325
```

<210> SEQ ID NO 72
<211> LENGTH: 348
<212> TYPE: DNA
<213> ORGANISM: Artificial Sequence
<220> FEATURE:
<223> OTHER INFORMATION: polynucleotide

<400> SEQUENCE: 72

```
gccgatgtcg tgatgaccca gactccatcc cccgtgtctg cagctgtggg aggcacagtc    60
accatcaatt gccgggccag tgaggacatt gaaagctttt tagcctggta tcagcagaaa   120
ccagggcagc ctcccaagct cctgatctcc aggacatcca ctctggaatc tggggtctca   180
tcgcggttca aaggcagtgg atcggggaca gagttcattc tcaccatcag cgacctggag   240
tgtgccgatg ctgccactta ctactgtcaa tgtactgatg gtagtagtag tagtagtagt   300
tatggttggg atgctttcgg cggagggacc gaggtggtgg tcaaaggt               348
```

<210> SEQ ID NO 73
<211> LENGTH: 348
<212> TYPE: DNA
<213> ORGANISM: Artificial Sequence
<220> FEATURE:
<223> OTHER INFORMATION: polynucleotide

<400> SEQUENCE: 73

```
gccgatgtcg tgatgaccca gactccatcc cccgtgtctg cgcaggtggg aggcacagtc    60
accatcaatt gccaggccag tgagagcatt gatagtgact atcctggta tcaacagaaa   120
ccagggcagc ctcccaagct cctgatctac aggacattca ctctggaatc tggggtccca   180
tcgcggttca aaggcagtgg atctgggaca gactacactc tcaccatcag cgacctggag   240
tgtgccgatg ctgccattta ctactgtcaa tgcactgatg gtagtagtat tagtggtagt   300
tatggttggg atgctttcgg cggagggacc gaggtggtgg tcaaaggt               348
```

<210> SEQ ID NO 74
<211> LENGTH: 348
<212> TYPE: DNA
<213> ORGANISM: Artificial Sequence
<220> FEATURE:
<223> OTHER INFORMATION: polynucleotide

<400> SEQUENCE: 74

| gccgatgtcg tgatgaccca gactccatcc cccgtgtctg cagctgtggg aggcacagtc | 60 |
| accatcaatt gccgggccag tgaggacatt gaaagctttt tagcctggta tcagcagaaa | 120 |
| ccagggcagc ctcccaagct cctgatgtcc aggcatccca ctctggaatc tggggtccca | 180 |
| tcgcggttca aaggcagtgg atctgggaca gagttcactc tcaccatcag cgacctggag | 240 |
| tgtgccgatg ctgccacata ttactgtcaa tgtactgatg gtagtagtag tagtagtagt | 300 |
| tatggttggg atgctttcgg cggagggacc gaggtggtgg tcaaaggt | 348 |

<210> SEQ ID NO 75
<211> LENGTH: 342
<212> TYPE: DNA
<213> ORGANISM: Artificial Sequence
<220> FEATURE:
<223> OTHER INFORMATION: polynucleotide

<400> SEQUENCE: 75

| gctgacattg tgatgaccca gactccagcc tccgtgtctg gagctgtggg aggcacagtc | 60 |
| accatcaagt gccaggccag tcagagcatt aggaatgaat atcctggta tcagcagaaa | 120 |
| ccagggcagc ctcccaagct cctgatctac aaggcatcca ctctggcatc tggggtccca | 180 |
| tcgcggttca gtggcagtgg atttgggaca gagttcactc tcaccatcag cggtgtgcag | 240 |
| tgtgatgatg ctgccactta ctactgtcaa aacaattatg gtactaggcg taataattat | 300 |
| gttttccctt cggcggagg accgaggtg gtggtcaaag gt | 342 |

<210> SEQ ID NO 76
<211> LENGTH: 336
<212> TYPE: DNA
<213> ORGANISM: Artificial Sequence
<220> FEATURE:
<223> OTHER INFORMATION: polynucleotide

<400> SEQUENCE: 76

| gctgacatcg tgctgaccca gactccagcc tccgtgtctg cagctgtggg aggcacagtc | 60 |
| agcatcagtt gccagtccag tgaaagtgtt tataataaca actacttatc ctggtttcag | 120 |
| cagaaaccag gcagcctcc caagctcctg atctatggtg catccactct ggcatctggg | 180 |
| gtcccatcgc ggtttgaagg cagtggatct gggacacagt tcactctcac catcagcgac | 240 |
| gtgcagtgtg atgatgctgc cacttactac tgtctaggcg attatattat tattgagaat | 300 |
| attttcggcg gagggaccga ggtggtggtc aaaggt | 336 |

<210> SEQ ID NO 77
<211> LENGTH: 330
<212> TYPE: DNA
<213> ORGANISM: Artificial Sequence
<220> FEATURE:
<223> OTHER INFORMATION: polynucleotide

<400> SEQUENCE: 77

| gcgcaagtgc tgacccagac tccagcctcc gtgtctgcgg ctgtgggagg cacagtcacc | 60 |
| atcaattgcc aggccagtca gagtgtttat aacaacaaaa atttagcctg gtatcagcag | 120 |
| aaaccagggc agcctcccaa gctcctgatc tattttcat ccactctggc atctggggtc | 180 |
| ccatcgcggt tcagaggcag tggatctggg acacagttca ctctcaccat cagtggcgtg | 240 |
| cagtgtggcg atgctgccac ttactactgt ctaggcgaat tggtagtat ttgggctttc | 300 |

```
ggcggaggga ccgaggtggt ggtcaaaggt                                      330
```

<210> SEQ ID NO 78
<211> LENGTH: 378
<212> TYPE: DNA
<213> ORGANISM: Artificial Sequence
<220> FEATURE:
<223> OTHER INFORMATION: polynucleotide

<400> SEQUENCE: 78

```
cagtcgttgg aggagtccgg gggagacctg gtcaagcctg ggcatctct gacactcacc       60
tgcaaagcct ctggaatcgc cttcagtaac gactacatgt gctgggtccg ccaggctcca     120
gggaaggggc tggagtggat cgcatgtatt tttactggta gtagtggtag tacttactac     180
gcgagctggg cgaaaggtcg attcaccatc tccaaaacct cgtcgaccac ggtgactctg     240
caaatgacca gtctgacagc cgcggacacg gccacctatt tctgtgcgag agatagggct     300
atttctgtac ttggttattt ctatgctgca tacttctttg acttctgggg cccaggcacc     360
ctggtcaccg tctcctca                                                   378
```

<210> SEQ ID NO 79
<211> LENGTH: 378
<212> TYPE: DNA
<213> ORGANISM: Artificial Sequence
<220> FEATURE:
<223> OTHER INFORMATION: polynucleotide

<400> SEQUENCE: 79

```
cagtcgttgg aggagtccgg gggaggcctg gtccagcctg agggatccct gacactcacc       60
tgcacagctt ctggattctc cttcaatagc agctcctaca tgtgctgggt ccgccaggct     120
ccagggaagg ggctggagtg gatcggatgc attttactg gtagtagtgg taatacctac      180
tacgcgacct gggcgcaagg tcgattcacc atctccaaga cctcgaccac ggtgactctg     240
gaaatgacca gtctgacagc cgcggacacg gccacctatt tctgtgcgag agatagggct     300
tattttttgg ttggttattt ctatgctaca tattattttg acttatgggg cccaggcacc     360
ctggtcaccg tctcctca                                                   378
```

<210> SEQ ID NO 80
<211> LENGTH: 381
<212> TYPE: DNA
<213> ORGANISM: Artificial Sequence
<220> FEATURE:
<223> OTHER INFORMATION: polynucleotide

<400> SEQUENCE: 80

```
cagtcgttgg aggagtccgg gggaggcctg gtccagcctg ggcatctct gacactcacc       60
tgtacagcct ctggattctc cttcagtagc aactactaca tgtgctgggt ccgccaggct     120
ccagggaagg ggctggagtg gatcgcatgc attttactg gtagtagtgg tagcacttac      180
tacgcgagct gggcgaaagg ccgattcacc atctccaaaa cctcgtcgac cacggtgact     240
ctgcacgtga ccagtctgac agccgcggac acggccacct atttctgtgc gagagatagg     300
gctttgtctg ttgttggtta tttctatgct gcatactact tgacttctg ggcccaggc       360
accctggtca ccgtctcctc a                                               381
```

<210> SEQ ID NO 81
<211> LENGTH: 351
<212> TYPE: DNA
<213> ORGANISM: Artificial Sequence

```
<220> FEATURE:
<223> OTHER INFORMATION: polynucleotide

<400> SEQUENCE: 81
cagtcggtgg aggagtccgg gggtcgcctg gtcacgcctg ggacacccct gacactcacc      60
tgcacagcct ctggaatcga cctcagtagc tatgcaatga tctgggtccg ccaggctcca     120
ggagagggac tggaatacat cggattcatt gatgctggtg atggtaacac ttactacgcg     180
agctgggcaa aaggccgatt caccatctcc aaaacctcga ccacggtgga tctgaaaatc     240
accagtccga caaccgagga cacggccacc tatttctgtg ccagaggaga tcctggttgg     300
agtaatggtt ttgccttgtg gggccaaggc accctggtca ccgtctcctc a              351

<210> SEQ ID NO 82
<211> LENGTH: 351
<212> TYPE: DNA
<213> ORGANISM: Artificial Sequence
<220> FEATURE:
<223> OTHER INFORMATION: polynucleotide

<400> SEQUENCE: 82
cagtcggtgg aggagtccgg gggtcgcctg gtcacgcctg ggacacccct gacactcacc      60
tgcacagtct ctggattctc cctcagtacc tacaatatgt gctgggtccg ccaggctcca     120
gggaagggct tggaatgggt cggtttcatt aattctgatg atagcgcgta ctacgcgagc     180
tgggcgaaag gccgcttcac cttctccaag acctcgacca cggtggatct gaaaatcgcc     240
agtccgacaa ccgaggacac ggccacctat ttctgtgcca gatatgattg ggattattat     300
tatagtcggt tggatctctg gggcccgggc accctggtca ccgtctcctc a              351

<210> SEQ ID NO 83
<211> LENGTH: 351
<212> TYPE: DNA
<213> ORGANISM: Artificial Sequence
<220> FEATURE:
<223> OTHER INFORMATION: polynucleotide

<400> SEQUENCE: 83
cagctggagg agtccggggg aggcctggtc agcctgggg catccctgac actcacctgc      60
acaacttctg gattctctct cagtgataat tatttgtgtt gggtccgcca ggctccaggg     120
cgtgggctgg agtgggtcgc atgcattgga attgttcttc gtagtactgg tgccacttac     180
tacgcgagct gggcggaagg ccgattcacc atctccaaaa cctcgccgac cacggtgact     240
ctggagatga ccagtctgac agccgcggac acggccacct acttctgtgc gctagatctc     300
ggatatggtg gtcctttgtg gggcccgggc accctggtca ccgtctcctc a              351

<210> SEQ ID NO 84
<211> LENGTH: 657
<212> TYPE: DNA
<213> ORGANISM: Artificial Sequence
<220> FEATURE:
<223> OTHER INFORMATION: polynucleotide

<400> SEQUENCE: 84
gccgatgtcg tgatgaccca gactccatcc cccgtgtctg cagctgtggg aggcacagtc      60
accatcaatt gccgggccag tgaggacatt gaaagctttt tagcctggta tcagcagaaa     120
ccagggcagc ctcccaagct cctgatctcc aggacatcca ctctggaatc tggggtctca     180
tcgcggttca aaggcagtgg atcggggaca gagttcattc tcaccatcag cgacctggag     240
```

| | | |
|---|---|---|
| tgtgccgatg ctgccactta ctactgtcaa tgtactgatg gtagtagtag tagtagtagt | 300 | |
| tatggttggg atgctttcgg cggagggacc gaggtggtgg tcaaaggtga tccagttgca | 360 | |
| cctactgtcc tcctcttccc accatctagc gatgaggtgg caactggaac agtcaccatc | 420 | |
| gtgtgtgtgg cgaataaata ctttcccgat gtcaccgtca cctgggaggt ggatggcacc | 480 | |
| acccaaacaa ctggcatcga gaacagtaaa acaccgcaga attctgcaga ttgtacctac | 540 | |
| aacctcagca gcactctgac actgaccagc acacagtaca acagccacaa agagtacacc | 600 | |
| tgcaaggtga cccagggcac gacctcagtc gtccagagct tcagtaggaa gaactgt | 657 | |

<210> SEQ ID NO 85
<211> LENGTH: 657
<212> TYPE: DNA
<213> ORGANISM: Artificial Sequence
<220> FEATURE:
<223> OTHER INFORMATION: polynucleotide

<400> SEQUENCE: 85

| | | |
|---|---|---|
| gccgatgtcg tgatgaccca gactccatcc cccgtgtctg cgcaggtggg aggcacagtc | 60 | |
| accatcaatt gccaggccag tgagagcatt gatagtgact tatcctggta tcaacagaaa | 120 | |
| ccagggcagc ctcccaagct cctgatctac aggacattca ctctggaatc tggggtccca | 180 | |
| tcgcggttca aaggcagtgg atctgggaca gactacactc tcaccatcag cgacctggag | 240 | |
| tgtgccgatg ctgccattta ctactgtcaa tgcactgatg gtagtagtat tagtggtagt | 300 | |
| tatggttggg atgctttcgg cggagggacc gaggtggtgg tcaaaggtga tccagttgca | 360 | |
| cctactgtcc tcctcttccc accatctagc gatgaggtgg caactggaac agtcaccatc | 420 | |
| gtgtgtgtgg cgaataaata ctttcccgat gtcaccgtca cctgggaggt ggatggcacc | 480 | |
| acccaaacaa ctggcatcga gaacagtaaa acaccgcaga attctgcaga ttgtacctac | 540 | |
| aacctcagca gcactctgac actgaccagc acacagtaca acagccacaa agagtacacc | 600 | |
| tgcaaggtga cccagggcac gacctcagtc gtccagagct tcagtaggaa gaactgt | 657 | |

<210> SEQ ID NO 86
<211> LENGTH: 657
<212> TYPE: DNA
<213> ORGANISM: Artificial Sequence
<220> FEATURE:
<223> OTHER INFORMATION: polynucleotide

<400> SEQUENCE: 86

| | | |
|---|---|---|
| gccgatgtcg tgatgaccca gactccatcc cccgtgtctg cagctgtggg aggcacagtc | 60 | |
| accatcaatt gccgggccag tgaggacatt gaaagctttt tagcctggta tcagcagaaa | 120 | |
| ccagggcagc ctcccaagct cctgatgtcc aggacatcca ctctggaatc tggggtccca | 180 | |
| tcgcggttca aaggcagtgg atctgggaca gagttcactc tcaccatcag cgacctggag | 240 | |
| tgtgccgatg ctgccacata ttactgtcaa tgtactgatg gtagtagtag tagtagtagt | 300 | |
| tatggttggg atgctttcgg cggagggacc gaggtggtgg tcaaaggtga tccagttgca | 360 | |
| cctactgtcc tcctcttccc accatctagc gatgaggtgg caactggaac agtcaccatc | 420 | |
| gtgtgtgtgg cgaataaata ctttcccgat gtcaccgtca cctgggaggt ggatggcacc | 480 | |
| acccaaacaa ctggcatcga gaacagtaaa acaccgcaga attctgcaga ttgtacctac | 540 | |
| aacctcagca gcactctgac actgaccagc acacagtaca acagccacaa agagtacacc | 600 | |
| tgcaaggtga cccagggcac gacctcagtc gtccagagct tcagtaggaa gaactgt | 657 | |

<210> SEQ ID NO 87
<211> LENGTH: 651
<212> TYPE: DNA
<213> ORGANISM: Artificial Sequence
<220> FEATURE:
<223> OTHER INFORMATION: polynucleotide

<400> SEQUENCE: 87

```
gctgacattg tgatgaccca gactccagcc tccgtgtctg gagctgtggg aggcacagtc    60
accatcaagt gccaggccag tcagagcatt aggaatgaat tatcctggta tcagcagaaa   120
ccagggcagc ctcccaagct cctgatctac aaggcatcca ctctggcatc tggggtccca   180
tcgcggttca gtggcagtgg atttgggaca gagttcactc tcaccatcag cggtgtgcag   240
tgtgatgatg ctgccactta ctactgtcaa acaattatg gtactaggcg taataattat   300
gttttccctt cggcggagg gaccgaggtg gtggtcaaag tgatccagt tgcacctact   360
gtcctcctct tcccaccatc tagcgatgag gtggcaactg aacagtcac catcgtgtgt   420
gtggcgaata atactttcc cgatgtcacc gtcacctggg aggtggatgg caccacccaa   480
acaactggca tcgagaacag taaaacaccg cagaattctg cagattgtac ctacaacctc   540
agcagcactc tgacactgac cagcacacag tacaacagcc acaaagagta cacctgcaag   600
gtgacccagg gcacgacctc agtcgtccag agcttcagta ggaagaactg t            651
```

<210> SEQ ID NO 88
<211> LENGTH: 645
<212> TYPE: DNA
<213> ORGANISM: Artificial Sequence
<220> FEATURE:
<223> OTHER INFORMATION: polynucleotide

<400> SEQUENCE: 88

```
gctgacatcg tgctgaccca gactccagcc tccgtgtctg cagctgtggg aggcacagtc    60
agcatcagtt gccagtccag tgaaagtgtt tataataaca actacttatc ctggtttcag   120
cagaaaccag ggcagcctcc caagctcctg atctatggtg catccactct ggcatctggg   180
gtcccatcgc ggtttgaagg cagtggatct gggacacagt tcactctcac catcagcgac   240
gtgcagtgtg atgatgctgc cacttactac tgtctaggcg attatattat tattgagaat   300
attttcggcg gagggaccga ggtggtggtc aaaggtgatc cagttgcacc tactgtcctc   360
ctcttcccac catctagcga tgaggtggca actgaacag tcaccatcgt gtgtgtggcg   420
aataaatact ttcccgatgt caccgtcacc tgggaggtgg atggcaccac ccaaacaact   480
ggcatcgaga acagtaaaac accgcagaat tctgcagatt gtacctacaa cctcagcagc   540
actctgacac tgaccagcac acagtacaac agccacaaag gtacacctg caaggtgacc   600
cagggcacga cctcagtcgt ccagagcttc agtaggaaga actgt                    645
```

<210> SEQ ID NO 89
<211> LENGTH: 639
<212> TYPE: DNA
<213> ORGANISM: Artificial Sequence
<220> FEATURE:
<223> OTHER INFORMATION: polynucleotide

<400> SEQUENCE: 89

```
gcgcaagtgc tgacccagac tccagcctcc gtgtctgcgg ctgtgggagg cacagtcacc    60
atcaattgcc aggccagtca gagtgtttat aacaacaaaa atttagcctg gtatcagcag   120
aaaccagggc agcctcccaa gctcctgatc tattttttcat ccactctggc atctggggtc   180
```

```
ccatcgcggt tcagaggcag tggatctggg acacagttca ctctcaccat cagtggcgtg      240
cagtgtggcg atgctgccac ttactactgt ctaggcgaat tggtagtat ttgggctttc       300 ggcggaggga ccgaggtggt ggtcaaaggt gatccagttg cacctactgt cctcctcttc      360
ccaccatcta gcgatgaggt ggcaactgga acagtcacca tcgtgtgtgt ggcgaataaa      420
tactttcccg atgtcaccgt cacctgggag gtggatggca ccacccaaac aactggcatc      480
gagaacagta aaacaccgca gaattctgca gattgtacct acaacctcag cagcactctg      540
acactgacca gcacacagta acagccac aaagagtaca cctgcaaggt gacccagggc        600
acgacctcag tcgtccagag cttcagtagg aagaactgt                             639
```

<210> SEQ ID NO 90
<211> LENGTH: 1347
<212> TYPE: DNA
<213> ORGANISM: Artificial Sequence
<220> FEATURE:
<223> OTHER INFORMATION: polynucleotide
<400> SEQUENCE: 90

```
cagtcgttgg aggagtccgg gggagacctg gtcaagcctg gggcatctct gacactcacc       60
tgcaaagcct ctggaatcgc cttcagtaac gactacatgt gctgggtccg ccaggctcca      120
gggaaggggc tggagtggat cgcatgtatt tttactggta gtagtggtag tacttactac      180
gcgagctggg cgaaaggtcg attcaccatc tccaaaacct cgtcgaccac ggtgactctg      240
caaatgacca gtctgacagc cgcggacacg gccacctatt tctgtgcgag agatagggct      300
atttctgtac ttggttattt ctatgctgca tacttctttg acttctgggg cccaggcacc      360
ctggtcaccg tctcctcagg gcaacctaag gctccatcag tcttcccact ggccccctgc      420
tgcggggaca cacccagctc cacggtgacc ttgggctgcc tggtcaaagg ctacctcccg      480
gagccagtga ccgtgacctg gaactcgggc accctcacca tggggtacg caccttcccg      540 tccgtccggc agtcctcagg cctctactcg ctgagcagcg tggtgagcgt gacctcaagc      600
agccagcccg tcacctgcaa cgtggcccac ccagccacca caccaaagt ggacaagacc       660 gttgcgccct cgacatgcag caagcccacg tgcccacccc ctgaactcct ggggggaccg      720
tctgtcttca tcttcccccc aaaacccaag gacaccctca tgatctcacg cacccccgag      780
gtcacatgcg tggtggtgga cgtgagccag gatgaccccg aggtgcagtt cacatggtac      840
ataaacaacg agcaggtgcg caccgcccgg ccgccgctac gggagcagca gttcaacagc      900
acgatccgcg tggtcagcac cctccccatc gcgcaccagg actggctgag gggcaaggag      960
ttcaagtgca aagtccacaa caaggcactc ccggcccca tcgagaaaac catctccaaa      1020
gccagagggc agcccctgga gccgaaggtc tacaccatgg gcctccccg ggaggagctg      1080 agcagcaggt cggtcagcct gacctgcatg atcaacggct ctaccctc cgacatctcg       1140 gtggagtggg agaagaacgg gaaggcagag gacaactaca agaccacgcc ggccgtgctg     1200
gacagcgacg gctcctactt cctctacagc aagctctcag tgcccacgag tgagtggcag     1260
cggggcgacg tcttcacctg ctccgtgatg cacgaggcct tgcacaacca ctacacgcag     1320
aagtccatct cccgctctcc gggtaaa                                         1347
```

<210> SEQ ID NO 91
<211> LENGTH: 1347
<212> TYPE: DNA
<213> ORGANISM: Artificial Sequence
<220> FEATURE:
<223> OTHER INFORMATION: polynucleotide

<400> SEQUENCE: 91

```
cagtcgttgg aggagtccgg gggaggcctg gtccagcctg agggatccct gacactcacc      60
tgcacagctt ctggattctc cttcaatagc agctcctaca tgtgctgggt ccgccaggct     120
ccagggaagg ggctggagtg gatcggatgc attttactg gtagtagtgg taataccctac     180
tacgcgacct gggcgcaagg tcgattcacc atctccaaga cctcgaccac ggtgactctg     240
gaaatgacca gtctgacagc cgcggacacg gccacctatt tctgtgcgag atatagggct     300
tatttttgg ttggttattt ctatgctaca tattattttg acttatgggg cccaggcacc      360
ctggtcaccg tctcctcagg caacctaag gctccatcag tcttcccact ggccccctgc     420
tgcggggaca cccctctag cacggtgacc ttgggctgcc tggtcaaagg ctacctcccg     480
gagccagtga ccgtgacctg gaactcgggc accctcacca tggggtacg caccttcccg     540
tccgtccggc agtcctcagg cctctactcg ctgagcagcg tggtgagcgt gacctcaagc     600
agccagcccg tcacctgcaa cgtggcccac ccagccacca acaccaaagt ggacaagacc     660
gttgcgccct cgacatgcag caagcccacg tgcccacccc ctgaactcct gggggggaccg     720
tctgtcttca tcttccccc aaaacccaag gacaccctca tgatctcacg cacccccgag     780
gtcacatgcg tggtggtgga cgtgagccag gatgaccccg aggtgcagtt cacatggtac     840
ataaacaacg gcaggtgcg caccgcccgg ccgccgctac gggagcagca gttcaacagc     900
acgatccgcg tggtcagcac cctccccatc gcgcaccagg actggctgag gggcaaggag     960
ttcaagtgca aagtccacaa caaggcactc ccggccccca tcgagaaaac catctccaaa    1020
gccagagggc agcccctgga ccgaaggtc tacaccatgg ccctccccg ggaggagctg     1080
agcagcaggt cggtcagcct gacctgcatg atcaacggct ctacccttc cgacatctcg    1140
gtggagtggg agaagaacgg gaaggcagag acaactaca gaccacgcc ggccgtgctg    1200
gacagcgacg gctcctactt cctctacagc aagctctcag tgcccacgag tgagtggcag    1260
cggggcgacg tcttcacctg ctccgtgatg cacgaggcct tgcacaacca ctacacgcag    1320
aagtccatct cccgctctcc gggtaaa                                         1347
```

<210> SEQ ID NO 92
<211> LENGTH: 1350
<212> TYPE: DNA
<213> ORGANISM: Artificial Sequence
<220> FEATURE:
<223> OTHER INFORMATION: polynucleotide

<400> SEQUENCE: 92

```
cagtcgttgg aggagtccgg gggaggcctg gtccagcctg ggcatctct gacactcacc      60
tgtacagcct ctggattctc cttcagtagc aactactaca tgtgctgggt ccgccaggct     120
ccagggaagg ggctggagtg gatcgcatgc attttactg gtagtagtgg tagcacttac     180
tacgcgagct gggcgaaagg ccgattcacc atctccaaaa cctcgtcgac cacggtgact     240
ctgcacgtga ccagtctgac agccgcggac acggccacct atttctgtgc gagagatagg     300
gctttgtctg ttgttggtta tttctatgct gcatactact ttgacttctg ggcccaggc     360
accctggtca ccgtctcctc agggcaacct aaggctccat cagtcttccc actggccccc     420
tgctgcgggg acacaccctc tagcacggtg accttgggct gcctggtcaa aggctacctc     480
ccggagccag tgaccgtgac ctggaactcg gcaccctca ccaatggggt acgcaccttc     540
ccgtccgtcc ggcagtcctc aggcctctac tcgctgagca gcgtggtgag cgtgacctca     600
```

```
agcagccagc ccgtcacctg caacgtggcc cacccagcca ccaacaccaa agtggacaag    660
accgttgcgc cctcgacatg cagcaagccc acgtgcccac ccctgaact  cctgggggga    720 ccgtctgtct tcatcttccc cccaaaaccc aaggacaccc tcatgatctc acgcaccccc    780
gaggtcacat gcgtggtggt ggacgtgagc caggatgacc ccgaggtgca gttcacatgg    840
tacataaaca cgagcaggt  gcgcaccgcc cggccgccgc tacgggagca gcagttcaac    900
agcacgatcc gcgtggtcag caccctcccc atcgcgcacc aggactggct gaggggcaag    960
gagttcaagt gcaaagtcca caacaaggca ctcccggccc catcgagaa  accatctcc    1020 aaagccagag gcagcccct  ggagccgaag gtctacacca tgggccctcc ccggaggag    1080 ctgagcagca ggtcggtcag cctgacctgc atgatcaacg gcttctaccc ttccgacatc    1140
tcggtggagt gggagaagaa cgggaaggca gaggacaact acaagaccac gccggccgtg    1200
ctggacagcg acggctccta cttcctctac agcaagctct cagtgccac  gagtgagtgg    1260 cagcggggcg acgtcttcac ctgctccgtg atgcacgagg ccttgcacaa ccactacacg    1320
cagaagtcca tctcccgctc tccgggtaaa                                    1350

<210> SEQ ID NO 93
<211> LENGTH: 1320
<212> TYPE: DNA
<213> ORGANISM: Artificial Sequence
<220> FEATURE:
<223> OTHER INFORMATION: polynucleotide

<400> SEQUENCE: 93
cagtcggtgg aggagtccgg gggtcgcctg gtcacgcctg gacacccct  gacactcacc     60 tgcacagcct ctggaatcga cctcagtagc tatgcaatga tctgggtccg ccaggctcca    120
ggagagggac tggaatacat cggattcatt gatgctggtg atggtaacac ttactacgcg    180
agctgggcaa aaggccgatt caccatctcc aaaacctcga ccacggtgga tctgaaaatc    240
accagtccga caaccgagga cacggccacc tatttctgtg ccagaggaga tcctggttgg    300
agtaatggtt ttgccttgtg gggccaaggc accctggtca ccgtctcctc agggcaacct    360
aaggctccat cagtcttccc actggcccc  tgctgcgggg acacaccctc tagcacggtg    420
accttgggct gcctggtcaa aggctacctc ccggagccag tgaccgtgac ctggaactcg    480
ggcaccctca ccaatggggt acgcaccttc ccgtccgtcc ggcagtcctc aggcctctac    540
tcgctgagca gcgtggtgag cgtgacctca agcagccagc ccgtcacctg caacgtggcc    600
cacccagcca ccaacaccaa agtggacaag accgttgcgc cctcgacatg cagcaagccc    660
acgtgcccac ccctgaact  cctgggggga ccgtctgtct tcatcttccc cccaaaaccc    720
aaggacaccc tcatgatctc acgcaccccc gaggtcacat gcgtggtggt ggacgtgagc    780
caggatgacc ccgaggtgca gttcacatgg tacataaaca cgagcaggt  gcgcaccgcc    840 cggccgccgc tacgggagca gcagttcaac agcacgatcc gcgtggtcag caccctcccc    900
atcgcgcacc aggactggct gaggggcaag gagttcaagt gcaaagtcca caacaaggca    960
ctcccggccc catcgagaa  accatctcc  aaagccagag gcagcccct  ggagccgaag   1020 gtctacacca tgggccctcc ccggaggag  ctgagcagca ggtcggtcag cctgacctgc   1080
atgatcaacg gcttctaccc ttccgacatc tcggtggagt gggagaagaa cgggaaggca   1140
gaggacaact acaagaccac gccggccgtg ctggacagcg acggctccta cttcctctac   1200
agcaagctct cagtgccac  gagtgagtgg cagcggggcg acgtcttcac ctgctccgtg   1260
atgcacgagg ccttgcacaa ccactacacg cagaagtcca tctcccgctc tccgggtaaa   1320
```

<210> SEQ ID NO 94
<211> LENGTH: 1320
<212> TYPE: DNA
<213> ORGANISM: Artificial Sequence
<220> FEATURE:
<223> OTHER INFORMATION: polynucleotide

<400> SEQUENCE: 94

| | | | | | |
|---|---|---|---|---|---|
| cagtcggtgg | aggagtccgg | gggtcgcctg | gtcacgcctg | ggacacccct | gacactcacc | 60 |
| tgcacagtct | ctggattctc | cctcagtacc | tacaatatgt | gctgggtccg | ccaggctcca | 120 |
| gggaagggct | tggaatgggt | cggtttcatt | aattctgatg | atagcgcgta | ctacgcgagc | 180 |
| tgggcgaaag | gccgcttcac | cttctccaag | acctcgacca | cggtggatct | gaaaatcgcc | 240 |
| agtccgacaa | ccgaggacac | ggccacctat | ttctgtgcca | gatatgattg | ggattattat | 300 |
| tatagtcggt | tggatctctg | gggcccgggc | accctggtca | ccgtctcctc | agggcaacct | 360 |
| aaggctccat | cagtcttccc | actggccccc | tgctgcgggg | acacaccctc | tagcacggtg | 420 |
| accttgggct | gcctggtcaa | ggctacctc | ccggagccag | tgaccgtgac | ctggaactcg | 480 |
| ggcaccctca | ccaatgggt | acgcaccttc | ccgtccgtcc | ggcagtcctc | aggcctctac | 540 |
| tcgctgagca | gcgtggtgag | cgtgacctca | agcagccagc | ccgtcacctg | caacgtggcc | 600 |
| cacccagcca | ccaacaccaa | agtggacaag | accgttgcgc | cctcgacatg | cagcaagccc | 660 |
| acgtgcccac | cccctgaact | cctgggggga | ccgtctgtct | tcatcttccc | cccaaaaccc | 720 |
| aaggacaccc | tcatgatctc | acgcaccccc | gaggtcacat | gcgtggtggt | ggacgtgagc | 780 |
| caggatgacc | ccgaggtgca | gttcacatgg | tacataaaca | acgagcaggt | gcgcaccgcc | 840 |
| cggccgccgc | tacgggagca | gcagttcaac | agcacgatcc | gcgtggtcag | cacccctccc | 900 |
| atcgcgcacc | aggactggct | gagggcaag | gagttcaagt | gcaaagtcca | caacaaggca | 960 |
| ctcccggccc | ccatcgagaa | aaccatctcc | aaagccagag | gcagccccct | ggagccgaag | 1020 |
| gtctacacca | tgggccctcc | ccgggaggag | ctgagcagca | ggtcggtcag | cctgacctgc | 1080 |
| atgatcaacg | gcttctaccc | ttccgacatc | tcggtggagt | gggagaagaa | cgggaaggca | 1140 |
| gaggacaact | acaagaccac | gccggccgtg | ctggacagcg | acggctccta | cttcctctac | 1200 |
| agcaagctct | cagtgcccac | gagtgagtgg | cagcggggcg | acgtcttcac | ctgctccgtg | 1260 |
| atgcacgagg | ccttgcacaa | ccactacacg | cagaagtcca | tctcccgctc | tccgggtaaa | 1320 |

<210> SEQ ID NO 95
<211> LENGTH: 1320
<212> TYPE: DNA
<213> ORGANISM: Artificial Sequence
<220> FEATURE:
<223> OTHER INFORMATION: polynucleotide

<400> SEQUENCE: 95

| | | | | | |
|---|---|---|---|---|---|
| cagctggagg | agtccggggg | aggcctggtc | cagcctgggg | catccctgac | actcacctgc | 60 |
| acaacttctg | gattctctct | cagtgataat | tatttgtgtt | gggtccgcca | ggctccaggg | 120 |
| cgtgggctgg | agtgggtcgc | atgcattgga | attgttcttc | gtagtactgg | tgccacttac | 180 |
| tacgcgagct | gggcggaagg | ccgattcacc | atctccaaaa | cctcgccgac | cacggtgact | 240 |
| ctggagatga | ccagtctgac | agccgcggac | acggccacct | acttctgtgc | gctagatctc | 300 |
| ggatatggtg | gtccttttgtg | gggcccgggc | accctggtca | ccgtctcctc | agggcaacct | 360 |
| aaggctccat | cagtcttccc | actggccccc | tgctgcgggg | acacaccctc | tagcacggtg | 420 |

```
accttgggct gcctggtcaa aggctacctc ccggagccag tgaccgtgac ctggaactcg    480
ggcaccctca ccaatggggt acgcaccttc ccgtccgtcc ggcagtcctc aggcctctac    540
tcgctgagca gcgtggtgag cgtgacctca agcagccagc ccgtcacctg caacgtggcc    600
cacccagcca ccaacaccaa agtggacaag accgttgcgc cctcgacatg cagcaagccc    660
acgtgcccac ccctgaact cctgggggga ccgtctgtct tcatcttccc cccaaaaccc    720
aaggacaccc tcatgatctc acgcaccccc gaggtcacat gcgtggtggt ggacgtgagc    780
caggatgacc ccgaggtgca gttcacatgg tacataaaca acgagcaggt gcgcaccgcc    840
cggccgccgc tacgggagca gcagttcaac agcacgatcc gcgtggtcag cacccctccc    900
atcgcgcacc aggactggct gaggggcaag gagttcaagt gcaaagtcca caacaaggca    960
ctcccggccc ccatcgagaa aaccatctcc aaagccagag gcagcccct ggagccgaag    1020
gtctacacca tgggccctcc ccgggaggag ctgagcagca ggtcggtcag cctgacctgc    1080
atgatcaacg gcttctaccc ttccgacatc tcggtggagt gggagaagaa cgggaaggca    1140
gaggacaact acaagaccac gccggccgtg ctggacagcg acggctccta cttcctctac    1200
agcaagctct cagtgcccac gagtgagtgg cagcggggcg acgtcttcac ctgctccgtg    1260
atgcacgagg ccttgcacaa ccactacacg cagaagtcca tctcccgctc tccgggtaaa    1320
```

<210> SEQ ID NO 96
<211> LENGTH: 22
<212> TYPE: PRT
<213> ORGANISM: Artificial Sequence
<220> FEATURE:
<223> OTHER INFORMATION: polypeptide

<400> SEQUENCE: 96

Met Asp Met Arg Val Pro Ala Gln Leu Leu Gly Leu Leu Leu Leu Trp
1               5                   10                  15
Leu Arg Gly Ala Arg Cys
            20

<210> SEQ ID NO 97
<211> LENGTH: 19
<212> TYPE: PRT
<213> ORGANISM: Artificial Sequence
<220> FEATURE:
<223> OTHER INFORMATION: polypeptide

<400> SEQUENCE: 97

Met Ala Trp Ala Leu Leu Leu Leu Thr Leu Leu Thr Gln Gly Thr Gly
1               5                   10                  15
Ser Trp Ala

<210> SEQ ID NO 98
<211> LENGTH: 19
<212> TYPE: PRT
<213> ORGANISM: Artificial Sequence
<220> FEATURE:
<223> OTHER INFORMATION: polypeptide

<400> SEQUENCE: 98

Met Thr Cys Ser Pro Leu Leu Leu Thr Leu Leu Ile His Cys Thr Gly
1               5                   10                  15
Ser Trp Ala

<210> SEQ ID NO 99
<211> LENGTH: 20

```
<212> TYPE: PRT
<213> ORGANISM: Artificial Sequence
<220> FEATURE:
<223> OTHER INFORMATION: polypeptide

<400> SEQUENCE: 99

Met Glu Ala Pro Ala Gln Leu Leu Phe Leu Leu Leu Leu Trp Leu Pro
1               5                   10                  15

Asp Thr Thr Gly
            20

<210> SEQ ID NO 100
<211> LENGTH: 19
<212> TYPE: PRT
<213> ORGANISM: Artificial Sequence
<220> FEATURE:
<223> OTHER INFORMATION: polypeptide

<400> SEQUENCE: 100

Met Glu Trp Thr Trp Arg Val Leu Phe Leu Val Ala Ala Ala Thr Gly
1               5                   10                  15

Ala His Ser

<210> SEQ ID NO 101
<211> LENGTH: 20
<212> TYPE: PRT
<213> ORGANISM: Artificial Sequence
<220> FEATURE:
<223> OTHER INFORMATION: polypeptide

<400> SEQUENCE: 101

Met Glu Thr Pro Ala Gln Leu Leu Phe Leu Leu Leu Leu Trp Leu Pro
1               5                   10                  15

Asp Thr Thr Gly
            20

<210> SEQ ID NO 102
<211> LENGTH: 20
<212> TYPE: PRT
<213> ORGANISM: Artificial Sequence
<220> FEATURE:
<223> OTHER INFORMATION: polypeptide

<400> SEQUENCE: 102

Met Glu Thr Pro Ala Gln Leu Leu Phe Leu Leu Leu Leu Trp Leu Pro
1               5                   10                  15

Asp Thr Thr Gly
            20

<210> SEQ ID NO 103
<211> LENGTH: 19
<212> TYPE: PRT
<213> ORGANISM: Artificial Sequence
<220> FEATURE:
<223> OTHER INFORMATION: polypeptide

<400> SEQUENCE: 103

Met Lys His Leu Trp Phe Phe Leu Leu Leu Val Ala Ala Pro Arg Trp
1               5                   10                  15

Val Leu Ser

<210> SEQ ID NO 104
<211> LENGTH: 19
<212> TYPE: PRT
```

```
<213> ORGANISM: Artificial Sequence
<220> FEATURE:
<223> OTHER INFORMATION: polypeptide

<400> SEQUENCE: 104

Met Glu Trp Ser Trp Val Phe Leu Phe Phe Leu Ser Val Thr Thr Gly
1               5                   10                  15

Val His Ser

<210> SEQ ID NO 105
<211> LENGTH: 22
<212> TYPE: PRT
<213> ORGANISM: Artificial Sequence
<220> FEATURE:
<223> OTHER INFORMATION: polypeptide

<400> SEQUENCE: 105

Met Asp Ile Arg Ala Pro Thr Gln Leu Leu Gly Leu Leu Leu Leu Trp
1               5                   10                  15

Leu Pro Gly Ala Lys Cys
            20

<210> SEQ ID NO 106
<211> LENGTH: 22
<212> TYPE: PRT
<213> ORGANISM: Artificial Sequence
<220> FEATURE:
<223> OTHER INFORMATION: polypeptide

<400> SEQUENCE: 106

Met Asp Ile Arg Ala Pro Thr Gln Leu Leu Gly Leu Leu Leu Leu Trp
1               5                   10                  15

Leu Pro Gly Ala Arg Cys
            20

<210> SEQ ID NO 107
<211> LENGTH: 22
<212> TYPE: PRT
<213> ORGANISM: Artificial Sequence
<220> FEATURE:
<223> OTHER INFORMATION: polypeptide

<400> SEQUENCE: 107

Met Asp Thr Arg Ala Pro Thr Gln Leu Leu Gly Leu Leu Leu Leu Trp
1               5                   10                  15

Leu Pro Gly Ala Thr Phe
            20

<210> SEQ ID NO 108
<211> LENGTH: 22
<212> TYPE: PRT
<213> ORGANISM: Artificial Sequence
<220> FEATURE:
<223> OTHER INFORMATION: polypeptide

<400> SEQUENCE: 108

Met Asp Thr Arg Ala Pro Thr Gln Leu Leu Gly Leu Leu Leu Leu Trp
1               5                   10                  15

Leu Pro Gly Ala Arg Cys
            20

<210> SEQ ID NO 109
<211> LENGTH: 19
<212> TYPE: PRT
```

<213> ORGANISM: Artificial Sequence
<220> FEATURE:
<223> OTHER INFORMATION: polypeptide

<400> SEQUENCE: 109

```
Met Glu Thr Gly Leu Arg Trp Leu Leu Leu Val Ala Val Leu Lys Gly
1               5                   10                  15

Val Gln Cys
```

<210> SEQ ID NO 110
<211> LENGTH: 21
<212> TYPE: PRT
<213> ORGANISM: Artificial Sequence
<220> FEATURE:
<223> OTHER INFORMATION: polypeptide

<400> SEQUENCE: 110

```
Met Glu Thr Gly Leu Arg Trp Leu Leu Leu Val Ala Val Leu Lys Gly
1               5                   10                  15

Val Gln Cys Gln Glu
            20
```

<210> SEQ ID NO 111
<211> LENGTH: 22
<212> TYPE: PRT
<213> ORGANISM: Artificial Sequence
<220> FEATURE:
<223> OTHER INFORMATION: polypeptide

<400> SEQUENCE: 111

```
Met Asp Met Arg Ala Pro Thr Gln Leu Leu Gly Leu Leu Leu Leu Trp
1               5                   10                  15

Leu Pro Gly Ala Arg Cys
            20
```

<210> SEQ ID NO 112
<211> LENGTH: 8
<212> TYPE: PRT
<213> ORGANISM: Artificial Sequence
<220> FEATURE:
<223> OTHER INFORMATION: polypeptide

<400> SEQUENCE: 112

```
Val Leu Gly Lys Arg Tyr Lys Gln
1               5
```

<210> SEQ ID NO 113
<211> LENGTH: 32
<212> TYPE: PRT
<213> ORGANISM: Artificial Sequence
<220> FEATURE:
<223> OTHER INFORMATION: polypeptide

<400> SEQUENCE: 113

```
Phe Thr Asp Ser Tyr Ser Arg Tyr Arg Lys Gln Met Ala Val Lys Lys
1               5                   10                  15

Tyr Leu Ala Ala Val Leu Gly Lys Arg Tyr Lys Gln Arg Val Lys Asn
            20                  25                  30
```

<210> SEQ ID NO 114
<211> LENGTH: 30
<212> TYPE: PRT
<213> ORGANISM: Artificial Sequence
<220> FEATURE:
<223> OTHER INFORMATION: polypeptide

```
<400> SEQUENCE: 114

Phe Thr Asp Ser Tyr Ser Arg Tyr Arg Lys Gln Met Ala Val Lys Lys
1               5                   10                  15

Tyr Leu Ala Ala Val Leu Gly Lys Arg Tyr Lys Gln Arg Val
            20                  25                  30

<210> SEQ ID NO 115
<211> LENGTH: 8
<212> TYPE: PRT
<213> ORGANISM: Artificial Sequence
<220> FEATURE:
<223> OTHER INFORMATION: polypeptide

<400> SEQUENCE: 115

Tyr Lys Gln Arg Val Lys Asn Lys
1               5

<210> SEQ ID NO 116
<211> LENGTH: 12
<212> TYPE: PRT
<213> ORGANISM: Artificial Sequence
<220> FEATURE:
<223> OTHER INFORMATION: polypeptide

<400> SEQUENCE: 116

Leu Gly Lys Arg Tyr Lys Gln Arg Val Lys Asn Lys
1               5                   10

<210> SEQ ID NO 117
<211> LENGTH: 25
<212> TYPE: PRT
<213> ORGANISM: Artificial Sequence
<220> FEATURE:
<223> OTHER INFORMATION: polypeptide

<400> SEQUENCE: 117

Arg Lys Gln Met Ala Val Lys Lys Tyr Leu Ala Ala Val Leu Gly Lys
1               5                   10                  15

Arg Tyr Lys Gln Arg Val Lys Asn Lys
            20                  25

<210> SEQ ID NO 118
<211> LENGTH: 17
<212> TYPE: PRT
<213> ORGANISM: Artificial Sequence
<220> FEATURE:
<223> OTHER INFORMATION: polypeptide

<400> SEQUENCE: 118

Ser Arg Tyr Arg Lys Gln Met Ala Val Lys Lys Tyr Leu Ala Ala Val
1               5                   10                  15

Leu

<210> SEQ ID NO 119
<211> LENGTH: 24
<212> TYPE: PRT
<213> ORGANISM: Artificial Sequence
<220> FEATURE:
<223> OTHER INFORMATION: polypeptide

<400> SEQUENCE: 119

Gly Ile Phe Thr Asp Ser Tyr Ser Arg Tyr Arg Lys Gln Met Ala Val
1               5                   10                  15
```

```
Lys Lys Tyr Leu Ala Ala Val Leu
            20

<210> SEQ ID NO 120
<211> LENGTH: 33
<212> TYPE: PRT
<213> ORGANISM: Artificial Sequence
<220> FEATURE:
<223> OTHER INFORMATION: polypeptide

<400> SEQUENCE: 120

Phe Thr Asp Ser Tyr Ser Arg Tyr Arg Lys Gln Met Ala Val Lys Lys
1               5                   10                  15

Tyr Leu Ala Ala Val Leu Gly Lys Arg Tyr Lys Gln Arg Val Lys Asn
            20                  25                  30

Lys

<210> SEQ ID NO 121
<211> LENGTH: 31
<212> TYPE: PRT
<213> ORGANISM: Artificial Sequence
<220> FEATURE:
<223> OTHER INFORMATION: polypeptide

<400> SEQUENCE: 121

Phe Thr Asp Ser Tyr Ser Arg Tyr Arg Lys Gln Met Ala Val Lys Lys
1               5                   10                  15

Tyr Leu Ala Ala Val Leu Gly Lys Arg Tyr Lys Gln Arg Val Lys
            20                  25                  30

<210> SEQ ID NO 122
<211> LENGTH: 15
<212> TYPE: PRT
<213> ORGANISM: Artificial Sequence
<220> FEATURE:
<223> OTHER INFORMATION: polypeptide

<400> SEQUENCE: 122

Phe Thr Asp Ser Tyr Ser Arg Tyr Arg Lys Gln Met Ala Val Lys
1               5                   10                  15

<210> SEQ ID NO 123
<211> LENGTH: 10
<212> TYPE: PRT
<213> ORGANISM: Artificial Sequence
<220> FEATURE:
<223> OTHER INFORMATION: polypeptide

<400> SEQUENCE: 123

Ser Tyr Ser Arg Tyr Arg Lys Gln Met Ala
1               5                   10

<210> SEQ ID NO 124
<211> LENGTH: 8
<212> TYPE: PRT
<213> ORGANISM: Artificial Sequence
<220> FEATURE:
<223> OTHER INFORMATION: polypeptide

<400> SEQUENCE: 124

Gln Met Ala Val Lys Lys Tyr Leu
1               5

<210> SEQ ID NO 125
<211> LENGTH: 7
```

```
<212> TYPE: PRT
<213> ORGANISM: Artificial Sequence
<220> FEATURE:
<223> OTHER INFORMATION: polypeptide

<400> SEQUENCE: 125

Val Lys Lys Tyr Leu Ala Ala
1               5

<210> SEQ ID NO 126
<211> LENGTH: 5
<212> TYPE: PRT
<213> ORGANISM: Artificial Sequence
<220> FEATURE:
<223> OTHER INFORMATION: polypeptide

<400> SEQUENCE: 126

Arg Val Lys Asn Lys
1               5

<210> SEQ ID NO 127
<211> LENGTH: 8
<212> TYPE: PRT
<213> ORGANISM: Artificial Sequence
<220> FEATURE:
<223> OTHER INFORMATION: polypeptide

<400> SEQUENCE: 127

Arg Tyr Lys Gln Arg Val Lys Asn
1               5
```